United States Patent
Kondo et al.

(10) Patent No.: US 6,194,542 B1
(45) Date of Patent: Feb. 27, 2001

(54) METHOD OF DETECTING CYTOMEGALOVIRUS (CMV)

(75) Inventors: Kazuhiro Kondo, Osaka (JP); Edward S. Mocarski, Jr., Portola Valley, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 08/976,161

(22) Filed: Nov. 21, 1997

Related U.S. Application Data

(62) Division of application No. 08/450,945, filed on May 23, 1995.

(51) Int. Cl.[7] ............ A61K 38/00; C07K 1/00; C12Q 1/68; C07H 19/00
(52) U.S. Cl. .......... 530/300; 530/350; 436/22.1; 435/6
(58) Field of Search ............... 435/6; 530/300, 530/350; 536/22.1

(56) References Cited

U.S. PATENT DOCUMENTS 4,299,916 * 11/1981 Litman et al. ............ 435/6
5,460,942 * 10/1995 Chou et al. ............ 435/6
5,478,727 * 12/1995 Roizman et al. ............ 435/23

OTHER PUBLICATIONS

Kondo, R., et al., "Human Cytomegalovirus Latent Infection of Granulocyte–Macrophage Progenitors," Proc. Natl., Acad. Sci. USA 91:11879 (1994).*

Tamashiro, J.C., et al., "Structure of Heterogeneous L–S Junction Region of Human Cytomegalovirus Strain AD169 DNA," J. of Virology 52(2):541–548 (1984).*

Wu,, T.–C., et al., "In Situ Detection of Human Cytomegalovirus Immediate–Early Gene Transcripts within Cardiac Myocytes of Patients with HIV–Associated Cardiomyopathy," AIDS 6:777 (1992).*

* cited by examiner

Primary Examiner—Jezia Riley
(74) Attorney, Agent, or Firm—Susan T. Evans; Linda R. Judge

(57) ABSTRACT

The present invention provides methods and compositions relating to cytomegalovirus (CMV) latent transcripts, latency-associated polypeptides and antibodies directed against such polypeptide. The polypeptides are encoded by CMV DNA sequences and are produced specifically during latent infection. Also provided are methods of detecting CMV in a sample, particularly CMV in a latent state. The methods include RT-PCR-based methods and immunodiagnostic methods.

3 Claims, 22 Drawing Sheets

| SEQ ID NO: | Name | Sequence |
|---|---|---|
| SEQ ID NO:1 | 112A | 5'CCGGTTGATGAACCGGCAGAAGGAG3' |
| SEQ ID NO:2 | 113B | 5'GAAAGGCCACCGCTTCAGACGTGTC3' |
| SEQ ID NO:3 | 113D | 5'GGACTGCTGCTCCGTCCGTCTCTTG3' |
| SEQ ID NO:4 | 2.7A | 5'CGGATTATCATTTCCCTCTCCTACC3' |
| SEQ ID NO:5 | 2.7B | 5'CCTTGCGGATTGACATTCTTGGTGGT3' |
| SEQ ID NO:6 | IEP1B | 5'CGGTTCACTAAACGAGCTCTGCTTATATAGACC3' |
| SEQ ID NO:7 | IEP1D | 5'ATACGTAGATGTACTGCCAAGTAGG3' |
| SEQ ID NO:8 | IEP1E | 5'GTATCATATGCCAAGTCCGCCCCCTA3' |
| SEQ ID NO:9 | IEP1G | 5'ATAGCAGAGCTCGTTAGTGAACCG3' |
| SEQ ID NO:10 | IEP1H | 5'GTCACTCTTGGCACGGGGAATCCGCGTTCC3' |
| SEQ ID NO:11 | IEP1K | 5'ATGCCCAGTACATGACCTTACGGG3' |
| SEQ ID NO:12 | IEP1M | 5'TCAGATCGCCTGGAGACGCCATCC3' |
| SEQ ID NO:13 | IEP1Q | 5'ACAGGATGGGGTCTCATTTATTATTTACAAATTC3' |
| SEQ ID NO:14 | IEP1S | 5'TGACGTATGTTCCCATAGTAACGC3' |
| SEQ ID NO:15 | IEP2AII | 5'ATGGAGTCCCTCTGCCAAGAGAAAGATGGAC3' |
| SEQ ID NO:16 | IEP2D | 5'CAGGATTATCAGGGTCCATCTTTCTCTTGG3' |
| SEQ ID NO:17 | IEP2E | 5'TCACCGTCCTTGACA3' |
| SEQ ID NO:18 | IEP3A | 5'GTGACCAAGGCCACGACGTT3' |
| SEQ ID NO:19 | IEP3B | 5'TCTGCCAGGACATCTTTCTC3' |
| SEQ ID NO:20 | IEP3C | 5'CAACGAGAACCCGAGAAAGATGTC3' |
| SEQ ID NO:21 | IEP3D | 5'CCAGATAAATGACTGTTAACCTCCTTCC3' |
| SEQ ID NO:22 | IEP3E | 5'TAGCGATAAATGAGTCAGGAGGACG3' |
| SEQ ID NO:23 | IEP3G | 5'TATGTGTTGTTATCCTCCTCTACAG3' |
| SEQ ID NO:24 | IEP4AP | 5'ACAGATTAAGGTTCGAGTGGACATGGTGCG3' |
| SEQ ID NO:25 | IEP4BII | 5'CAATACACTTCATCTCCTCGAAAGG3' |
| SEQ ID NO:26 | IEP4C | 5'CCTGAGGTTATCAGTGTAATGAAGC3' |
| SEQ ID NO:27 | IEP4H | 5'ACGGTTTCACAGGCGTGACACGTTTATTGAG3' |
| SEQ ID NO:28 | IEP4J | 5'GTGACACCAGAGAATCAGAGGAGCTGAC3' |
| SEQ ID NO:29 | IEP5AP | 5'CAATCATGCCGTATCGATTCCAGTAGCAC3' |
| SEQ ID NO:30 | IEP5B | 5'GCGTGGTTTTGCGCGGTTTCTTACG3' |
| SEQ ID NO:31 | IEP5D | 5'CCACCCTGGTTGGTGGAGAAGATGC3' |
| SEQ ID NO:32 | IEP5H | 5'CTTATCTTTCATGATATTGCGCACCTTCTCG3' |
| SEQ ID NO:33 | N1 | 5'GCTGGGTAGTCCCCACCTTTCTAGA3' |
| SEQ ID NO:34 | N2 | 5'CTTATGAGTATTCTTCCAGGGTACTCGAG3' |
| SEQ ID NO:35 | RL-1 | 5'CTTATGAGTATTTCTTCCAGGGTACTCGAGGCTGGGTAGTCCCCACCTTTCTAGATTTTTTTTTTTTTTTT3' |

Fig. 7

```
  1    GGC GAC CGC CCA GCG ACC CCC GCC CGT TGA CGT CAA TAG TGA CGT ATG TTC CCA TAG TAA

61    CGC CAA TAG GGA CTT TCC ATT GAC GTC AAT GGG TGG AGT ATT TAC GGT AAA CTG CCC ACT
                       LSS1-->
121    TGG CAG TAC ATC AAG TGT ATC ATA TGC AAT GTC CGC CCC CTA TTG ACG TCA ATG ACG GTA
                       LSS2-->
181    AAT GGC CCG CCT AGC ATT ATG CCC AGT ACA TGA CCT TAC GGG AGT TTC CTA CTT GGC AGT
           ORF1>
241    ACA TCT ACG TAT TAG TCA TCG CTA TTA CCA TGG TGA TGC GGT TTT GGC AGT ACA CCA ATG
                                                                                 ORF2>
301    GGC GTG GAT AGC GGT TTG ACT CAC GGG GAT TTC CAA GTC TCC ACC CCA TTG ACG TCA ATG

361    GGA GTT TGT TTT GGC ACC AAA ATC AAC GGG ACT TTC CAA AAT GTC GTA ATA ACC CCG CCC

421    CGT TGA CGC AAA TGG GCG GTA GGC GTG TAC GGT GGG AGG TCT ATA TAA GCA GAG CTC GTT
                   ORF3>
                            PSS-->
481    TAG TGA ACC GTC AGA TCG CCT GGA GAC GCC ATC CAC GCT GTT TTG ACC TCC ATA GAA GAC

541    ACC GGG ACC GAT CCA GCC TCC GCG GCC GGG AAC GGT GCA TTG AAC GCG GAT TCC CCG TGG

601    CCA AGA GTG ACT CAC CGT CCT TGA CAC GAT GGA GTC CTC TGC AAG AGA AAA GAT GGA CCC

661    TGA TAA TCC TGA CGA GGG CCC TTC CTC CAA GGT GCC ACG GCC CGA GAC ACC CGT GAC CAA

721    GGC CAC GAC GTT CCT GCA GAC TAT GTT GAG GAA GGA GGT TAA CAG TCA GCT GAG TCT GGG

781    AGA CCC GCT GTT TCC AGA GTT GGC CGA AGA ATC CCT CAA AAC TTT TGA ACG AGT GAC CGA

841    GGA TTG CAA CGA GAA CCC CGA GAA AGA TGT CCT GGC AGA ACT CGT CAA ACA GAT TAA GGT

901    TCG AGT GGA CAT GCT GCG GCA TAG AAT CAA GGA GCA CAT GCT GAA AAA ATA TAC CCA GAC

961    GGA AGA GAA ATT CAC TGG CGC CTT TAA TAT GAT GGG AGG ATG TTT GCA GAA TGC CTT AGA

1021   TAT CTT AGA TAA GGT TCA TGA GCC TTT CGA GGA GAT GAA GTG TAT TGG GCT AAC TAT GCA

1081   GAG CAT GTA TGA GAA CTA CAT TGT ACC TGA GGA TAA GCG GGA GAT GTG GAT GGC TTG TAT

1141   TAA GGA GCT GCA TGA TGT GAG CAA GGG CGC CGC TAA CAA GTT GGG GGG TGC ACT GCA GGC

1201   TAA GGC CCG TGC TAA AAA GGA TGA ACT TAG GAG AAA GAT GAT GTA TAT GTG CTA CAG GAA

1261   TAT AGA GTT CTT TAC CAA GAA CTC AGC CTT CCC TAA GAC CAC CAA TGG CTG CAG TCA GGC
```

Fig. 18A

1321 CAT GGC GGC ATT GCA GAA CTT GCC TCA GTG CTC CCC TGA TGA GAT TAT GGC TTA TGC CCA

1381 GAA AAT ATT TAA GAT TTT GGA TGA GGA GAG AGA CAA GGT GCT CAC GCA CAT TGA TCA CAT

1441 ATT TAT GGA TAT CCT CAC TAC ATG TGT GGA AAC AAT GTG TAA TGA GTA CAA GGT CAC TAG

1501 TGA CGC TTG TAT GAT GAC CAT GTA CGG GGG CAT CTC TCT CTT AAG TGA GTT CTG TCG GGT

1561 GCT GTC CTG CTA TGT CTT AGA GGA GAC TAG TGT GAT GCT GGC CAA GCG GCC TCT GAT AAC

1621 CAA GCC TGA GGT TAT CAG TGT AAT GAA GCG CCG CAT TGA GGA GAT CTG CAT GAA GGT CTT

1681 TGC CCA GTA CAT TCT GGG GGC CGA TCC TCT GAG AGT CTG CTC TCC TAG TGT GGA TGA CCT

1741 ACG GGC CAT CGC CGA GGA GTC AGA TGA GGA AGA GGC TAT TGT AGC CTA CAC TTT GGC CAC

1801 CCG TGG TGC CAG CTC CTC TGA TTC TCT GGT GTC ACC CCC AGA GTC CCC TGT ACC CGC GAC

1861 TAT CCC TCT GTC CTC AGT AAT TGT GGC TGA GAA CAG TGA TCA GGA AGA AAG TGA GCA GAG

1921 TGA TGA GGA AGA GGA GGA GGG TGC TCA GGA GGA GCG GGA GGA CAC TGT GTC TGT CAA GTC

1981 TGA GCC AGT GTC TGA GAT AGA GGA AGT TGC CCC AGA GGA AGA GGA TGG TGC TGA GGA

2041 ACC CAC CGC CTC TGG AGG CAA GAG CAC CCA CCC TAT GGT GAC TAG AAG CAA GGC TGA CCA

2101 GTA AAC TAT TGT ATA TAT ATA TCA GTT ACT GTT ATG GAT CCC ACG TCA CTA TTG TAT ACT

2161 CTA TAT TAT ACT CTA TGT TAT ACT CTG TAA TCC TAC TCA ATA AAC GTG TCA CGC CTG TGA

2221 AAC CG

Fig. 18B

```
1     GTG ACA CCA GAG AAT CAG AGG AGC TGA CAC CAG CGG TGG CCA AAG TGT AGG CTA CAA TAG

61    CCT CTT CCT CAT CTG ACT CCT CGG CGA TGG CCC GTA GGT CAT CCA CAC TAG GAG AGC AGA
                                          ORF1>

121   CTC TCA GAG GAT CGG CCC CCA GAA TGT ACT GGG CAA AGA CCT TCA TGC AGA TCT CCT CAA

181   TGC GGC GCT TCA TTA CAC TGA TAA CCT CAG GCT TGG TTA TCA GAG GCC GCT TGG CCA GCA

241   TCA CAC TAG TCT CCT CTA AGA CAT AGC AGC ACA GCA CCC GAC AGA ACT CAC TTA AGA GAG

301   AGA TGC CCC CGT ACA TGG TCA TCA TAC AAG CGT CAC TAG TGA CCT TGT ACT CAT TAC ACA

361   TTG TTT CCA CAC ATG TAG TGA GGA TAT CCA TAA ATA TGT GAT CAA TGT GCG TGA GCA CCT

421   TGT CTC TCT CCT CAT CCA AAA TCT TAA ATA TTT TCT GGG CAT AAG CCA TAA TCT CAT CAG

481   GGG AGC ACT GAG GCA AGT TCT GCA GTG CCG CCA TGG CCT GAC TGC AGC CAT TGG TGG TCT

541   TAG GGA AGG CTG AGT TCT TGG TAA AGA ACT CTA TAT TCC TGT AGC ACA TAT ACA TCA TCT

601   TTC TCC TAA GTT CAT CCT TTT TAG CAC GGG CCT TAG CCT GCA GTG CAC CCC CCA ACT TGT

661   TAG CGG CGC CCT TGC TCA CAT CAT GCA GCT CCT TAA TAC AAG CCA TCC ACA TCT CCC GCT

721   TAT CCT CAG GTA CAA TGT AGT TCT CAT ACA TGC TCT GCA TAG TTA GCC CAA TAC ACT TCA

781   TCT CCT CGA AAG GCT CAT GAA CCT TAT CTA AGA TAT CTA AGG CAT TCT GCA AAC ATC CTC

841   CCA TCA TAT TAA AGG CGC CAG TGA ATT TCT CTT CCG TCT GGG TAT ATT TTT TCA GCA TGT

901   GCT CCT TGA TTC TAT GCC GCA CCA TGT CCA CTC GAA CCT TAA TCT GTT TGA CTG TAG AGG

961   AGG ATA ACA ACA CAT ATA AGT ATC CGT CCT CCT GAC TCA TTT ATC GCT ATC TCG ATG CCC

1021  CGC TCA CAT GCA AGA GTT AAT CTT TAC TCT ATC TGA CAT ACA CAA GTA AAT CCA CGT CCC

1081  ATG CAG GTT AGT ATA CAT CAC ATA CAT GTC AAC AGA CTT ACC GAG TTC TGC AGG ACA TC
      ORF2>                            ORF3>

1141  TTT CTC GGG GTT CTC GTT GCA ATC CTC GGT CAC TTG TTC AAA AGT TTT GAG GGA TTC TTC

1201  GGC CAA CTC TGG AAA CAG CGG GTC TCC CAG ACT CAG CTG ACT GTT AAC CTC CTT CCT CAA

1261  CAT AGT CTG CAG GAA CGT CGT GGC CTT GGT CAC GGG TGT CTC GGG CCT AAA CAC ATG AGA
```

Fig. 19A

```
1321  AAT AGA GTC ATA AGC ACA TGG GTC ACA TAC AGG AGA TAT GTA TAT AAC ATT AAT ACA ATT

1381  TTA TTA AAA AAA AAG GGG GGG CAC AAA CCC CGA CAC GTA CCG TGG CAC CTT GGA GGA AGG

1441  GCC CTC GTC AGG ATT ATC AGG GTC CAT CTT TCT CTT GGC AGA GGA CTC CAT CGT GTC AAG

1501  GAC GGT GAC TGC AGA AAA GAC CCA TGG AAA GGA ACA GTC TGT TAG TCT GTC AGC TAT TAT
                                         ORF4>

1561  GTC TGG TGG CGC GCG CGG CAG CAA CGA GTA CTG CTC AGA CTA CAC TGC CCT CCA CCG TTA

1621  ACA GCA CCG CAA CGG GAG TTA CCT CTG ACT CTT ATC AGA ACA CAA CAA CTC AGC TGC CTG

1681  CAT CTT CTT CTG CCG CTG CCT TAA GTC TTC CAA ATG CGT CAG CGG TGC AAG CCC GCT CCC

1741  CGA GCT CAT TTT CAG ACA CAT ACC CTA CCG CCA CGG CCT TGT GCG GCA CAC TGG TGG TGG

1801  TGG GCA TCG TGC TGT GCC TAA GTC TGG CCT CCA CTG TTA GGA GCA AGG AGC TGC CGA GCG

1861  ACC ATG AGT CGC TGG AGG CAT GGG AGC AGG GCT CGG ATG TAG AAG CTC GCC GCC TAC GGC
                                     ORF5>

1921  AGA AGA GCC CAT GTC CGG AAC ACG TAC CCG AGA TTC GCG TGG AGA TCC CAC GTT ATG TTT

1981  AAT AAA AAC TGC GGG CAC TGG GGA CGG TGG TGT TGT ATA TGT GAA TTT GTA AAT AAT AAA

2041  TGA GAC CCC ATC CTG TA
```

Fig. 19B

SEQ ID NO:36  +1GTATCATATGCCAAGTACG...3' latent infection transcription start site 1 (LSS1), where +1 corresponds to nt 173,259 on the AD169 genome sequence SEQ ID NO:37  +1ATGCCCAGTACATGACCTT...3' latent infection transcription start site 2 (LSS2), where +1 corresponds to nt 173,195 on AD169.

SEQ ID NO:18  +1GTGACACCAGAGAAT...3' where +1 corresponds to nt 171,256 on AD169

SEQ ID NO:39  +1GACACCAGAGAAT...3'

SEQ ID NO:40  +1CCAGAGAAT...3'

SEQ ID NO:41  5'...ATAAATGAGACCCCATCCTGTA$_n$3' where the 3' proximal T corresponds to nt 173,331 on AD169

SEQ ID NO:42  5' TATTTACGGTAAACTGCCCACTTGGAGTACATCAAGT+1G 3'- latent infection transcription initiation region 1 (LSS1)

SEQ ID NO:43  5' TATTGACGTCAATGACGGTAAATGGCCCGCCTAGCATT+1A 3'- latent infection transcription initiation region 2 (LSS2)

SEQ ID NO:44  5' CGGGGACTCTGGGG+1GTGACACCAGAGAAT 3' antisense transcription initiation region and start aite SEQ ID NO:45  +1TCAGATCGCCTGGA...3' productive infection transcription start site (PSS)

SEQ ID NO:46  5' CCACGCGTCCTTTCAG/GTGATTATT...TCGTCTTCCTCCTGCAG/TTCGGCTTC... AAGATTGACGAG/GTGAGCCGCA...TTTCCCAAACAG/GTCATGGTGCG 3' Alternative exon 5 splice region site novel to the sense CLT (1.6/1.5 kb)

SEQ ID NO:47  5' CCACGCGTCCTTTCAAG/GTGATTATT...TTCCCAAACAG/GTCATGGTGCG 3' Alternative exon 5 splice region site novel to the sense CLT (1.3/1.2 kb)

SEQ ID NO:48  5'...TTTTTTTGTATCATATGCCAAGTCCG...3' 5' end sequence of pON2218 and pON2219

SEQ ID NO:49  5'...TTTTTTTGGTATCATATGCCAAGTCCG...3' 5' end sequence of pON2220

SEQ ID NO:50  5'...TTTTTTTATGCCCAGTACATGACCTT...3' 5' end sequence of pON2222, pON2223 and pON2224 at -292 (LSS2) relative to the PSS SEQ ID NO:51  5'...TTTTTTTGTGACACCAGAGAATCAGAGG...3' 3' end sequence of pON2227 and pON2228

SEQ ID NO:52  5'...TTTTTTTACCAGAGAATCAGAGG...3' 3' end sequence of pON2225

SEQ ID NO:53  5'...TTTTTTTGACACCATAGAATCAGAGG...3' 3' end sequence of pON2226

SEQ ID NO:54  5'...AAATAATAAATGAGACCCCATCCTGTAAAAAAA...3' 3' ends sequence of antisense transcripts of pON2229, pON2230, pON2231, pON2232

SEQ ID NO:55  5' TATAAGCAGAGCTCGTTTAGTGAACCG+1T 3'- Productive infection transcription initiation region (PSS).

Fig. 20

METHOD OF DETECTING CYTOMEGALOVIRUS (CMV)

This application is a division of application Ser. No. 08/450,945, filed May 23, 1995.

This work was supported in part by Public Health Service Grants SCOR HL33811 and RO1 AI33852. Accordingly, the United States Government has certain rights in this invention.

FIELD OF THE INVENTION

The present invention relates to diagnostic and therapeutic methods employing latent transcripts and promoters of human cytomegalovirus.

REFERENCES

Alford, C. A., and Britt, W. J., in THE HUMAN HERPESVIRUSES (Roizman, B., et al., Eds.), Raven Press, New York, N.Y., pp. 227–255 (1993).

Apperley, J. F., et al., *Experimental Hematology* 17:38–45 (1989).

Ausubel, F. M., et al., CURRENT PROTOCOLS IN MOLECULAR BIOLOGY (John Wiley and Sons, Inc., Media, Pa.).

Baines, P., et al., *Exp. Hematol.* 15:809–813 (1987).

Beames, et al., *Biotechniques* 11:378 (1991).

Bevan, I. S., et al., *Br. J. Haematol.* 78:94–99 (1991).

Bhaumik, D., et al., *J. Biol. Chem.* 269:15861–15867 (1994).

Boshart, M., et al., *Cell* 41:521–530 (1985).

Braun, R. W. and Reiser, H. C. *J. Virol.* 60:29–36 (1986).

Chee, M. S., et al., *Curr. Top Microbiol. Immunol.* 154:125–170 (1990).

Chirgwin, J. M., et al., *Biochemistry* 18:5294–5299 (1979).

Chomczynski, P., and Sacchi, N., *Anal. Biochem.* 162:156–159 (1987).

Gilliland, G., et al., *Proc. Natl. Acad. Sci. USA* 87:2725–2729 (1990).

Greenaway, P. J., and Wilkinson, G. W., *Virus. Res.* 7:17–31 (1987).

Guan, K. L. and Dixon, J. E., *Anal. Biochem.* 192:262 (1991).

Harlow, E., et al., ANTIBODIES: A LABORATORY MANUAL, Cold Spring Harbor Laboratory Press (1988).

Higchi, R., in PCR TECHNOLOGY: PRINCIPLES AND APPLICATIONS FOR DNA AMPLIFICATION, (Erlich, H. A., Ed.), Stockton Press, New York, N.Y., pp. 31–38 (1989).

Ho, M. in CYTOMEGALOVIRUS: BIOLOGY AND INFECTION, 2ND EDITION, Plenum Publishing Corp., New York, N.Y. (1991).

Ibanez, C. E., et al., *J. Virol.* 65:6581–6588 (1991).

Kondo, K., et al., *J. Gen. Virol.* 72:1401–1408 (1991).

Kyoizumi, S., et al., *Blood* 79:1704–1711 (1992).

Lathey, J. L. and Spector, S. A., *J. Virol.* 65:6371–6375 (1991).

Liebowitz, D., and Kieff, E., in THE HUMAN HERPESVIRUSES (Roizman, B., et al., Eds.), Raven Press, New York, N.Y., pp. 107–172 (1993).

Mocarski, E. S., in THE HUMAN HERPESVIRUSES (Roizman, B., et al., Eds.), Raven Press, New York, N.Y., pp. 173–226 (1993).

Mocarski, E. S., et al., *Proc. Natl. Acad. Sci. USA* 90:104–108 (1993).

Mullis, K. B., U.S. Pat. No. 4,683,202, issued Jul. 28, 1987.

Mullis, K. B., et al., U.S. Pat. No. 4,683,195, issued Jul. 28, 1987.

Namikawa, R., et al., *J. Exp. Med.* 172:1055–1063 (1990).

Ohara, O., et al., *Proc. Natl. Acad. Sci. USA* 86:5673–5677 (1989).

Plachter, B., et al., *Virology* 193:642–652 (1993).

Plotkin, S. A., et al., *J. Infect. Dis.* 159:860–865 (1989).

Porter-Jordan, K., et al., *J. Med. Virol.* 30:85–91 (1990).

Reilly, P.R., et al., BACULOVIRUS EXPRESSION VECTORS: A LABORATORY MANUAL, 1992.

Reiser, H., et al., *J. Gen. Virol.* 67:2595–2604 (1986).

Rice, G. P., et al., *Proc. Natl. Acad. Sci. USA* 81:6134–6138 (1984).

Roizman, B., and Sears, A. E., in THE HUMAN HERPESVIRUSES (Roizman, B., et al., Eds.), Raven Press, New York, N.Y., pp. 11–68 (1993).

Sambrook, J., et al., in MOLECULAR CLONING: A LABORATORYMANUAL, SECOND EDITION, Cold Spring Harbor Laboratory, Cold Spring Harbor, New York, N.Y. (1989).

Schrier, R. D., et al., *Science* 230:1048–1051 (1985).

Scott, D. M., et al., *J. Gen. Virol.* 70:685–694 (1989).

Simmons, P., et al., *Proc. Natl. Acad. Sci. USA* 87:1386–1390 (1990).

Sing, G. K. and Ruscetti, F. W., *Blood* 75:1965–1973 (1990).

Smith, D. B., et al., *Gene* 67:31 (1988).

Smith, P. K., et al., *Anal. Biochem.* 150:76 (1985).

Sorscher, D. H., et al., *Biochemistry* 33:11025–11032 (1994).

Spaete, R. R., and Mocarski, E. S., *Proc. Natl. Acad. Sci. USA* 84:7213–7217 (1987).

Stanier, P., et al., *Mol. Cell. Probes* 6:51–58 (1992).

Staprans, S. I., and Spector, D. H., *J. Virol.* 57:591–602 (1986).

Stenberg, R. M., et al., *J. Virol.* 49:190–199 (1984).

Stenberg, R. M., et al., *J. Virol.* 56:665–675 (1985).

Stenberg, R. M., et al., *J. Virol.* 63:2699–2708 (1989).

Stinski, M. F., *J Virol* 26:686–701 (1978).

Stinski, M. F., et al., *J. Virol.* 46:1–14 (1983).

Taylor-Wiedeman, J., et al., *J. Gen. Virol.* 72:2059–2064 (1991).

Taylor-Wiedeman, J., et al., *J. Virol.* 68:1597–1604 (1994).

Thomsen, D. R., et al., *Proc. Natl. Acad. Sci. USA* 81:659–663 (1984).

Woods, G. L., et al., *J. Virol. Methods* 18:207–213 (1987).

BACKGROUND OF THE INVENTION

Human cytomegalovirus (CMV), a ubiquitous species-specific herpesvirus and significant pathogen in immunocompromised individuals and neonates (Ho; Alford and Britt, 1993), is the best studied member of the betaherpesviruses (Morarski, 1993). Latent infection is a hallmark of all herpesviruses, and the neuronal site of latency of the alphaherpesviruses (such as herpes simplex virus-1) as well as the lymphoid site of latency of the gammaherpesviruses (such as Epstein-Barr virus) have been well-studied (Roizman and Sears, 1993; Liebowitz and Kieff, 1993).

However, although latent infection by CMV is widespread and reactivation of latent virus after either immunosuppression or progressive immunodeficiency is the single most important contributor to emergence of CMV disease, the site(s) of viral latency remain poorly characterized (Mocarski, 1993).

Viral DNA has been detected in peripheral blood cells of healthy seropositive carriers (Bevan, et al., Taylor-Wiedeman, et al., 1991), and monocytes have been implicated as the most likely cell type harboring latent viral genomes (Taylor-Wiedeman, et al., 1991). Although the CMV genome persists in monocytes, virus does not reactivate during cultivation under conditions that stimulate growth and differentiation (Taylor-Wiedeman, et al., 1994). Thus, it has remained unclear whether monocytes, or other mononuclear cell types in peripheral blood, correspond to true sites of latency or simply reflect an occasional depository of viral DNA during sporadic reactivation or persistent infection (Ibanez, et al., Lathey and Spector, Schrier, et al.).

Two well-studied human CMV (HCMV) strains—Towne and AD169—have been sequenced (Stenberg, et al., 1984; Stenberg, et al., 1985; Boxhart, et al., 1985; Stenberg, et al., 1989; Chee, et al., 1990).

SUMMARY OF THE INVENTION

The present invention includes a purified polypeptide that is (i) encoded by cytomegalovirus (CMV) DNA sequences and (ii) produced specifically during latent infection. In one embodiment, such polypeptides (herein referred to as latency-associated polypeptides) contain an amino acid sequence encoded by sequences derived from the CMV genomic region approximately 500 bp 5' to the CMV PSS ie1/ie2 transcription start site.

Further, a polypeptide of the present invention can be encoded by an RNA whose transcription start site is located within an approximately 500 base pair region of the CMV genome 5' to the PSS CMV ie1/ie2 transcription start site. In one embodiment, the transcription start site is contained within the ie1/ie2 enhancer region, for example, an RNA whose transcription start site is SEQ ID NO:36 or SEQ ID NO:37. Exemplary latency-associated polypeptides include, but are not limited to, SEQ ID NO:59, SEQ ID NO:61 and SEQ ID NO:63.

In a further embodiment, the polypeptide of the present invention is encoded by an RNA transcribed from the strand complementary to the coding strand (i.e., antisense) for CMV ie1/ie2 transcripts, where the location of said RNA overlaps introns 2 and 3 of the ie1/ie2 gene: the DNA sequence presented as SEQ ID NO:57 corresponds to one such RNA. Exemplary latency-associated polypeptides encoded by antisense transcripts include, but are not limited to SEQ ID NO:65, SEQ ID NO:67, SEQ ID NO:69, SEQ ID NO:71 and SEQ ID NO:73.

In addition, the polypeptides of the present invention include translation products derived from cytomegalovirus latency transcripts.

The present invention also includes methods for making the polypeptides of the present invention, such as, recombinant or synthetic production. Further, the invention includes vectors capable of expressing the latency-associated polypeptides in a selected host. Exemplary coding sequences for latency-associated polypeptides include, but are not limited to, SEQ ID NO:58, SEQ ID NO:60, SEQ ID NO:62, SEQ ID NO:64, SEQ ID NO:66, SEQ ID NO:68, SEQ ID NO:70 and SEQ ID NO:72.

In addition, the invention includes methods for detecting cytomegalovirus (CMV) in a sample, particularly for detecting a latent CMV infection. In one such method, the sample contains an antibody that is immunoreactive with a latency-associated polypeptide. The sample is brought into contact with a latency-associated polypeptide of the present invention. The antibody binds to the latency-associated polypeptide. The binding is detected and indicates the presence of CMV in the sample, more particularly, the presence of a latent CMV infection associated with the sample. Source samples include, for example, human serum or plasma. The detection of binding of the antibody to antigen (i.e., latency-associated polypeptide) can be carried out in several ways including by ELISA (e.g., an antibody capture assay where the antigen is fixed to a solid support and detection of the bound antibody is carried out by exposing the antigen/antibody complex to a detector antibody, for example, a labelled anti-human antibody). Alternatively, detection can be carried out by Western blot analysis where the antigen or antigens are size-fractionated on a gel, transferred to a membrane and the membrane exposed to the sample being tested. Detection of the bound antibody can carried out by exposing the antigen/antibody complex to a detector antibody, for example, a labelled anti-human antibody.

The invention also includes a method of detecting cytomegalovirus (CMV) in a sample employing anti-latency-associated-polypeptide antibodies. In this method, a sample containing a latency-associated polypeptide is contacted with an antibody, where the antibody is immunoreactive with the latency-associated polypeptide. The binding of the antibody to the latency-associated polypeptide antigen is then detected and is indicative of the presence of CMV in the sample. Detection of the binding of the antibody to the polypeptide can be carried out in a number of ways including, Western blotting and antigen capture assays.

For Western blot analysis, the sample is typically size fractionated on a gel, transferred to a membrane, and exposed to the antibody. Binding of the antibody to the antigen can be detected directly (e.g., by labelling the antibody) or indirectly (e.g., using a second antibody to detect the presence of the first).

Antigen capture assays typically include attachment of the antibody (specifically immunoreactive with a selected latency-associated polypeptide) to a solid support and detection of antigen bound to the solid support. Detection can be carried out, for example, by using a second, reporter antibody that is specifically immunoreactive with the selected latency-associated polypeptide. Alternatively, binding of the antigen can be detected using competition assay that employs a polypeptide-reporter complex, where the polypeptide competes with binding of the polypeptide-reporter complex to the antibody.

Samples that can be analyzed using the methods just described include human tissue samples such as bone marrow, hematopoietic stem cells, blood or plasma samples.

The present invention also includes monoclonal and polyclonal antibodies (and preparations thereof, for example, IGG preparations) that are specifically immunoreactive with the latency-associated polypeptides of the present invention.

In another aspect, the invention includes a method of detecting latent cytomegalovirus (CMV) infection of a sample containing RNA. In this method, cDNA is generated specifically from RNA in the sample (for example, the RNA may be purified or the DNA in the sample may be degraded). The cDNA is then amplified by polymerase chain reaction using a primer set, consisting of two primers, where the primers define a selected CMV region that encodes an RNA (or portion thereof) produced specifically during latent infection. The presence of amplification products that correspond to selected CMV region is indicative of latent CMV infection of the sample.

One such region is the CMV genomic region located 5' to the CMV PSS ie1/ie2 transcription start site (FIG. 11). In one embodiment of the method, at least one primer of the primer set is selected from the CMV sequences located 5' to the CMV PSS ie1/ie2 transcription start site. In another embodiment, at least one primer of the primer set is complementary to the coding strand for CMV ie1/ie2 transcripts, where said amplification products overlap introns 2 and 3 of the ie1/ie2 gene.

In yet another aspect the invention includes an expression vector useful for transfection of mammalian cells, particularly of hematopoietic stem cells. The vector includes an expression cassette which comprises (i) a promoter that promotes the transcription of RNA transcripts from the cytomegalovirus genome specifically during latent infection (i.e., relative to productive infection), and (ii) a coding sequence that is heterologous to the promoter. The coding sequence is operably linked to the promoter and can encode products including, but not limited to, polypeptides and RNA products (e.g., antisense RNA or ribozymes).

The expression cassette can be carried in any number of vectors useful for the transfection of mammalian cells, including modified forms of cytomegalovirus itself.

In one embodiment, the promoter sequences include a promoter whose RNA transcription start site is located within an approximately 500 base pair region of the CMV genome 5' to the PSS CMV ie1/ie2 transcription start site. In another embodiment, the promoter includes the sequence presented as SEQ ID NO:42. In yet another embodiment, the promoter includes the sequence presented as SEQ ID NO:43. In addition, the promoter sequences include a promoter whose RNA is transcribed from the strand complementary to the coding strand for CMV ie1/ie2 transcripts, where the transcribed RNA overlaps the regions of the CMV genome corresponding to introns 2 and 3 of the ie1/ie2 gene. In one embodiment, such a promoter includes a portion of the sequence presented in SEQ ID NO:44.

The expression vectors of the present invention can be used in a method of producing stably transformed mammalian cells, particularly, hematopoietic stem cells. In the method, the expression vector is transfected into the cells and the cells are propagated or maintained.

The present invention also includes gene therapy applications using the vectors of the present invention. One embodiment of the invention is a method for remedying genetic defects in target cells. Such defects include disease states caused by viral infection or inappropriate expression of cellular genes (e.g., deficiencies and over-expression). In this method, an expression vector is prepared as described above. The expression vector is then introduced into a target cell, such as a human hematopoietic stem cell. The target cells may be (i) in a living animal, or (ii) cells that are maintained in vitro that will be re-introduced into a host animal.

The present invention also includes pharmaceutical compositions of the above described vectors, such as compositions suspended in a pharmaceutically acceptable carrier.

These and other objects and features of the invention will be more fully appreciated when the following detailed description of the invention is read in conjunction with the accompanying drawings.

BRIEF DESCRIPTION OF THE FIGURES

FIG. 3A shows ethidium bromide stained bands, and FIG. 3B shows autoradiographic results of hybridization with $^{32}$P dCTP-labeled $\beta_{2.7}$ DNA probe.

FIG. 4A shows ethidium bromide stained bands, and FIG. 4B shows autoradiographic results of hybridization with $^{32}$P dCTP-labeled UL112/113 DNA probe.

FIG. 7 shows the names, sequences and SEQ ID NOs of the PCR primers used in experiments described herein.

FIGS. 18A and 18B show the spliced nucleotide sequence corresponding to sense transcripts, with PSS, LSS1, LSS2 indicated by italics, and ORFs labeled and indicated by an underlined initiation "<u>ATG</u>" codon.

Figure 1:
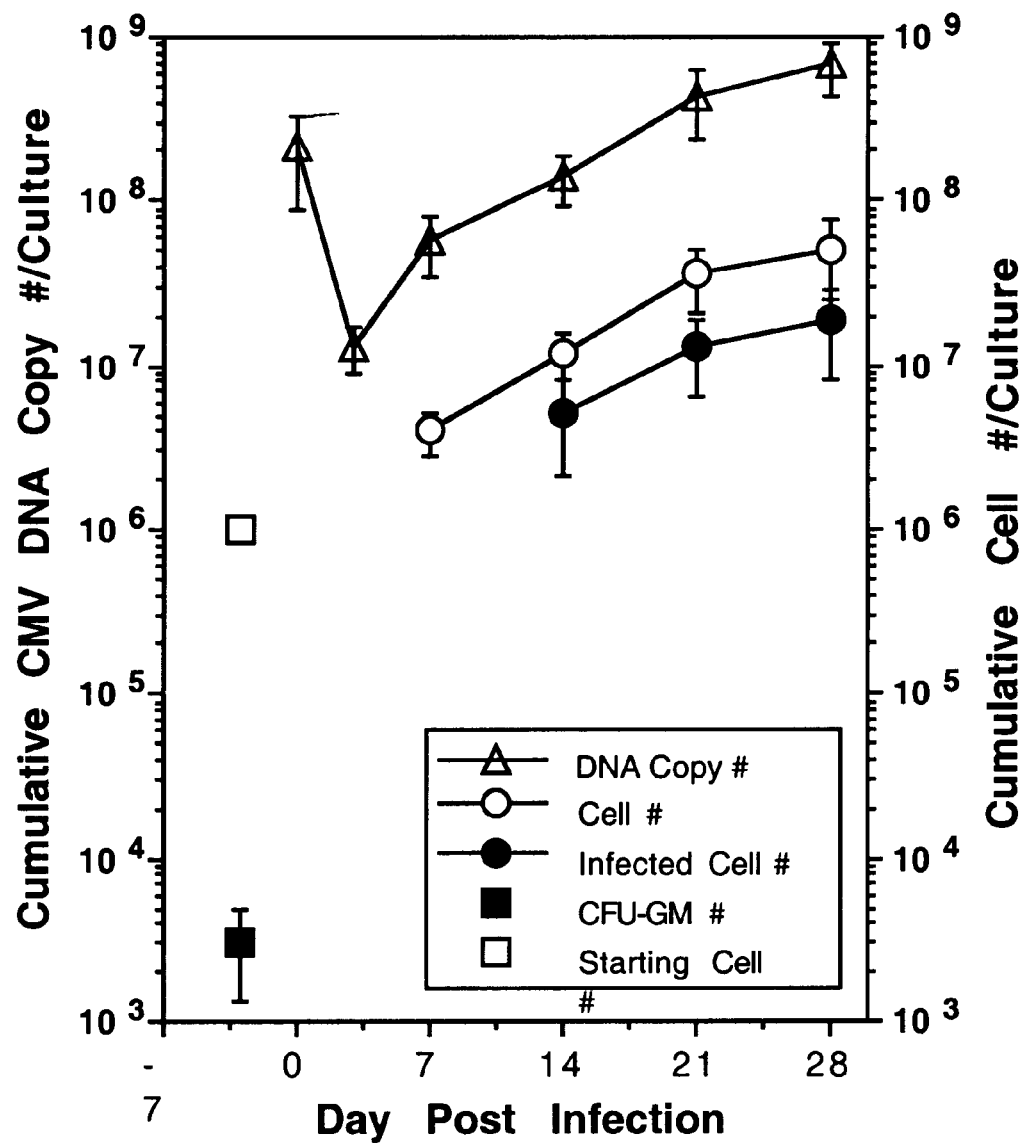
FIG. 1 shows a graph illustrating maintenance of human CMV DNA in GM-P cultures as a function of time.

FIGS. 19A and 19B show the nucleotide sequence corresponding to antisense transcripts, with ORFs labeled and indicated by an underlined initiation "<u>ATG</u>" codon.

FIG. 20 shows partial sequences of CMV regions related to the latent transcripts of the present invention.

DETAILED DESCRIPTION OF THE INVENTION

I. Definitions

Two nucleic acid elements or fragments are said to be "heterologous" if the elements are derived from two different genes, or alternatively, two different species. For example, a human gene encoding a protein having therapeutic utility in granulocytes, monocytes or macrophages is heterologous to a promoter from human cytomegalovirus.

II. Overview of Invention

Experiments performed in support of the present invention and detailed herein demonstrate that bone marrow is a natural site of human CMV viral latency and latent gene expression. The experiments employed cultured primary granulocyte-macrophage progenitors (GM-Ps), which were derived from human fetal liver and bone marrow hematopoietic cells able to maintain a $CD14^+$, $CD15^+$, $CD33^+$ phenotype during propagation in culture. After exposure to CMV, viral DNA persisted in a high proportion of GM-Ps in the absence of delayed early (β) gene expression during a four week period of culture. Although infection was highly restricted, virus was reactivated by prolonged co-cultivation of infected GM-Ps with permissive cells.

Results of the experiments indicate that transcription in latently-infected GM-Ps was restricted. ie1/ie2 region transcripts were characterized using RT-PCR analysis with specific primers in conjunction with 3' and 5' RACE mapping. Transcripts were detected arising from both DNA strands (sense and anti-sense relative to transcripts detected in permissive cells). A 2.1 kb nonspliced antisense transcript was characterized by cDNA cloning and mapping. The 5' end of the antisense transcript was located on the strand opposite ie1 exon 4 and the 3' (polyadenylated) end was located on the strand opposite the intron between exons 1 and 2.

Sense transcripts originated from two novel start sites located 292 and 354 base pairs (bp) upstream of the ie1/ie2 start site used during productive infection (in a region referred to as the 'enhancer'). Mapping and cDNA cloning identified a number of differentially spliced products through the ie1 and ie2 regions. This information was used to assess the presence of latent transcripts in bone marrow samples from 13 donors without prior knowledge of their serological status. Sense ie1/ie2 region transcripts were detected by RT-PCR in 5 of 7 seropositive, but in none of six seronegative donors. Antisense transcripts were detected in a subset of these individuals, but transcripts from other regions were not detectable.

The results of these experiments indicate that bone marrow is a site of natural latent infection, and that novel latent transcripts encoded from the ie1/ie2 region are an indicator of, and may function in latent infection. Further, the results indicate that the ie1/ie2 region contains promoters capable of driving the expression of the latent transcripts. Such promoters maybe useful, as described below, in gene therapy applications where it is desired to target cells derived from the GM-P progenitors.

Prior to the guidance presented herein, there was no clear information on the type(s) or extent of viral gene expression in latently-infected tissue, and it was not clear whether or not bone marrow could be a site of latent infection. The site(s) of CMV latency and detection of latent transcripts in humans were not understood prior to the experiments described herein. Results of these experiments provide evidence for a specific set of transcripts and constitute unambiguous evidence supporting the role of bone marrow hematopoietic progenitor cells in CMV latency.

The transcripts (and associated promoter elements) identified herein are in the region of the major viral regulatory genes, and comprise latent transcripts expressed in the same orientation ("sense" on the viral genome) as well as in the opposite ("antisense") direction. The CMV promoter-enhancer that directs the expression of the principle viral regulatory genes ("the CMV enhancer-promoter") is in this region, although it is not active in the GM-Ps. Promoters silent during productive replication are active during latency and are responsible for the transcription of sense transcripts. These promoters are located 292 and 356 bp upstream of the well-characterized CMV promoter-enhancer active during replication.

The results summarized above also have implications for diagnostic and therapeutic methods relating to CMV. Diagnostic methods (such as RT-PCR or assays employing antibodies directed against expressed latent transcripts) may be employed for the detection of latently infected individuals and for assaying human blood and tissue products for the presence of CMV (to reduce the risk of transmitting CMV-related disease). Therapeutic methods include gene therapy approaches, where latency-specific genes are expressed constitutively in long-lived or self-renewing cell lineages, and their regulatory elements are employed for expression of foreign genes.

The latent transcripts described herein, as well as polypeptides encoded by spliced transcripts, may be used to detect presence of CMV infection in blood or a tissue for transplantation. The latent transcript polypeptides may also be employed in vaccine formulations to protect against CMV infection. The latency promoters may be employed for gene therapy (e.g., in hematopoietic cells). Because the infection of hematopoietic cells is quiescent, CMV may be used as a vector in these cells with a foreign gene encoded by a latent promoter.

III. Summary of Experiments

Results of experiments performed in support of the present invention suggest that the CMV genome is maintained in GM-Ps in the absence of productive viral replication. When cells were maintained in the presence of ganciclovir at concentrations of this drug known to inhibit productive viral replication (5 or 10 μM), GM-P cell number increased between 3- and 10-fold over a period of two weeks, and viral genome copy increased proportionately. No differences in morphology or cell growth characteristics were observed in infected cultures when compared to uninfected controls. A low passage strain of CMV, Toledo, which had been found to be more virulent than Towne strain in human volunteers (Plotkin, et al.), gave similar results to those described for the Towne strain derivative, RC256. An additional 19 individual samples of fetal liver and three samples of fetal bone marrow cells were tested in this system using either strain of virus and results consistent to those described here were obtained.

Prior to the teachings presented herein, there was little if any information on the nature or expression of the latent CMV genome. Unlike the neuronal site that characterizes latency of alphaherpesviruses such as herpes simplex virus, or the B lymphocyte that is clearly important for latency of the gammaherpesvirus, Epstein-Barr virus, the site of human CMV latency has been elusive. Despite the fact that sensitive PCR methods have reproducibly shown association of the viral genome with mononuclear leukocytes (Taylor-Wiedeman, et al., 1991), the absence of a manipulable system to reactivate virus has limited any understanding of these cells as site of latent infection.

The results of experiments presented herein demonstrate CMV persistence in human bone marrow-derived GM-Ps, and experimental reactivation of the virus. This virus interaction with GM-Ps is characterized by restricted viral gene expression and an atypical, unspliced ie1 transcript. Following the teachings herein, expression of this transcript can now be evaluated directly in healthy carriers.

The ability to recover virus after extended cocultivation with permissive cells indicates that CMV replication in GM-Ps is dependent upon growth or differentiation that occurs during cocultivation, consistent with previous studies of the dependence of CMV replication on cell type and on the differentiation state of cells (Taylor-Wiedeman, et al., 1994, Ibanez, et al., Lathey and Spector, Reiser, et al., Apperley, et al., Simmons, et al., Sing & Ruscetti).

The system described herein enables the investigation of interactions of CMV with primary myelomonocytic cells, which constitute a potential reservoir of latent CMV in healthy carriers (Taylor-Wiedeman, et al., 1991). It is now possible to investigate viral and host cell functions in establishment, maintenance and reactivation of latent infection. Furthermore, the system described herein enables the direct investigation of the atypical ie1 transcripts in latent infection.

Interestingly, CMV gene expression was highly restricted in both the large adherent cells that were generated during culture, as well as in the nonadherent GM-Ps. The presence of the virus in these cultures had no detectable impact on the growth or differentiation of cells in these cultures.

The teachings herein also establish that both low and high passage laboratory strains of CMV retain the biological potential for latent infection of GM-Ps. Virus latency in these cells is associated with the stable association of viral DNA with cells, and with a ganciclovir-resistant parallel increase in viral DNA along with cell number. The results of experiments performed in support of the present invention suggest a mechanism for maintaining the viral genome in latently-infected GM-Ps that is distinct from that used during productive replication. The detection of atypical ie1 region transcripts suggests that the products may play a role in latent infection and in genome maintenance.

The interaction of CMV with GM-Ps in vivo may explain the detection of viral DNA in mononuclear cells from the peripheral blood normal healthy seropositive individuals (Taylor-Wiedeman, et al., 1991; Stanier, et al., 1992; Bevan, et al., 1991) and the presence of infectious virus in monocytes and granulocytes of immunocompromised individuals. Prior to the present disclosure, evaluation of viral gene expression in normal healthy seropositive individuals has been limited and has led to mutually incompatible conclusions. Whereas detection of CMV α (immediate early) gene transcripts by in situ hybridization (Schrier, et al., 1985) suggested ongoing expression, more recent analyses have suggested CMV gene expression can only be detected following cell differentiation (Taylor-Wiedeman, et al., 1994).

Experiments performed in support of the present invention have characterized two novel classes of CMV latent transcripts (CLTs), encoding latency-associated polypeptides, expressed in cultured GM-Ps. These transcripts were also detected in the bone marrow of healthy CMV seropositive adults.

Sequence analysis revealed the presence of novel open reading frames (ORFs) greater than 40 codons on latent transcripts (FIGS. 10A–10K) that would not be present on transcripts initiating at PSS, the transcription initiation site used during productive infection (FIGS. 10A–10K). Two different short ORFs (SEQ ID NO:58, encoding 45 amino acids (SEQ ID NO:59); and SEQ ID NO:60, encoding 42 amino acids (SEQ ID NO:61)) were 5'-proximal on the sense transcripts initiating at LSS1 or LSS2 and one longer ORF (SEQ ID NO:62, encoding 94 amino acids (SEQ ID NO:63)), corresponding to the amino terminal 59 codons of UL126 (Chee, et al., 1990), was positioned downstream of the shorter ORFs. The 94 codon ORF (SEQ ID NO:62) crossed the exon 1/2 and 2/3 boundaries in a different ORF than the proteins associated with productive infection.

The presence of the novel ORFs is expected to down-regulate expression of downstream ORFs, including the well-characterized 491 and 579 aa proteins encoded by the ie1 and ie2 genes during productive infection (Stenberg, et al., 1984; Stenberg, et al., 1995; Stenberg, et al., 1989; Stinski, et al., 1983; Stinksi, et al., 1978). Consistent with this prediction, expression of the 491 aa IE1 or the 579 aa IE2 proteins was not detected by immunofluorescence analysis with CH160, a murine monoclonal antibody specific for an epitope in exon 2 (Plachter, et al., 1993).

Five ORFs were identified in the antisense transcript. The are presented herein as (i) SEQ ID NO:64, which encodes 59 amino acids (SEQ ID NO:65); SEQ ID NO:66, which encodes 154 amino acids (SEQ ID NO:67); SEQ ID NO:68, which encodes 44 amino acids (SEQ ID NO:69); SEQ ID NO:70, which encodes 152 amino acids (SEQ ID NO:71); and SEQ ID NO:72, which encodes 50 amino acids (SEQ ID NO:73). The 152 codon ORF (SEQ ID NO:71) corresponded to UL124 (Chee, et al., 1990). The polypeptides encoded by the novel ORFs exhibited little similarity to other predicted proteins currently deposited in sequence databases.

The results of experiments detailed herein have established that the latent CMV genome resides in bone marrow (BM)-derived hematopoietic cells and that latency is associated with the expression of novel transcripts. The data further suggest that latent transcripts, particularly sense transcripts readily detected in more than 70% of seropositive BM donors, may play an important role during latency. The identification of CLTs enables a detailed evaluation of CMV latency and reactivation, and allows the characterization of virus and host cell functions necessary for these processes. Because the interaction of CMV with GM-Ps is non-cytocidal, the latency-specific promoters described herein may be employed in gene therapy applications to control the expression of heterologous genes.

IV. Applications/Utility

A. Production of Recombinant Polypeptides

CMV latency-associated-polypeptide encoding polynucleotide sequences, or CLTs, may be cloned into suitable recombinant expression vectors and used to express latency-associated polypeptides in selected host cells, such as *E. coli*. Such vectors typically contain control sequences, such as sequences containing promoter regions, enhancer elements, and the like, which are compatible with the selected host cell. These control sequences are operably linked to the insert sequence (i.e., latency-associated polypeptide coding sequences) such that the insert sequence can be expressed in the selected host cell. Exemplary coding sequences include, but are not limited to, sequences encoding the following polypeptides: SEQ ID NO:59, SEQ ID NO:61, SEQ ID NO:63, SEQ ID NO:65, SEQ ID NO:67, SEQ ID NO:69, SEQ ID NO:71 and SEQ ID NO:73. Exemplary DNA sequences include, but are not limited to, SEQ ID NO:58, SEQ ID NO:60, SEQ ID NO:62, SEQ ID NO:64, SEQ ID NO:66, SEQ ID NO:68, SEQ ID NO:70 and SEQ ID NO:72.

One example of an expression vector for recombinant production of latency-associated polypeptides is the plasmid pGEX (Smith, et al., 1985, 1988) and its derivatives (e.g., the pGEX series from Pharmacia Biotech, Piscataway, N.J.). These vectors express the polypeptide sequences of a cloned insert fused in-frame with glutathione-S-transferase. Recombinant pGEX plasmids can be transformed into appropriate strains of E. coli and fusion protein production can be induced by the addition of IPTG (isopropyl-thio galactopyranoside). Solubilized recombinant fusion protein can then be purified from cell lysates of the induced cultures using glutathione agarose affinity chromatography according to standard methods (Ausubel, et al.).

Alternatively, affinity chromatography may also be employed for isolating β-galactosidase fusion proteins, such as those produced by cloning latency-associated polypeptide sequences in lambda gt11. The fused protein is isolated by passing cell lysis material over a solid support having surface-bound anti-β-galactosidase antibody.

DNA encoding a latency-associated polypeptide can be cloned into any number of commercially available vectors to generate recombinant latency-associated polypeptides in the appropriate host system. These systems include a number of bacterial expression vectors, such as lambda gt11 (Promega, Madison Wis.), pGEX (Smith, et al.), and pBS (Stratagene, La Jolla Calif.) vectors; yeast expression systems, such as the Pichia expression kit from Invitrogen (San Diego, Calif.); baculovirus expression systems (Reilly, et al.; Beames, et al.; Clontech, Palo Alto Calif.); and mammalian cell expression systems (Clontech, Palo Alto Calif.; Gibco-BRL, Gaithersburg Md.).

A number of features can be engineered into the expression vectors, such as leader sequences which promote the secretion of the expressed sequences into culture medium. The recombinantly produced polypeptides are typically isolated from lysed cells or culture media.

Isolated recombinant polypeptides produced as described above may be purified by standard protein purification procedures, including differential precipitation, molecular sieve chromatography, ion-exchange chromatography, isoelectric focusing, gel electrophoresis and affinity chromatography. Protein preparations can also be concentrated by, for example, filtration (Amicon, Danvers, Mass.).

In addition to recombinant methods, latency-associated proteins or polypeptides may be chemically synthesized using methods known to those skilled in the art. Latency-associated polypeptides of the present invention may be used in a number of applications, including vaccines and diagnostic applications (e.g., as described below).

B. Diagnostic Methods and Kits

The latency-associated polypeptides of the present invention are advantageous for use as diagnostic agents to detect the presence of latent CMV infection. The ability to diagnose such a latent infection may be significant for several reasons. For example, it is known that approximately 80% of the adult population has serum antibodies directed against CMV proteins produced during active virus infection (i.e., 80% of the population is seropositive). In healthy individuals, CMV infection typically produces no symptoms. In contrast, immunocompromised individuals, such as the elderly and those with AIDS, as well as neonates are prone to serious complications arising from CMV infections. Accordingly, transplant tissues and transfusion products (e.g., blood), are typically screened for the presence of anti-CMV antibodies to identify tissue samples not suitable for immunocompromised individuals.

It is known that the presence of anti-CMV antibodies in a tissue donor does not necessarily indicate that virus is present in the donated tissue. In fact, it has been suggested that only approximately 5–12% of the blood from CMV-positive individuals actually contains the virus. Accordingly, there is a need for more predictive tests of CMV infection risk from transplant tissues (e.g., bone marrow) or transfusion products (e.g., blood, plasma, etc.) than are currently available.

Methods of the present invention may be employed in such tests. It is contemplated that the presence of latent CMV transcripts, latency-associated polypeptides and/or antibodies directed against such polypeptides is indicative of virus that has an increased probability of reactivating. Accordingly, transplant tissues may be subject to a differential screen for CMV. For example, serum samples may initially be tested for the presence of anti-CMV antibodies using known methods. Those samples testing positive may then be subjected to a secondary screen, employing methods of the present invention, to test for the presence of latent CMV transcripts, polypeptides, or antibodies directed against such latency-associated polypeptides. Samples testing positive for evidence of latency-associated CMV transcripts may be designated as more likely to transmit the CMV virus, and be handled and treated accordingly.

One method of detecting or diagnosing latency-associated CMV transcripts, or CLTs, is RT-PCR, as detailed in the Examples below. RT-PCR has an advantage over DNA PCR in that it typically yields more reproducible and informative results, in part because a cell typically contains many transcripts for each copy of DNA. Further, the presence of transcripts is an indicator of transcriptional activity, which is more informative than the detection of a (potentially quiescent) segment of DNA.

In another diagnostic configuration, the present invention includes an antibody capture assay where a serum contains antibodies directed against at least one latency-associated polypeptide. In this embodiment, a test sample (e.g., serum or plasma) is reacted with a solid phase reagent having a surface-bound latency-associated polypeptide (obtained by the methods of the present invention, for example, SEQ ID NO:63 or SEQ ID NO:67). After binding anti-latency-associated-polypeptide antibody to the reagent and removing unbound serum components by washing, the reagent is reacted with reporter-labeled anti-human antibody to bind reporter to the reagent in proportion to the amount of bound anti-latency-associated-polypeptide antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric or calorimetric substrate.

The solid surface reagent in the above assay is prepared by known techniques for attaching protein material to solid support material, such as, polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group.

In a second diagnostic configuration, known as a homogeneous assay, antibody binding to a solid support produces some change in the reaction medium which can be directly detected in the medium. Known general types of homogeneous assays proposed heretofore include (a) spin-labeled reporters, where antibody binding to the antigen is detected by a change in reported mobility (broadening of the spin splitting peaks), (b) fluorescent reporters, where binding is detected by a change in fluorescence efficiency, (c) enzyme reporters, where antibody binding effects enzyme/substrate interactions, and (d) liposome-bound reporters, where binding leads to liposome lysis and release of encapsulated reporter. The adaptation of these methods to the protein antigen of the present invention follows conventional methods for preparing homogeneous assay reagents.

In each of the assays described above, the assay method involves reacting the serum from a test individual with the protein antigen and examining the antigen for the presence of bound antibody. The examining may involve attaching a labeled anti-human antibody to the antibody being examined and measuring the amount of reporter bound to the solid support, as in the first method, or may involve observing the effect of antibody binding on a homogeneous assay reagent, as in the second method.

Also forming part of the invention is an assay system or kit for carrying out the assay method just described. The kit generally includes a support with surface-bound latency-associated polypeptide antigen, which is, for example, recombinantly produced.

In one apsect, the present invention includes antibodies specific against the latency-associated polypeptides of the present invention. The polypeptides, or immunogenic portions thereof, can be used as antigens in the generation of anti-sera or antibody preparations. Typically, to prepare antibodies, a host animal, such as a rabbit, is immunized with the purified antigen or fused protein antigen. The host serum or plasma is collected following an appropriate time interval, and this serum is tested for antibodies specific against the antigen.

Example 14 describes the production of rabbit serum antibodies which are specific against latency-associated polypeptides in Sj26 and beta-galactosidase fusion proteins. These techniques are equally applicable to the other latency-associated antigens of the present invention.

The gamma globulin fraction or the IgG antibodies of immunized animals can be obtained, for example, by use of saturated ammonium sulfate or DEAE Sephadex, or other techniques known to those skilled in the art for producing polyclonal antibodies.

Alternatively, a purified latency-associated antigen or fused antigen protein may be used for producing monoclonal antibodies. Here the spleen or lymphocytes from an immunized animal are removed and immortalized or used to prepare hybridomas by methods known to those skilled in the art (e.g., Harlow, et al.).

Antibodies secreted by the immortalized cells are screened to determine the clones that secrete antibodies of the desired specificity, for example, using Western blot analysis.

A third diagnostic configuration involves use of the anti-latency-associated-polypeptide antibodies. The presence of latency-associated polypeptides may be detected in a sample, for example, using an antigen capture assay where latency-associated polypeptide antigens present in candidate samples are reacted with an latency-associated-polypeptide specific monoclonal or polyclonal antibody.

In this embodiment, the antibody is bound to a solid substrate-and then exposed to the sample. Such samples include, but are not limited to, bone marrow samples, tissue samples, blood samples, and homogenates thereof. Binding of a latency-associated polypeptide antigen to the antibody/substrate is then detected by binding a second, labelled anti-latency-associated-polypeptide antibody.

Antibodies for use in this aspect of the present invention can be prepared, as described above, utilizing the peptides of the present invention. Particularly useful in the practice of this aspect of the invention are two or more monoclonal antibodies raised against the same latency-associated polypeptide. Alternatively, a preparation of polyclonal antibodies might be used for capturing the latency-associated polypeptide antigen and presence of the antigen may be detected using a labeled monoclonal antibody.

Alternatively, an antigen competition assay can be used to detect the binding of specific antigens to an antibody. Briefly, anti-latency-associated-polypeptide antibody molecules are isolated (e.g., a monoclonal antibody or IGG from a rabbit anti-latency-associated-polypeptide polyclonal antibody serum). Microwells are coated with the antibody and the antibody coated wells are then incubated with the test samples. After incubation, a polypeptide-reporter complex is added to each well. The polypeptide-reporter complex comprises a reporter moeity, such as, horse radish peroxidase conjugated to the latency-associated polypeptide that was used to generate the antibody that was bound to the well. After washing the well the presence of bound polypeptide-reporter complex is detected by addition of a calorimetric substrate. The presence of a latency-associated polypeptide in the test sample is identified by color diminution due to successful inhibition of binding of the polypeptide-reporter complex. The concentration of the latency-associated polypeptide in the sample can be determined by reference to a standard linear inhibition curve established for the assay using varied known amounts of latency-associated polypeptide and a constant amount of polypeptide-reporter complex.

Also forming part of the invention are assay systems or kits for carrying out the diagnostic methods described above.

C. Screen for Compounds that Induce Latency

LSS1 and LSS2 promoter regions include sequences just upstream of the site (+1) of transcription initiation (i.e., SEQ ID NO:42 and SEQ ID NO:43, respectively). The promoter regions may be further characterized by deletion analysis to identify additional sequences controlling the level of transcription. Sequences containing desired promoter regions may then be used in a number of applications.

For example, LSS1 and/or LSS2 promoter sequences may be employed in screens to identify compounds effective to upregulate the promoters. As described above, the presence of the latent ORFs is expected to down-regulate expression of downstream ORFs. Though not wishing to be bound by a particular mechanism, it is contemplated that such down-regulation may be effective to induce latency in active virus. Accordingly, compounds which upregulate latent CMV promoters, such as LSS1 and LSS2 promoters, may be effective as anti-viral compounds that inhibit active HCMV.

A screen effective to identify such compounds is as follows. A selected CMV latent promoter is cloned into a reporter gene construct, such as a CAT construct, which is transfected into host cells permissive for the promoter (e.g., GM-P cells). The cells are contacted with a test compound and assayed for reporter gene expression. Compounds which upregulate the level of reporter expression are identified as effective to promote transcription of CMV latent transcripts.

D. CMV Latent Promoters in Gene Therapy

CMV latent promoters of the present invention may be employed in gene therapy applications, particularly applications targeting granulocyte-macrophage progenitors. These cells comprise a self-renewing population of cells, and include CD34+ and CD33+ cell types (CD34+ is the earliest lineage marker know for bone marrow-derived hematopoietic cells). The latent promoters described above appear to be specific for expression in the early stage granulocyte-macrophage lineage.

The promoters are engineered into expression vectors suitable for delivery of genes (somatic gene therapy) to blood cells. The promoters described above (sense transcript promoters driving expression from LSS1 and LSS2 and/or the antisense transcript promoter) can be inserted into a variety of vectors (e.g., retrovirus, adenovirus, parvovirus, cytomegalovirus-derived vectors) to confer upon these vectors the ability to express a heterologous gene in granulocyte-macrophage progenitors. The vectors may then be used to deliver the heterologous genes to granulocyte-macrophage progenitors to treat diseases which affect cells derived from granulocyte-macrophage progenitors, including neutrophils, eosinophils, basophils, monocytes and macrophages.

Since cells derived from granulocyte-macrophage progenitors are typically circulating blood cells, chimeric vectors (containing a CMV latent promoter operably-linked to a heterologous gene) of the present invention may be used to express secreted proteins useful in the treatment of any diseases amenable to therapy by blood-borne polypeptide therapeutics (e.g., Gautier's disease). Stem cells such as granulocyte-macrophage progenitors offer distinct advantages for this type of gene therapy, since they can provide a steady supply of differentiated circulating cells.

The following examples illustrate but in no way are intended to limit the present invention.

MATERIALS AND METHODS

Unless otherwise indicated, restriction enzymes and DNA modifying enzymes were obtained from New England Biolabs (Beverly, Mass.) or Boehringer Mannheim (Indianapolis, Ind.). Other chemicals were purchased from Sigma (St. Louis, Mo.) or United States Biochemical (Cleveland, Ohio).

A. Cell and Virus Culture

Fetal liver cells (from 12 to 18 week abortuses) were cultured in Iscove's modified Dulbecco's medium (GIBCO/BRL, Grand Island, N.Y.) supplemented with 5% fetal bovine serum (FBS), 5% conditioned medium from the 5637 bladder carcinoma cell (American Type Culture Collection (ATCC) line HTB9; Rockville, Md.), 100 units/ml of penicillin G and 100 μg/ml of streptomycin (Baines, et al.). Nonadherent cells were collected and transferred three times a week, depleting cultures of stromal cells and more differentiated, adherent myelomonocytic lineage cells. Human foreskin fibroblast (HF) cells were grown in Dulbecco's modified Eagle's medium (GIBCO/BRL) supplemented with 10% "NUSERUM" (Collaborative Research, Bedford, Mass.). The lacZ derivative of human CMV strain Towne, RC256 (Spaete & Mocarski), and low passage isolate Toledo (Plotkin, et al.) were propagated on HF cells.

B. Detection of viral infectivity

Three freeze/thaw (F/T) cycles (−80° C./37° C.) were used in attempts to release virus from $10^5$ GM-Ps. Plaque assay was on HF cells and included centrifugal enhancement at the time of inoculation (Woods, et al.). Infected GM-Ps were introduced into HF cell cultures in attempts to recover virus by cocultivation.

C. Nested DNA PCR and Cell Dilution

Cells or nuclei were counted and diluted to give an average of 100, 30, 10, 3 and 1 per tube, and DNA was extracted as previously described (Kondo, et al., 1991). Nuclei were prepared from cells lysed on ice in 20 mM HEPES-KOH (pH 7.9), 5 mM KCl, 0.5 mM $MgCl_2$, 5 mM DTT and 0.1% Triton X-100, and was monitored by phase contrast microscopy. Initial PCR amplification was with ie1 primers IEP4BII (SEQ ID NO:25) and IEP2AII (SEQ ID NO:15) as previously described (Porter-Jordan, et al.) using a Perkin-Elmer Thermocycler (94° C. for 1 min, 62° C. for 1 min and 72° C. for 2 min) for 30 cycles.

One microliter of the initial reaction was used as the template in a subsequent reaction employing nested primers IEP3B (SEQ ID NO:19) and IEP3A (SEQ ID NO:18) (94° C. for 1 min, 52° C. for 1 min and 72° C. for 2 min) for 30 cycles. The reaction contained 50 mM KCl, 10 mM Tris-HCl (pH 8.5), 2 mM $MgCl_2$, 1 μM of each primer, 200 μM of each dNTP and 1.25 units of Taq polymerase (Perkin-Elmer, Foster, Calif.).

After amplification, 10% of each reaction was separated by electrophoresis on 2.5% agarose gels and the gels stained with ethidium bromide (Higchi). The sequences of primer used are shown in FIG. 7 and provided in the Sequence Listing. The expected sizes (bp) of both unspliced and spliced PCR products obtained with the primer pairs described above, as well as those obtained with other primer pairs, are summarized in Table 1, below.

TABLE 1

PREDICTED PRODUCTS FOR PCR ANALYSES

| Upstream Primer | Downstream Primer | Predicted Product (bp) | |
|---|---|---|---|
| | | Unspliced | Spliced |
| IEP4BII | IEP2AII | 721 | |
| IEP2AII | IEP3D | 263 | 151 |
| IEP3B | IEP3A | 167 | |
| IEP3C | IEP4BII | 387 | 217 |
| 2.7A | 2.7B | 238 | |
| 112A | 113B | 388 | 228 |
| 113D | 112A | 307 | 150 |

D. Quantitative competitive PCR $8 \times 10^4$ cells or nuclei were suspended in 60 μl of a solution containing 50 mM KCl, 10 mM Tris-HCl (pH 8.5), 2 mM $MgCl_2$, 0.45% NP-40, 0.45% Tween-20 and 100 μg/ml proteinase K, and incubated for 16 h at 65° C. followed by 10 minutes at 98° C. to inactivate proteinase K (Higchi). Each sample was divided into six equal portions and analyzed in the presence of $3 \times 10^3$ to $1 \times 10^6$ copies of denatured human CMV ie1 cDNA (obtained from pON2347, a construct carrying a 1549 bp EcoRI/XbaI fragment representing protein-coding sequences from exons 2, 3 and 4) as a competitive template (see FIG. 6). PCR amplification with the primers IEP3C (SEQ ID NO:20) and IEP4BII (SEQ ID NO:25) was performed for 30 cycles under the same conditions and analyzed by agarose gel electrophoresis as described for the nested PCR analysis.

E. Reverse transcription PCR

RNA was extracted from infected GM-Ps and control mixtures of CMV-infected HF cells and uninfected GM-P cells by standard method (Chomczynski & Sacchi). For all samples of $10^3$ or fewer GM-Ps, 2 μg of RNase-free yeast tRNA (Sigma) was added prior to RNA extraction. RNA was treated with 5 units of RNase-free RQ1 DNase (Promega, Madison, Wis.) in the presence of 100 units of "RNASIN" (Promega) for 1 hour at 37° C. and cDNA was synthesized using 1 µg of random hexamer primers and "SUPERSCRIPT II" murine leukemia virus reverse transcriptase (GIBCO/BRL) using the manufacturer's protocol.

For the $\beta_{2.7}$ gene transcript, which is unspliced, 45 cycles of PCR were performed using primers 2.7A (SEQ ID NO:4) and 2.7B (SEQ ID NO:5) and cycle parameters of 94° C. for 1 min, 60° C. for 1 min and 72° C. for 2 min.

For the spliced UL112/113 transcript, an asymmetric nested amplification was carried out first with primers 112A (SEQ ID NO:1) and 113B (SEQ ID NO:2) for 30 cycles (predicted product of 228 bp), and then with primers 113D (SEQ ID NO:3) and 112A (SEQ ID NO:1) (predicted product of 150 bp) for 30 cycles using cycle parameters of 94° C. for 1 min, 65° C. for 1 min and 72° C. for 2 min.

Figure 5A:
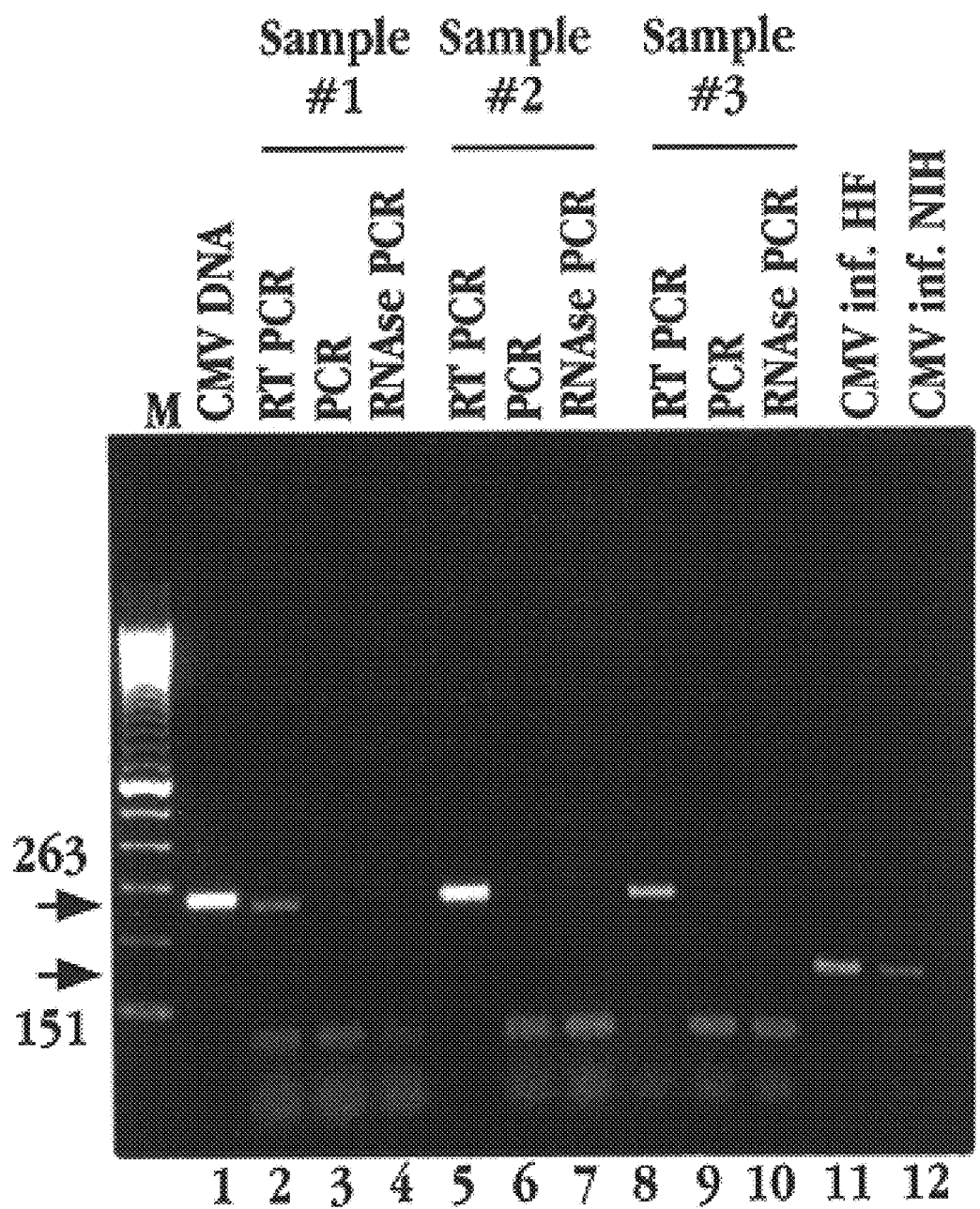
FIGS. 5A and 5B show expression between ie1 exons 2 and 3 (FIG. 5A) and expression between ie1 exons 3 and 4 (FIG. 5B) in ethidium bromide-stained gels of PCR reaction products.
Figure 5B:
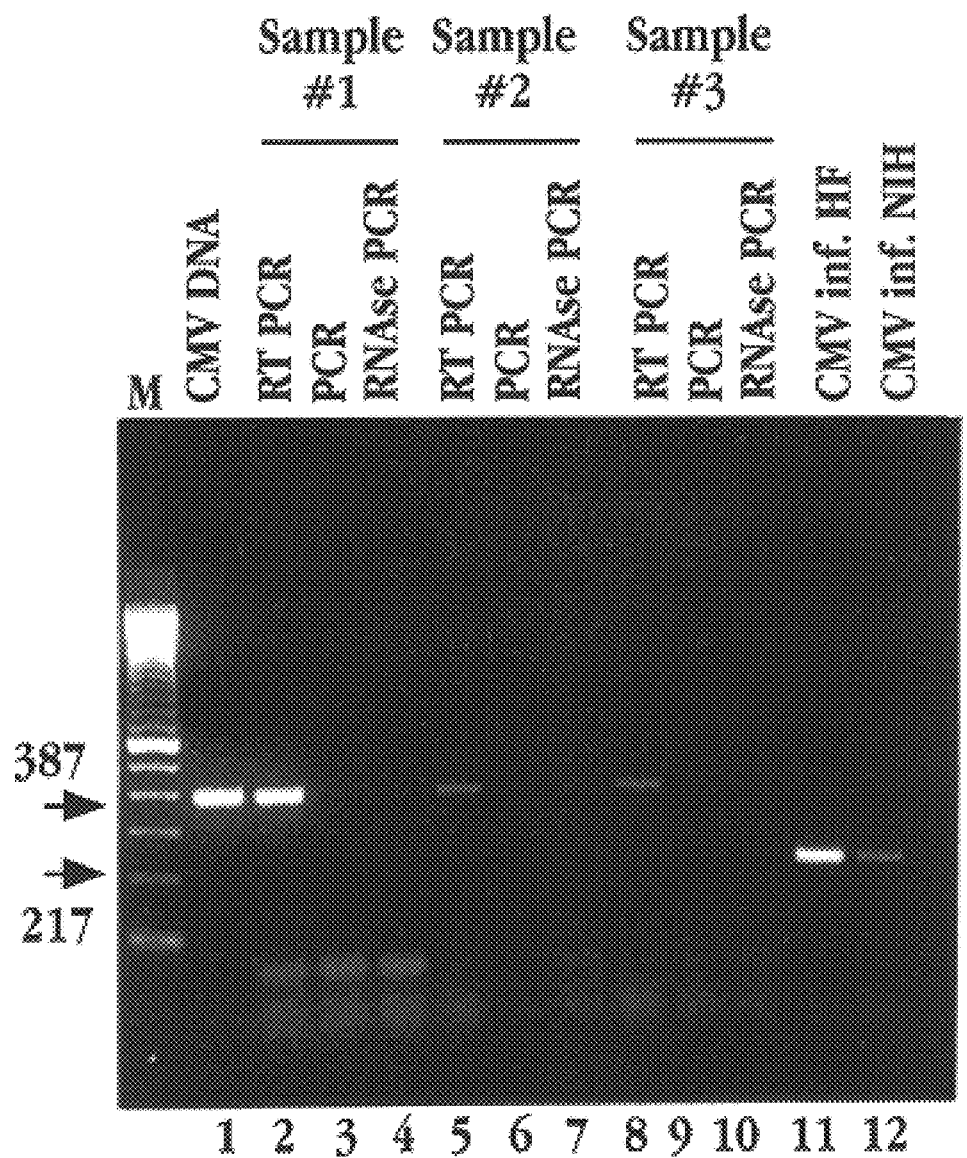

For the ie1 transcript, 30 cycles of PCR were performed using primers IEP2AII (SEQ ID NO:15) and IEP3D (SEQ ID NO:21) (exon 2–3; FIG. 5A) or IEP4BII (SEQ ID NO:25) and IEP3C (SEQ ID NO:20) (exon 3–4; FIG. 5B) using parameters of (94° C. for 1 min, 65° C. for 1 min and 72° C. for 2 min) or (94° C. for 1 min, 62° C. for 1 min and 72° C. for 2 min).

Following electrophoresis on 2.5% agarose gels, samples were visualized using ethidium bromide. For $\beta_{2.7}$ and UL112/113 transcript analyses, separated fragments were denatured and transferred to "HYBRIDON-N$^+$" membrane (Amersham, Arlington Heights, Ill.), hybridized with $^{32}$P dCTP-labeled (random primed, Amersham) DNA probes and subjected to autoradiography on Kodak X-OMAT film (Rochester, N.Y.).

F. 5'-RACE PCR

RNA isolated from $10^4$–$10^5$ GM-Ps at 4 weeks postinfection (see FIG. 1) was reverse transcribed either with "SUPERSCRIPT II" for 2 h at 45° C. in the presence of 10 pmol of primer IEP2E (SEQ ID NO:17) (for antisense transcripts) or with rTth reverse transcriptase (Perkin-Elmer) for 1 h at 70° C. in the presence of 10 pmol of primer IEP3D (SEQ ID NO:21) (for sense transcripts) in accordance with the manufacturers' protocols.

After RNase H digestion the cDNA was isolated by "QUICK SPIN" G-50 "SEPHADEX" column (Pharmacia Biotech, Piscataway, N.J.), and 10 µl of purified cDNA was 3'-tailed using 20 units of terminal deoxynucleotide transferase (GIBCO/BRL) in the presence of 250 µM dATP for 10 min at 37° C. in a volume of 20 µl. Five µl of this sample were subjected to PCR using 50 pmol of the appropriate primer (IEP3D—SEQ ID NO:21, for sense RNA and IEP3E—SEQ ID NO:22, for anti-sense RNA) and anchor primer (RL-1; SEQ ID NO:35) in a total volume of 100 µl. Taq polymerase was used initially for 40 cycles of PCR using cycle parameters of 94° C. for 1 min, 55° C. for 2 min and 72° C. for 3 min (C cycle parameters).

Following the first reaction, 1 µl of PCR product was amplified by 30 cycles PCR with 40 pmol of nested PCR primer (IEP2D—SEQ ID NO:16, or IEP1D—SEQ ID NO:7) for sense RNA and IEP3G (SEQ ID NO:23) for anti-sense RNA) along with primer N1 (SEQ ID NO:33) with "GENEAMP XL" PCR kit (Perkin-Elmer, Foster, Calif.) using cycle parameters of 94° C. for 15 sec, 60° C. for 1 min and 72° C. for 3 min (D cycle parameters).

G. 3'-RACE PCR

RNA isolated from $10^4$–$10^5$ GM-Ps at 4 weeks postinfection was subjected to reverse transcription for 2 h at 45° C. with "SUPERSCRIPT II" in the presence of 50 pmol of anchor primer (RL-1; SEQ ID NO:35) in a total volume of 20 µl in accordance with the manufacturer's (Gibco/BRL) recommended protocol. Five µl of this sample were amplified by PCR using 40 pmol of a CMV sequence-specific primer (IEP2AII—SEQ ID NO:15 for sense RNA and IEP3D—SEQ ID NO:21 for antisense RNA) and primer N2 (SEQ ID NO:34) in a volume of 100 µl. The "GENEAMP XL" PCR kit was used for 25 cycles of PCR. One µl of the PCR product was then amplified by 25 cycles PCR with 40 pmol of nested PCR primer (IEP3C—SEQ ID NO:20 for sense RNA and IEP2D—SEQ ID NO:16 for antisense RNA) along with primer N1 (SEQ ID NO:33) using D cycle parameters (see 5'-RACE PCR, above).

EXAMPLE 1

Myelomonocytic Cell Cultures

To establish cultures in which the direct interaction of CMV with GM-Ps could be investigated, fetal bone marrow or liver cells were cultivated under myelomonocytic cell culture conditions (Baines, et al.). These culture conditions supported the outgrowth of myelomonocytic lineage cells independent of stromal cells, which are permissive for CMV (Reiser, et al.). The nonadherent cell population in these suspension cultures expressed CD14, CD15 and CD33 cell surface markers as judged by multiparameter flow cytometry using a "FACSCAN" and murine monoclonal antibodies from Becton Dickenson (San Jose, Calif.), and exhibited a myelomonocytic morphology.

Cultures initiated with fetal bone marrow and with fetal liver allowed the outgrowth of a similar nonadherent population of cells which continued to grow for approximately four weeks. Nonadherent cells were transferred three times a week, initially to deplete stromal cells, and later to remove the large, adherent cells that differentiated in these cultures. Methycellulose colony forming assay (Kyoizumi, et al.) was used to estimate the colony forming units of granulocyte-macrophage (CFU-GM) in six independent fetal samples. The samples had between $1 \times 10^3$ to $5 \times 10^3$ CFU-GM/$10^6$ starting fetal liver cells.

FIG. 1 shows human CMV DNA maintenance in GM-P cultures. Six liver cell samples (2 replicate cultures from each) from different sources were placed into culture ($10^6$ total cells per culture, containing 1–$5 \times 10^3$ CFU-GM). Immediately following inoculation with 3 plaque forming units per cell (PFU/cell) of RC256, and subsequently at 3, 7, 14, 21 and 28 days postinfection (PI), CMV DNA copy number was determined using DNA from between $5 \times 10^4$ and $4 \times 10^5$ cells by quantitative competitive PCR (e.g., analysis of $8 \times 10^4$ cells is shown in FIG. 2C). The number of GM-Ps per culture was determined by direct counting, and the number of DNA-positive infected cells was determined by cell dilution PCR studies (Table 2 and FIGS. 2A, 2B and 2C). The legend in FIG. 1 is as follows: □, starting cell number; ■, CFU-GM number; ●, infected cell number; ○, total cell number; Δ, DNA copy number.

CFU-GM correlated with the numbers of CD34$^+$ cells in the starting cell population (these cells were likely precursors of the CD14$^+$, CD15$^+$, CD33$^+$ GM-P population). The data indicated that over 50% of the cells used to initiate these cultures were CD33$^+$, and that a small proportion were CD34$^+$ and capable of forming CFU-GM.

EXAMPLE 2

Infection of Cell Cultures with CMV

For infection with CMV, duplicate or triplicate samples of $10^6$ fetal liver cells from 10 individual CMV-negative sources were placed into culture. Three days later, nonadherent cells were collected, counted and exposed to CMV (RC256) at a multiplicity of infection (MOI) of 3. RC256, a derivative of the Towne strain that carries the lacZ gene under the control of the strong CMV β (delayed early) promoter ($β_{2.7}$), was used because this virus expresses abundant levels of β-galactosidase (β-Gal), which provided a simple and sensitive indicator of viral replication in cells and tissues (Spaete & Mocarski, Mocarski, et al., 1993).

Infected cells were washed free of virus and placed in culture. At weekly intervals, $10^5$ GM-Ps were removed from duplicate or triplicate cultures made from each independent fetal sample. Viral infection had no significant effect on growth or morphology of either nonadherent or adherent cells.

EXAMPLE 3

Detection of β-Gal Expression

Ten samples of RC256-infected GM-P cells were harvested at three weeks or four weeks after infection. Freeze/thaw (F/T) released free virus was plaque-assayed on HF cells. $10^5$ GM-Ps were cocultivated with HF cells for 12 days to detect infectious centers (ICs). β-Gal was detected by overlay of $10^5$ cells with 5-bromo-3-chloro-indolyl-β-D-galactopyranoside (X-gal) as previously described (Baines, et al.).

Weekly samples were subjected to analysis for the presence of infectious virus and for β-Gal expression as an indicator of viral β (delayed early) gene expression (Table 2). Neither the plaque assay of freeze-thawed cell lysates nor the infectious centers assay of intact cells yielded evidence of virus replication in the GM-P population, consistent with previous reports (Reiser, et al., Apperley, et al., Simmons, et al., Sing & Ruscetti). Furthermore, the cells did not stain with X-gal. Taken together, these findings indicate that neither residual input infectious virus nor viral replication was detectable in these cultures.

TABLE 2

DETECTION OF VIRAL INFECTIVITY, β-GAL EXPRESSON AND VIRAL DNA IN GM-P CELL CULTURE

| PI | Virus, % Positive* | | β-Gal, Positive* (X-Gal | Viral DNA, % Positive* | | |
|---|---|---|---|---|---|---|
| Weeks | F/T | IC | Stain) | 10–30† | 3–10† | 1–3† |
| 3 | 0 | 0 | 0 | 100 | 100 | 60 |
| 4 | 0 | 0 | 0 | 100 | 100 | 70 |

*Percentage positive of 10 culture samples ($10^5$ per sample).
†Number of cells assayed.

EXAMPLE 4

PCR Detection of CMV

Ten samples of RC256-infected GM-P cells were harvested at three weeks or four weeks after infection. Freeze/thaw (F/T) released free virus was plaque assayed on HF cells. $10^5$ GM-Ps were cocultivated with HF cells for 12 days to detect infectious centers (ICs). DNA isolated from the indicated numbers of cells was extracted and subjected to nested PCR assay using ie1 region primers.

A high proportion (between 10 and 100%, depending on the sample) of the cells in the 10 individual samples of GM-Ps were found to be positive for CMV DNA by cell dilution PCR analysis (Table 2, above) using a nested set of primers for the ie1 region. The interaction of CMV with GM-Ps is summarized in FIG. 1 for six of the ten cultures. DNA copy number was calculated immediately following infection and at 3, 7, 14, 21, and 28 days after infection using quantitative competitive PCR.

The cumulative cell number was also determined by direct count of cells, and the percentage of those cells that were genome positive was estimated by cell dilution followed by nested DNA PCR. As GM-Ps proliferated, cell numbers accumulating to $10^7$ to $10^8$ cells/culture, viral DNA accumulated in parallel with the number of cells. Cells and nuclei isolated from the same six cultures were compared by dilution analysis, and viral DNA was found to be mainly associated with the nuclear fraction of cells. Examples in which viral DNA was detected in samples containing three or more cells or nuclei are shown in FIGS. 2A, 2B and 2C.

Figure 2A:
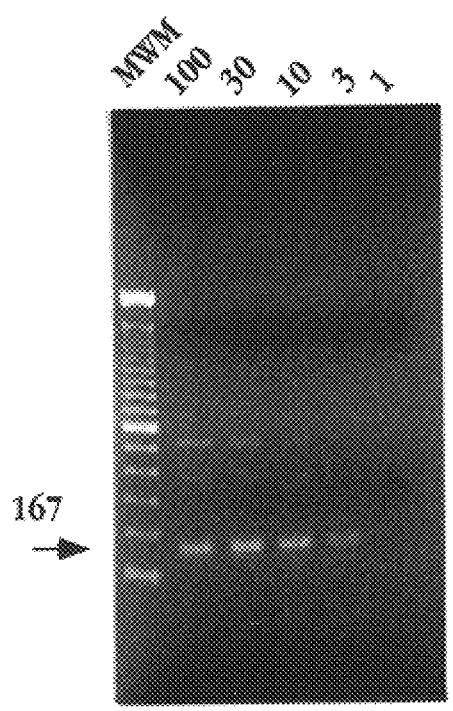
FIGS. 2A, 2B and 2C show ethidium bromide-stained gels of PCR reaction products showing retention of CMV DNA in cells and nuclei.
Figure 2B:
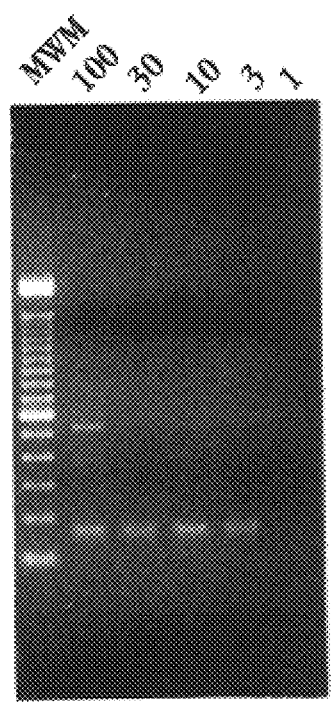
Figure 2C:
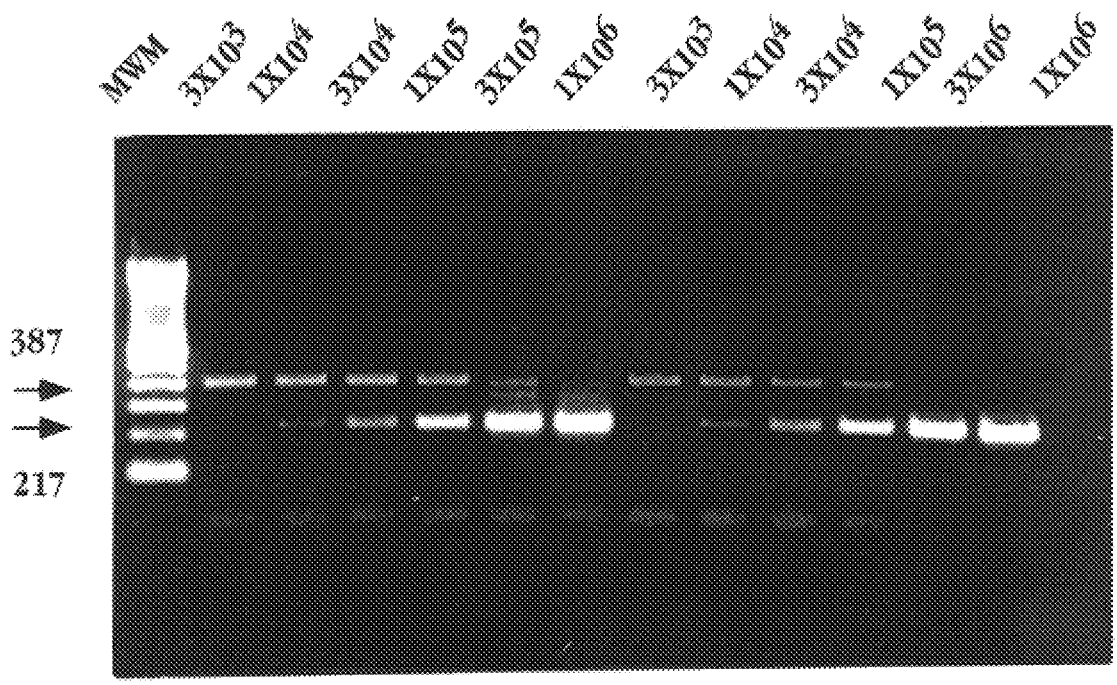

FIGS. 2A and 2B show retention of CMV DNA in cells and nuclei. Cells (FIG. 2A) and nuclei (FIG. 2B) were counted and diluted to give an average of 100, 30, 10, 3 and 1 per tube, as indicated above the lanes, before DNA was prepared (Kondo, et al., 1991). The position of the 167 bp product generated by nested PCR with ie1-specific primers, first using IE4BII and IEP2AII (SEQ ID NO:15) for 30 cycles, and then using IEP3B (SEQ ID NO:19) and IEP3A (SEQ ID NO:18) for 30 cycles is indicated next to the lanes of ethidium bromide stained agarose gel. MWM: 100 bp ladder (Gibco/BRL).

FIG. 2C shows the results of an exemplary experiment to determine the CMV DNA copy number. DNA isolated from $8×10^4$ cells (left half) or $8×10^4$ nuclei (right half) was subjected to quantitative PCR with the primers IEP3C (SEQ ID NO:20) and IEP4BII (SEQ ID NO:25) in the presence of $3×10^3$ to $1×10^6$ copies a denatured human CMV ie1 cDNA plasmid as competitor. Copy numbers are indicated at the top of the lanes. The position of the 387 bp product from human CMV DNA and the 217 bp product from the competitive template are indicated next to the lanes of the ethidium bromide stained agarose gel.

The results reveal that approximately $3×10^4$ CMV genomes were present in these samples, which is equivalent to approximately 20 genomes/genome positive cell. Results of this analysis for all samples demonstrated that CMV DNA was present in 10 to 100% of GM-Ps in independently established cultures (Table 2, above). Quantitative competitive PCR (Higchi) with an ie1 cDNA clone as competitor, was used to estimate a viral genome copy number of 10–100 copies per genome-positive cell, a number consistent with the analysis of nuclear DNA (e.g., FIG. 2C). The results indicate that CMV DNA was quantitatively associated with GM-P cells at genome copy numbers characteristic of latent infection by other herpesviruses.

EXAMPLE 5

Long-term Co-cultivation

Since GM-Ps continued to proliferate during the 12 days of coculture with HF cells, despite the fact that they had already been in myelomonocytic culture for up to a month, experiments were performed to determine if virus might be recovered following a longer period of cocultivation.

Infected GM-Ps were examined for ability to yield virus following long-term cocultivation with HF cell monolayers. Ten individual samples of RC256-infected myeloid cells, at four weeks PI, were harvested and counted. Approximately 300 infected cells from each sample were transferred into each of 48 wells of a 96 well culture dish that had been seeded previously with HF cells. Twelve wells (all containing cells from the same sample) were stained with X-gal at 5, 12, 16 and 21 days after initiating cocultivation. As a positive control, and to illustrate the rapid spread of CMV from a productively infected cell under these conditions, 300 HF cells containing 1–5 infected cells per well were also cocultivated with uninfected HF cells. These cultures were maintained for an additional three week period. Recovery of virus (plaque formation) was assessed at 5, 12, 16 and 21 days after cocultivation, and is summarized in Table 3, below.

TABLE 3

REACTIVATION OF LATENT VIRUS

| | Number of CPE-Positive Wells | |
|---|---|---|
| Days | Infected Myeloid Cells | Infected HF Cells |
| 5 | 0/120 | 120/120 |
| 12 | 0/120 | ND |
| 16 | 3/120 | ND |
| 21 | 97/120 | ND |

ND - not done; CPE - cytopathic effect

Although the GM-Ps remained virus-negative through the 12 day time point, by 21 days, 80% of samples yielded virus. For comparison, a few productively infected HF cells cultured in parallel yielded plaques within five days, and an input of one cell-free infectious virus yielded a plaque within seven days.

Accordingly, virus associated with GM-Ps is recovered with considerably-delayed kinetics, consistent with reactivation from latency rather than persistence of small amounts of infectious virus. Reactivation occurred in all of the 10 samples studied when 300 GM-Ps were seeded, thereby showing reproducible recovery of infectious virus from the latently infected GM-Ps. When fewer than 300 GM-Ps were seeded, proportionately fewer wells showed reactivation, suggesting that not every genome positive cell in the culture was capable of yielding virus under these conditions. Similar results were obtained with the low-passage Toledo strain of CMV.

EXAMPLE 6

Detection of Viral α- and β-gene Expression by RT-PCR

The ten GM-P cultures described above (four weeks PI) were analyzed for evidence of viral α and β gene expression by direct RT-PCR as detailed in the Materials and Methods. The PCR reaction products were resolved on 2.5% agarose gels and stained with ethidium bromide. For $\beta_{2.7}$ and UL112/113 transcript analyses, separated fragments were also blotted and probed with $^{32}$P dCTP-labeled specific DNA probes as described in the Materials and Methods.

Figures 3A, 3B:
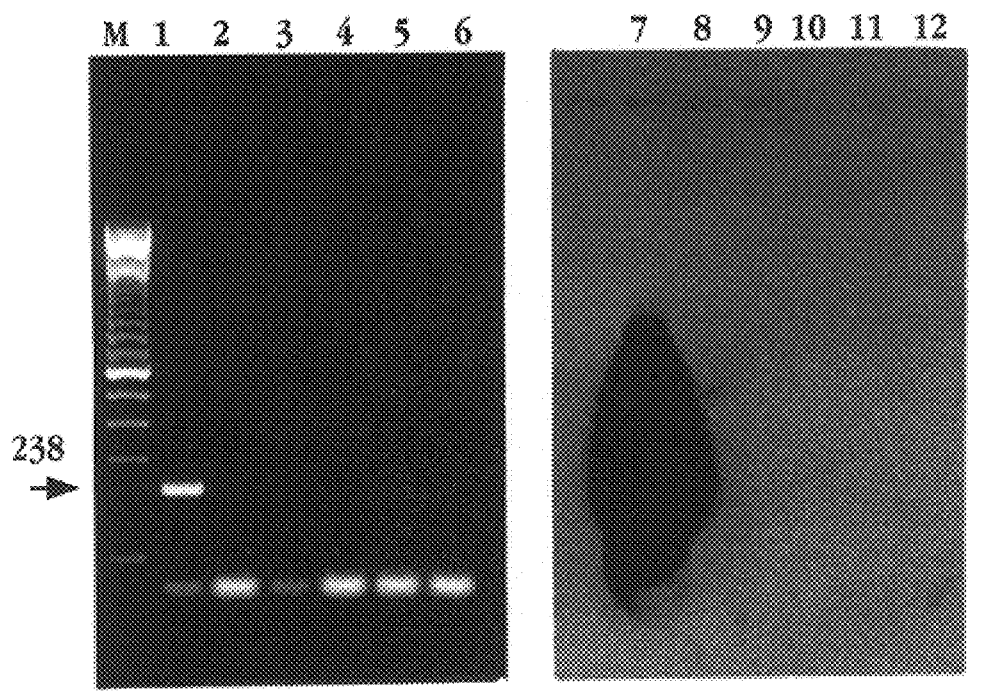
FIGS. 3A and 3B show electrophoretic separation (2.5% agarose gels) of RT-PCR products of human CMV $\beta_{2.7}$ gene expression $\alpha$ and $\beta$ gene transcripts in GM-Ps at four weeks PI.
Figures 4A, 4B:
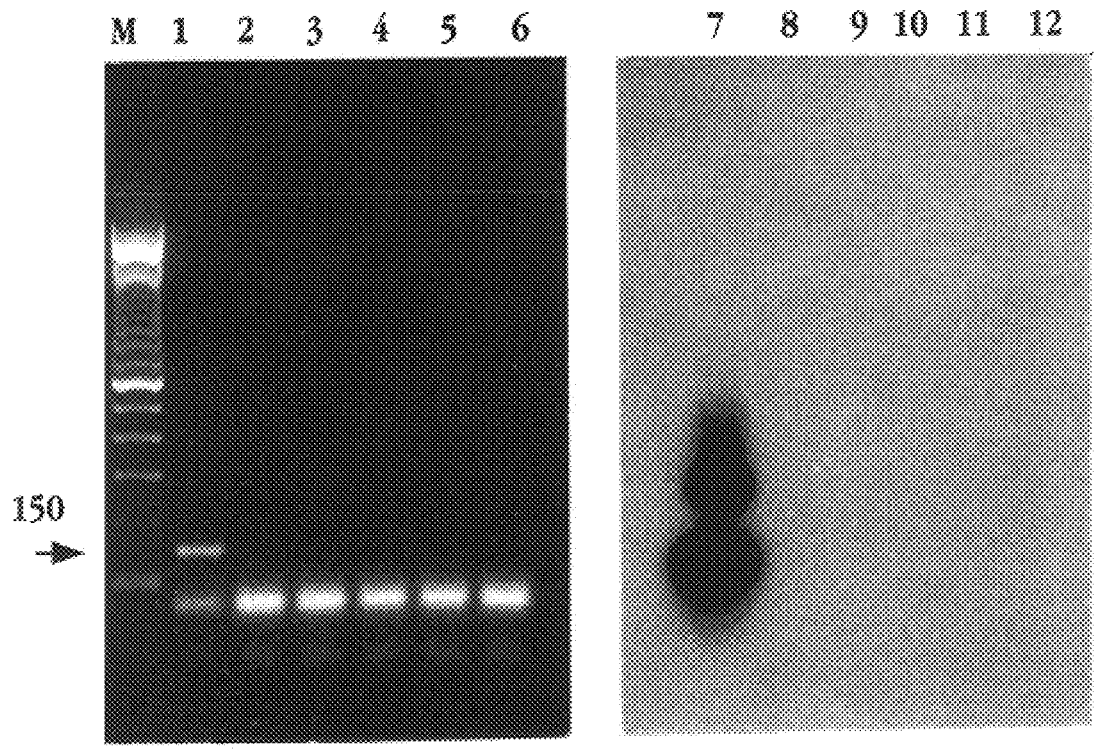
FIGS. 4A and 4B show electrophoretic separation (2.5% agarose gels) of RT-PCR products of human CMV UL112/113 gene expression.

FIGS. 3A (ethidium bromide stained gel) and 3B (blot autoradiograph) show results of RT-PCR analyses from five different samples of RNA (FIG. 3A: lanes 2–6; FIG. 3B: lanes 8–12), each sample from $10^5$ cells, using PCR primers capable of detecting unspliced transcripts from the abundantly expressed $\beta_{2.7}$ gene (Greenaway & Wilkinson). FIGS. 4A and 4B show results of RT-PCR analyses performed as above, but using primers designed to amplify a family of spliced transcripts from the UL112–113 gene (Staprans & Spector). Neither $\beta_{2.7}$ nor UL112–113 transcripts were detected, even though the conditions used were sensitive enough to detect transcripts in a single infected HF cell (8 h after infection) mixed in with $10^5$ uninfected GM-Ps (lane 1 in FIGS. 3A and 4A; lane 7 in FIGS. 3B and 4B). Lanes labeled M show 100 bp ladder size markers (GIBCO/BRL).

Alpha gene ie1 RT-PCR transcript analyses, using primers as detailed in the Materials and Methods, are shown in FIGS. 5A and 5B. The experiments presented in FIGS. 5A and 5B used RNA from three different samples (#1, #2 and #3) of $10^3$ infected GM-Ps. Three analyses were performed for each sample, (i) one in which reverse transcriptase was included in the reactions (RT PCR), (ii) as controls, one in which reverse transcriptase was left out of the reaction (PCR), and (iii) one where RNA was treated with 20 ng of RNase A (Sigma) for 1 hour at 37° C. prior to RT-PCR (RNase PCR).

All samples of RNA were also treated with RNase-free RQ1 DNase. PCR of CMV DNA from a sample of $10^3$ infected GM-Ps is also shown for comparison in lane 1. Controls included RNA extracted from 10 infected HF cells (4 h) mixed with $10^3$ uninfected GM-P cells (FIGS. 5A and 5B; lane 11), or from 10 infected NIH3T3 cells (4 h) mixed with $10^3$ uninfected GM-P cells (FIGS. 5A and 5B; lane 12).

Data in FIG. 5A were generated using primers that amplify exons 2–3 and data in FIG. 5B were generated using primers that amplify exons 3–4 (Materials and Methods). The positions of the 151 bp spliced and 263 bp unspliced products are indicated by arrows in FIG. 5A, while the 217 bp spliced and the 387 bp unspliced products are indicated by arrows in FIG. 5B. The 30 cycle PCR conditions used here was semi-quantitative, so band intensities estimate RNA levels. Lane M shows 100 bp ladder size markers (GIBCO/BRL).

Transcription from the abundant α gene, ie1, was readily detected in all six infected GM-P cultures, even when RNA from as few as $10^3$ cells was evaluated by RT-PCR (three examples are shown for each of two different ie1 regions in FIGS. 5A and 5B). Analyses using RNA from uninfected GM-Ps were uniformly negative. Surprisingly, the observed signal was largely derived from unspliced RNA in the infected GM-Ps, rather than from spliced RNA typical of either productively infected HF or abortively infected mouse NIH3T3 fibroblasts. An overwhelming majority of ie1 RNA remained unspliced in all six independent GM-P cultures examined, and was readily detected in RNA from $10^3$ cells by RT-PCR. The presence of unspliced RNA was demonstrated between exons 2 and 3 (FIG. 5A) or exons 3 and 4 (FIG. 5B) of the ie1 gene.

Using semiquantitative PCR conditions, it was estimated that each sample of RNA contained at least $10^3$ copies of cDNA prior to amplification. Between 70% and 99% of these transcripts remained unspliced as estimated by probing PCR reaction products with internal oligonucleotide probes. This high relative abundance of unspliced transcript is unusual and indicates that ie1 gene expression during latency may be different than occurs during productive infection (Morarski, 1993).

Results from RT-PCR analyses of RNA isolated from a cell dilution series suggest that no fewer than 2–5% of CMV genome positive cells contained unspliced ie1 transcript. Experiments employing monoclonal antibodies failed to detect any evidence of the 72 kDa ie1 gene product in these cells, consistent with the relative absence of appropriately spliced transcript. Further analyses have shown that approximately 10% of this unspliced RNA is to be polyadenylated.

EXAMPLE 7

Strand-specific Amplification of CMV cDNAs from Latently Infected GM-Ps

Figure 6:
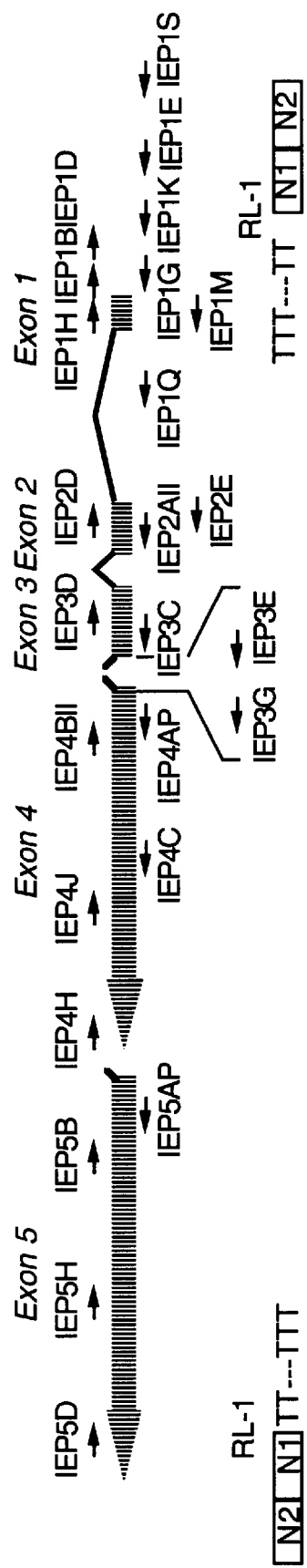
FIG. 6 shows the relative positions of primers for reverse transcription (RT) and rapid amplification of cDNA ends (RACE) polymerase chain reaction (PCR) reactions.

The ie1/ie2 region transcripts were reverse transcribed with strand-specific primers under stringent conditions (70° C.) and were used in PCR to amplify cDNAs from latently infected GM-Ps. The relative positions of the primers used in these analyses are shown in FIG. 6. The sequences of the primers are shown in FIG. 7 and are provided in the Sequence Listing.

Thirty cycles of PCR were used with primers IEP2AII (SEQ ID NO:15) and IEP3D (SEQ ID NO:21) or IEP4BII (SEQ ID NO:25) and IEP3C (SEQ ID NO:20) using parameters of 94° C. for 1 min, 65° C. for 1 min and 72° C. for 2 min (A cycle parameters) or 94° C. for 1 min, 62° C. for 1 min and 72° C. for 2 min (B cycle parameters), respectively. The reaction contained 50 mM KCl, 10 mM Tris-HCl pH 8.5, 2 mM $MgCl_2$, 1 µM of each primer, 200 µM of each dNTP and 1.25 units of Taq polymerase (Boehringer Mannheim).

Oligonucleotides IEP4BII (SEQ ID NO:25) and IEP2AII (SEQ ID NO:15) were used to prime synthesis of cDNA from sense and antisense transcripts, respectively. Following PCR with primers IEP2AII (SEQ ID NO:15) and IEP3D (SEQ ID NO:21) (ie1 exons 2 and 3) or IEP3C (SEQ ID NO:20) and IEP4BII (SEQ ID NO:25) (ie1 exons 3 and 4) as described above, products were resolved by agarose gel electrophoresis.

Figure 8:
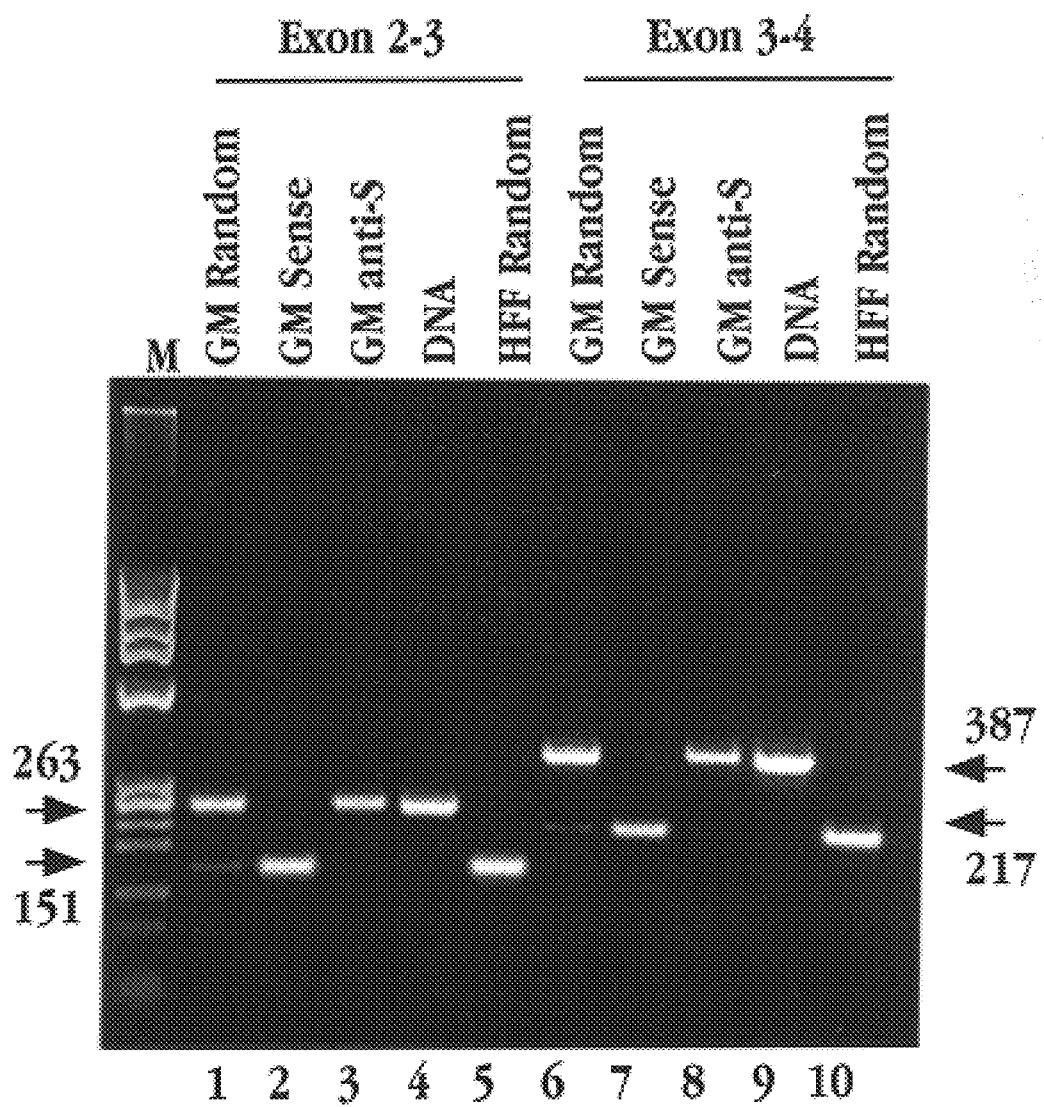
FIG. 8 shows an RT-PCR analysis of human CMV immediate early ($\alpha$) gene expression and sense and antisense ie1/ie2 region transcripts in latently infected GM-Ps at four weeks PI.

The results, shown in FIG. 8, test for expression between ie1 exons 2 and 3 (lanes 1–5) and between ie1 exons 3 and 4 (lanes 6–10). RNA was prepared by single-step acid guanidinium thiocyanate-phenol-chloroform extraction (Chomczynski and Sacchi, 1987) from $10^4$ (lanes 1–3 and 6–8) latently infected GM-Ps and compared with RNA extracted from 10 productively infected (4 h postinfection) human fibroblast (HF) cells (lanes 5 and 10).

For each sample, 2 µg of RNase free yeast tRNA (Sigma) added prior to RNA extraction. All RNA samples were treated with 5 units of RNase free RQ1 DNase (Promega) in the presence of 100 units of "RNASIN" (Promega) for 1 h at 37° C. prior to reverse transcription.

For samples in lanes 1, 5, 6 and 10, cDNA was synthesized using random hexamer primers (GIBCO/BRL) and "SUPERSCRIPT II" reverse transcriptase (GIBCO/BRL) in accordance with the manufacturer's recommended protocol. For samples in lanes 2, 3, 7 and 8, five units of thermostable rTth reverse transcriptase (Perkin-Elmer) were used with primer IEP4BII (SEQ ID NO:25) to copy the sense strand (lanes 2 and 7) and with primer IEP2AII (SEQ ID NO:15) to copy the antisense (anti-S) strand (lanes 3 and 8).

Incubation was for 30 min at 70° C. in accordance with manufacture's protocol after which samples were subjected to PCR as detailed above. Approximately $10^5$ copies of viral DNA (lanes 4 and 9) were subjected to the same PCR conditions and were used for comparison. Electrophoretic separation was in a 2.5% agarose gel followed by staining with ethidium bromide.

Arrows adjacent the lanes indicate the position of the predicted 151 bp spliced and 263 bp unspliced exon 2–3 products (lanes 1–5), and 217 bp spliced and the 387 bp unspliced exon 3–4 products (lanes 6–10). Size markers (M) are HaeIII-digested φX174 DNA.

The analyses detailed above showed that spliced RNA was being transcribed in the sense orientation (FIG. 8, lanes 2 and 7) while unspliced RNA was transcribed in antisense orientation (FIG. 8, lanes 3 and 8) to generate transcripts normally produced during viral replication (Stenberg, et al., 1984; Stenberg, et al., 1985).

Consistent with results presented in FIG. 2C, random-primed GM-P RNA yielded both types of PCR products (lanes 1 and 6), which is different than the spliced pattern detected in productively infected human foreskin fibroblast (HF) cells (FIG. 8, lanes 5 and 10). These results indicate that sense, as well as antisense, transcripts from the ie1 region were detected in GM-Ps, with antisense transcripts predominating.

EXAMPLE 8

Structure of Latent Transcripts—3' and 5' RACE PCR

To analyze the structure of latent transcripts, 5'- and 3'-RACE (rapid amplification of cDNA ends) procedures (Ohara, et al., 1989) were employed to map the ends of transcripts expressed in GM-Ps. The RACE-PCR experiments were performed as described in the Materials and Methods section, above.

Isolation of Latent Transcripts

Figure 9:
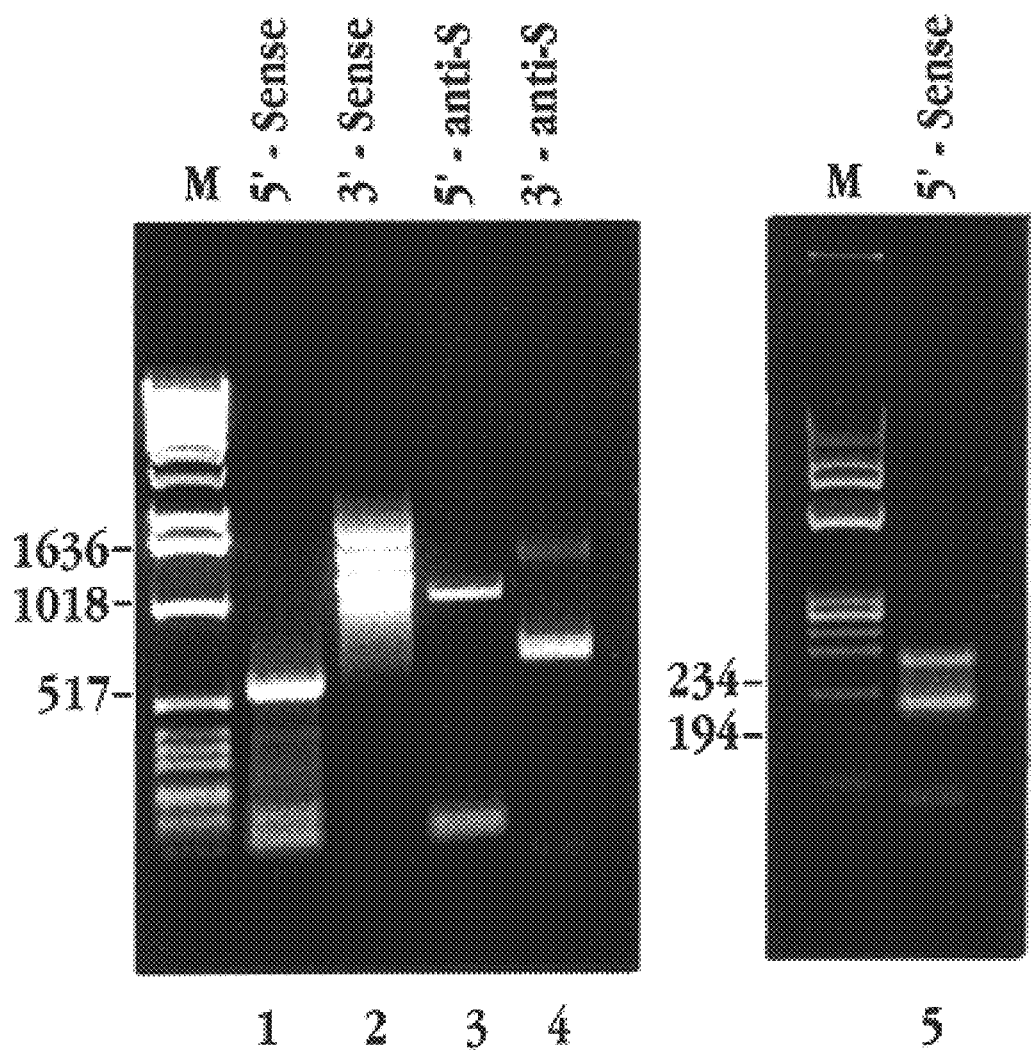
FIG. 9 shows an ethidium bromide-stained gel of PCR reaction products identifying the 5'- and 3'-ends of latent transcripts.

Results of the RACE-PCR experiments are shown in FIG. 9. RACE products from sense (lanes 1, 2 and 5) and anti-sense RNA (lanes 3 and 4) are shown. Lane 1, 5' RACE amplified with N1 (SEQ ID NO:33) and IEP2D (SEQ ID NO:16); Lane 2, 3'-RACE amplified with N1 (SEQ ID NO:33) and IEP3C (SEQ ID NO:20); Lane 3, 5' RACE amplified with N1 (SEQ ID NO:33) and IEP3G (SEQ ID NO:23); Lane 4, 3'-RACE amplified with N1 (SEQ ID NO:33) and IEP2D (SEQ ID NO:16); Lane 5, 5' RACE amplified with N1 (SEQ ID NO:33) and IEP1D (SEQ ID NO:7).

The PCR products were separated by agarose gel (1.2% for lanes 1–4, 2.5% for lane 5) electrophoresis. A 1 kb ladder (GIBCO/BRL) and HaeIII digested φX174 DNA were used as size markers, the positions of some of which are marked (in # of bp) at the left of each set of lanes.

Following PCR, two 5' ends of sense transcripts were positioned approximately 600 bp upstream of the annealing site of the IEP2D (SEQ ID NO:16) primer (FIG. 9, lane 1) and, by higher resolution analysis using primer IEP1D (SEQ ID NO:7), these two 5' ends were placed approximately 50 bp apart (FIG. 9, lane 5). A number of PCR products ranging in size from under 1.0 kbp to approximately 1.7 kbp were generated from sense transcripts by 3' RACE followed by PCR using the primers IEP3C (SEQ ID NO:20) and N1 (SEQ ID NO:33) (FIG. 9, lane 2), suggesting considerable heterogeneity in the body of these transcripts.

Using similar methods (as described above), the 5'-ends of antisense transcripts were mapped approximately 1.1 kbp upstream of the IEP3G (SEQ ID NO:23) annealing site and the 3'-end of this transcript was mapped approximately 0.7 kbp downstream of the IEP2D (SEQ ID NO:16) primer annealing site. The sequence of the 5' ends of these transcripts was determined following cloning into a T-A vector, as described below.

Cloning of Latent Transcripts

In order to identify the 5' ends of sense transcripts, 5' RACE product was subjected to PCR with primers IEP2D (SEQ ID NO:16) and N1 (SEQ ID NO:33), and products cloned into pGEM-T vector. An ie1/ie2 promoter-enhancer probe was used for colony-blot hybridization to isolate clones that contained 5' ends upstream of the start site used during productive infection. Sequence determination was with "SEQUENASE" version 2.0 (Amersham) and the fmole DNA Sequencing System (Promega).

The presence of the exon 1/exon 2 splice was also conserved in these clones. To precisely position LSS1, 5' RACE product was subjected to PCR with primers IEP1D (SEQ ID NO:7) and RL-1 (SEQ ID NO:35) for 40 cycles using Taq polymerase and C cycle parameters (5'-RACE PCR, Materials and Methods), and 1 µl of this PCR product was amplified using 40 pmole of nested primers IEP1D (SEQ ID NO:7) and N1 (SEQ ID NO:33) for 30 cycles using the "GENEAMP XL" PCR kit and D cycle parameters (5'-RACE PCR, Materials and Methods). Seven independent clones were isolated from three different donor cell preparations. Two clones (pON2218 and pON2219) exhibited identical sequence at their 5' ends (SEQ ID NO:48) and pON2220 showed one additional nontemplate G (SEQ ID NO:49) at −356 (LSS1) relative to the PSS. Three clones (pON2222, pON2223, pON2224) exhibited identical sequence at their 5' ends (SEQ ID NO:50) at −292 (LSS2) relative to the PSS. In order to identify the 3' ends of the sense transcript, 3' RACE product was amplified with N1 (SEQ ID NO:33) and IEP3C (SEQ ID NO:20) primers and 4 clones, one representing exon 4 and three different sized clones from exon 5, were sequenced and found to use the same polyadenylation sites as productive infection transcripts (Stenberg, et al., 1984; Stenberg, et al., 1995; Stenberg, et al., 1989). In order to identify the 5' end of the antisense transcript, the 5' RACE product was amplified by N1 (SEQ ID NO:33) together with either IEP4C (SEQ ID NO:26) or IEP3G (SEQ ID NO:23), and products were cloned. Four clones hybridizing to $\alpha^{32}P$ dCTP random primed labeled SacI/BamHI fragment containing the ie1/ie2 from pON2347 (Sambucetti and Mocarski, unpublished) were isolated and sequenced. Two of these clones (pON2227 and pON2228) exhibited identical ends (SEQ ID NO:51), and two (pON2225 and pON2226) were shorter (SEQ ID NO:52 and SEQ ID NO:53, respectively). In order to identify the 3' ends of the antisense transcript, the 3' RACE product was amplified and 4 clones (pON2229, pON2230, pON2231, pON2232) that hybridized to IEP2AII (SEQ ID NO:15) exhibited an identical 3' sequence (SEQ ID NO:54).

Sequence Analysis of Latent Transcripts

Multiple 5' RACE clones from sense and antisense products were subjected to nucleotide sequence analysis. The three longest, independently isolated sense cDNA clones all identified latent start site 1 (LSS1) as SEQ ID NO:36, where $^{+1}$ (just 5' to the first nucleotide in the sequence) corresponds to nt 173,259 on the AD169 genome sequence, available as accession number X17403 from GenBank. Other clones identified latent start site 2 (LSS2) as SEQ ID NO:37 where $^{+1}$ (just 5' to the first nucleotide in the sequence) corresponds to nt 173,195 on AD169.

Figure 10:
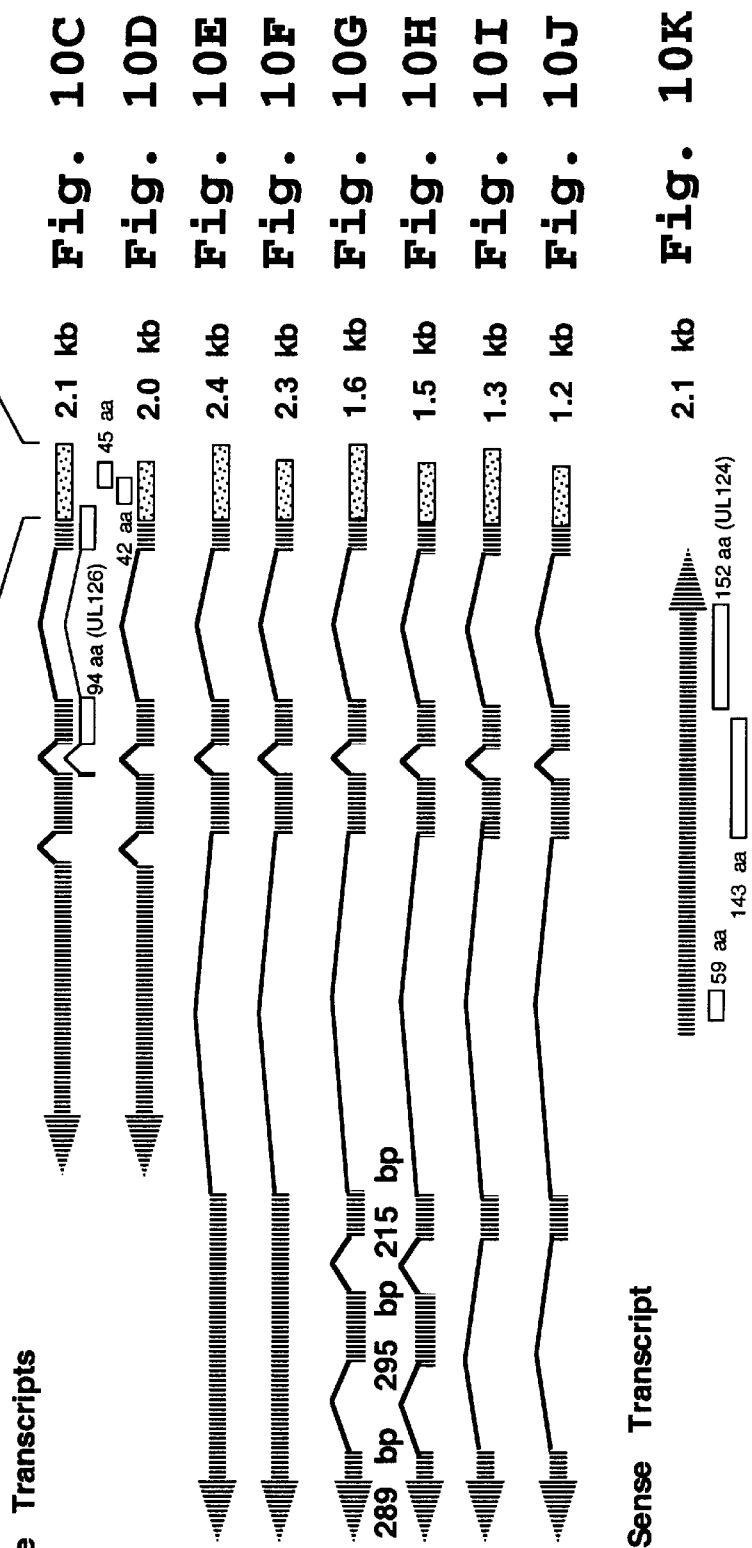
FIGS. 10A, 10B, 10C, 10D, 10E, 10F, 10G, 10H, 10I, 10J and 10K show a summary of latent transcript structure and predicted open reading frames (ORFs).
Figure 11:
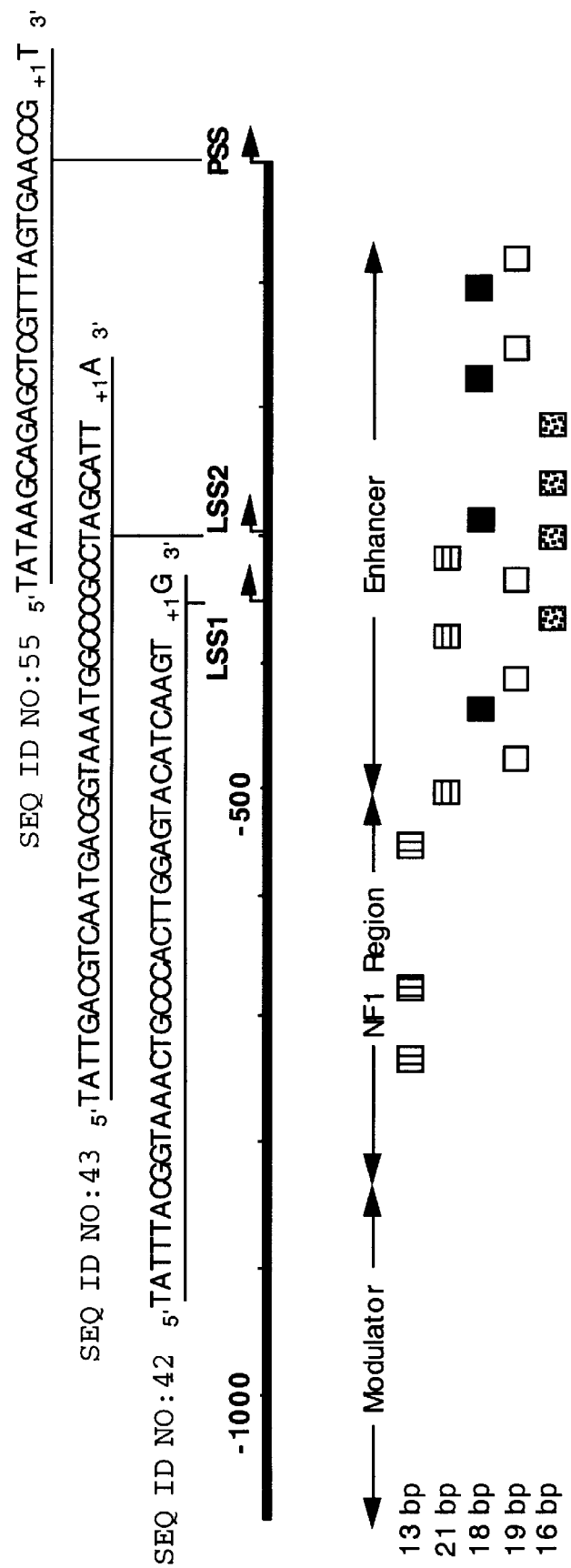
FIG. 11 shows the relative locations of productive infection-specific (PSS) and latent infection-specific (LSS1, LSS2) promoters in the human CMV ie1/ie2 locus.

These 5'-ends were located 356 bp and 292 bp, respectively, upstream of the productive infection start site (PSS—SEQ ID NO:55; FIGS. 10A, 10C, 11). Based on sequencing 3' RACE cDNA constructs, the 3' ends of these transcripts mapped to the same polyadenylation sites used during productive infection (Steinberg, et al., 1984; Stenberg, et al., 1985). The major structural difference during latency was the presence of a longer exon 1 on sense transcripts (FIGS. 10C–10J). None of the isolated clones initiated at PSS. The 5' end of antisense transcripts was more heterogeneous based on analysis of the four longest independent cDNA clones, two had the same sequence (SEQ ID NO:38), where $^{+1}$ (just 5' to the first nucleotide in the sequence) corresponds to nt 171,256 on AD169, and two were slightly shorter (SEQ ID NO:39 and SEQ ID NO:40). The 3' end of antisense cDNAs was uniform (SEQ ID NO:41), where the 3' proximal T corresponds to nt 173,331 on AD169).

EXAMPLE 9

Structure of Latent Transcripts—"GENEAMP XL" PCR

Based on 5'-end sequences, primers specific for the 5'-ends of transcripts (IEP1E—SEQ ID NO:8 or IEP1K—SEQ ID NO:11 for sense, and IEP4J—SEQ ID NO:28 for antisense) were combined with the 3'-RACE anchor primer RL-1 (SEQ ID NO:35) and the "GENEAMP XL" amplification procedure to complete the structural analysis of latent transcripts.

RNA was isolated from $10^6$ infected GM-Ps (4 weeks postinfection; see FIG. 1) and cDNA was synthesized using primer RL-1 (SEQ ID NO:35) and "SUPERSCRIPT II" RT in a 20 µl reaction, from which 5 µl was placed in a 20 µl reaction and amplified with 40 pmoles of primers IEP1E (SEQ ID NO:8) and N2 (SEQ ID NO:34) for LSS1, or IEP1K (SEQ ID NO:11) and N2 (SEQ ID NO:34) for LSS2, and "GENEAMP XL" using B cycle parameters (see Example 7, below). One µl from this reaction was subjected to a further 25 cycles of PCR using primers IEP1G (SEQ ID NO:9) and N1 (SEQ ID NO:33) under the same conditions.

Amplified products were cloned into the pGEM-T vector (Promega Corp.) and clones were identified by hybridization with $^{32}P$-labeled pON2347, IEP4AP (SEQ ID NO:24) and IEP5AP (SEQ ID NO:29) probes. Candidate clones were further analyzed by PCR with primer sets IEP1M-IEP2D, IEP2AII-IEP3D, IEP3C-IEP4BII, IEP3C-IEP5B, IEP4AP-IEP4H, IEP5AP-IEP5D and IEP5AP-IEP5H. Two different types of clones (pON2235 and pON2236) represented the 2.1 and 2.0 kb ie1 region cDNAs (FIGS. 10C and 10D). Six different types of clones (pON2237–pON2242) representing the 2.4, 2.3, 1.6, 1.5, 1.3 and 1.2 kb ie2 species were characterized by sequence analysis, resulting in the structures depicted in FIGS. 10E–10K, respectively These cDNA clones were evaluated by PCR analysis with exon-specific primers as well as by sequence analysis. For the most part, RNA splicing and polyadenylation patterns were similar to those used during productive infection. However, one additional splice donor and acceptor were used during latency, resulting in two spliced exon 5 derivatives not observed during productive infection (FIGS. 10G and 10H). Thus, expression of sense transcripts appeared to be dependent upon latency-specific promoters located within ie1/ie2 enhancer region (Boshart, et al., 1985; Thomsen, et al., 1984) and these transcripts underwent more complex differential splicing than occurs during productive infection (Stenberg, et al., 1989). LSS1 (SEQ ID NO:42) and LSS2 (SEQ ID NO:43), were 34 and 35 bp, respectively, downstream of putative TATA elements.

The antisense transcript, which was not spliced, initiated within a region underlying ie1 exon 4 and terminated within a region underlying the first intron of sense transcripts (FIG. 10K). Although it lacked a consensus TATA element, the region upstream of the antisense transcript had a potential initiator sequence (SEQ ID NO:44) similar to that found in the human terminal deoxynucleotidyl transferase gene (Bhaumik, et al., 1994; Sorscher, et al., 1994).

The 3' RACE procedure used to clone cDNA copies of sense and antisense transcripts relied on the presence of a polyadenosine tail. Although a large proportion of the unspliced transcripts lack this modification (see above), the present analysis suggested that antisense transcript had a similar internal structure, whether polyadenylated or not. Transcripts initiating from latent infection start sites were not detected in productively infected HF cells using 5' RACE methods or using specific primers in RT-PCR.

EXAMPLE 10

Structural Comparison of Latent Transcripts

FIGS. 10A–10K illustrate a summary of latent transcript structure and predicted open reading frame (ORF) analysis. FIGS. 10A and 10B show the structures of the predominant α transcripts from the ie1/ie2 region expressed during productive infection (Stenberg, et al., 1984; Stenberg, et al., 1995; Stenberg, et al., 1989). The ie1 transcript, composed of exons 1, 2, 3 and 4, encodes a 491 aa protein (open boxes) which shares 85 amino terminal aa with the predominant ie2 transcript, composed of exons 1, 2, 3 and 5, which encodes a 579 aa protein and with a minor ie2 protein of 425 aa encoded from a more highly spliced transcript.

FIGS. 10C–10K show predominant sense and antisense CLTs determined by sequence analysis of cDNA clones. The expanded region (FIG. 10C) depicts the productive infection transcription start site (PSS; SEQ ID NO:45; Stenberg, et al., 1984; Stenberg, et al., 1985; Boshart, et al., 1985; Thomsen, et al., 1984), as well as LSS1 and LSS2. Alternative exon 5 splice region sites that were novel to the sense CLTs were as follows: 1.6/1.5 kb: 5' CCACGCGTCCTTTCAG/ GTGATTATT . . . TCGTCTTCCTCCTGCAG/ TTCGGCTTC . . . AA GATTGACGAG/GTGAGCCGCA...TTTCCCAAACAG/ GTCATGGTGCG3' (SEQ ID NO:46); 1.3/1.2 kb: CCACGCGTCCTTTCAAG/GTGATTATT . . . TTCCCAAACAG/GTCATGGTGCG (SEQ ID NO:47). Filled thick arrows denote transcripts, the 5' extensions of exon 1 detected in GM-Ps are depicted with hatched boxes, and open boxes denote ORFs that are conserved in strains Towne and AD169.

FIG. 11 shows the sequences of the LSS1, LSS2 and PSS transcription start sites in relation to one another, and in relation to a map of the ie1/ie2 locus. The Modulator, NF1 and Enhancer regions are indicated.

EXAMPLE 11

PCR Confirmation of Transcript Structure

The structure of sense and antisense transcripts was confirmed by RT-PCR using primers near the 5' and 3' ends of the transcripts and exons identified by 5' and 3' RACE.

Figure 12:
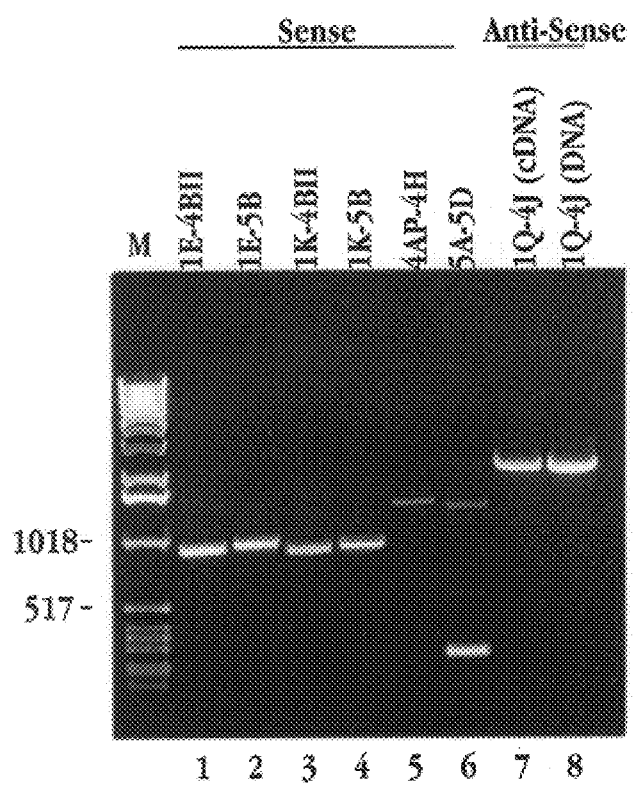
FIG. 12 shows an ethidium bromide-stained gel of RT-PCR amplifications of RNA obtained from latently infected GM-Ps.

Exemplary results are presented in FIG. 12, which shows RT-PCR amplification of RNA obtained from latently infected GM-Ps. Target cDNA used for reactions shown in lanes 1–6 was made from RNA, isolated from $10^4$ GM-Ps at four weeks PI, using random hexamer primers and "SUPERSCRIPT II" (Gibco/BRL). Target cDNA used for reactions shown in lane 7 was made from RNA, isolated from $10^5$ GM-Ps at four weeks PI, using oligo-dT and "SUPERSCRIPT II". All cDNA samples were subsequently amplified using 40 cycles PCR with the "GENEAMP XL" PCR kit using B cycle parameters (Example 7) and compared to $10^5$ copies of viral DNA amplified in the same manner (lane 8).

Forty pmol of the following primers were used for PCR: lane 1, IEP1E (SEQ ID NO:8) and IEP4BII (SEQ ID NO:25); lane 2, IEP1E (SEQ ID NO:8) and IEP5B (SEQ ID NO:30); lane 3, IEP1K (SEQ ID NO:11) and IEP4BII (SEQ ID NO:25); lane 4, IEP1K (SEQ ID NO:11) and IEP5B (SEQ ID NO:30); lane 5, IEP4AP (SEQ ID NO:24) and IEP4H (SEQ ID NO:27); lane 6, IEP5AP (SEQ ID NO:29) and IEP5D (SEQ ID NO:31); lanes 7 and 8, IEP1Q (SEQ ID NO:13) and IEP4J (SEQ ID NO:28).

In agreement with the cDNA analysis, sense transcripts covering the region from LSS1 to exon 4 or to exon 5, and the region within exon 4, were homogeneous (FIG. 12, lanes 1–5). Three expected PCR products between primers IEP5AP (SEQ ID NO:29) and IEP5D (SEQ ID NO:31) (1300, 550, and 250 bp) confirmed the alternatively spliced forms of exon 5 (FIG. 12, lane 6), and suggested that the most highly spliced form of exon 5 predominated. The antisense transcript was confirmed to be homogeneous and unspliced (FIG. 12, lanes 7 and 8).

EXAMPLE 12

RNAse Protection Assays

The transcription start site usage in sense and antisense transcripts was confirmed by RNAse protection analysis.

Probes for RNase protection were prepared by cloning PCR fragments amplified from human CMV (RC256) DNA (Spaete and Mocarski, 1987) with either IEP1H (SEQ ID NO:10) and IEP1S (SEQ ID NO:14) or IEP4H (SEQ ID NO:27) and IEP4C (SEQ ID NO:26) into the pGEM-T vector using the TA-cloning kit (Promega), resulting in pON2233 and pON2234, respectively. $^{32}$P-labeled RNA (572 nt Probe 1 for sense transcript analysis from pON2233 or 603 nt Probe 2 for antisense transcript analysis from pON2234) was made using the "MAXISCRIPT" in vitro transcription kit (Ambion, Austin, Tex.) using T7 RNA polymerase and $^{32}$P-UTP (Amersham).

The RNAse protection assays were done using the "RPA II" RNase protection assay kit (Ambion) using $10^5$ cpm of in vitro-synthesized RNA probes (above), and the recommended protocol. Following electrophoresis in an 8 M urea/5% polyacrylamide gel (Sambrook, et al., 1989), radio-labeled species were detected by autoradiography on Kodak XAR film with a 2 day exposure.

Figure 13:
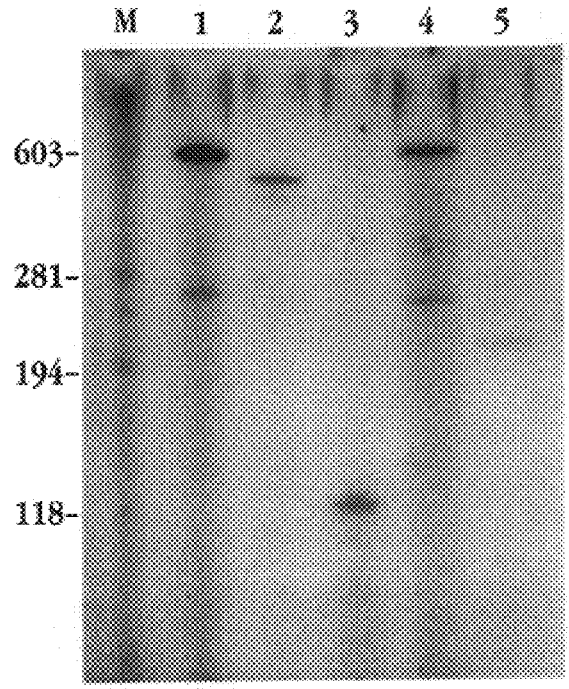
FIG. 13 shows an autoradiograph of RNase protection analysis of latent transcripts.

The results are shown in FIG. 13. RNA was extracted from $10^6$ infected GM-Ps (lanes 2 and 5) or $10^3$ infected HF cells (lane 3) as described above. Lane M, 5'-end labeled φX174 DNA HaeIII digest; lane 1, Probe 1, alone; lane 2, RNA from infected GM-Ps (4 weeks PI) hybridized with Probe 1 and RNase digested; lane 3, RNA from infected HF (2 h PI) hybridized with Probe 1 and RNase digested; 4, Probe 2 alone; lane 5, RNA from infected GM-Ps hybridized with Probe 2 and RNase digested.

Protected species of 470 and 420 nt were observed (FIG. 13, lane 2) in reactions designed to detect the 5'-ends of sense transcripts (Probe 1, 572 nt), with the longer (LSS1) transcript predominating. RNase assays of antisense transcript using Probe 2 (603 nt) protected a 220 nt species (FIG. 13, lane 5), which was consistent with the 5' RACE mapping experiments detailed above. As expected, a 120 nt protected species was detected using RNA from productively infected cells (FIG. 13, lane 3). Transcripts starting from PSS were not detected in latently infected GM-Ps, and transcripts starting from LSS1 or LSS2 were not observed in productively infected HF cells.

From these data, the use of LSS1 and LSS2 as transcription start sites on the sense transcript, as well as the presence of the antisense transcript, appear to be latency-specific.

EXAMPLE 13

Detection of CLTs in Bone Marrow of Healths Donors

Bone marrow (BM) from healthy adult donors at Stanford University Hospital (Stanford, Calif.) was tested for the presence of CLTs. The expression of sense and antisense CLTs was examined by RT-PCR amplification with nested primer sets in 15 adult BM donors whose CMV serological status was unknown at the time of transcript analysis.

Following isolation of hematopoietic cells from 3 ml of BM (approximately $3 \times 10^7$ of cells) by density sedimentation on "LYMPHOPREP" (Gibco/BRL), RNA was isolated by guanidine isothiocyanate lysis and sedimentation through a CsCl cushion (Chirgwin, et al., 1979) and, following suspension, was treated with RNase-free RQ1 DNase as described above. RNA was further purified on an "RNE-ASY" total RNA kit (Qiagen, Chatsworth, Calif.) according to manufacturer's protocol.

Purified RNA was divided into three tubes and cDNA was synthesized using random hexamer primers for sense CLT and UL112/113, or primer IEP2E (SEQ ID NO:17) for antisense CLT, in conjunction with "SUPERSCRIPT II" using the manufacturer's protocol. For the sense CLT, which is spliced, nested amplification was carried out first with primers IEP1K (SEQ ID NO:11) and IEP3D (SEQ ID NO:21) for 30 cycles and then with primers IEP1G (SEQ ID NO:9) and IEP2D (SEQ ID NO:16) (predicted product of 206 bp) for 30 cycles using B cycle parameters.

For the antisense CLT, which is unspliced, a nested amplification was carried out first with primers IEP2AII (SEQ ID NO:15) and IEP4J (SEQ ID NO:28) for 30 cycles, and then with primers IEP3C (SEQ ID NO:20) and IEP4BII (SEQ ID NO:25) (predicted product of 387 bp) for 30 cycles using B cycle parameters. For the spliced UL112/113 transcript, an asymmetric nested amplification was carried out first with primers 112A (SEQ ID NO:1) and 113B (SEQ ID NO:2) (4) for 30 cycles (predicted product of 228 bp), and then with primers 113D (SEQ ID NO:3) and 112A (SEQ ID NO:1) (4) for 30 cycles (predicted product of 150 bp) using A cycle parameters.

Products of RT-PCR were separated by electrophoresis in 2.5% agarose gels and samples were visualized either by staining with ethidium bromide (FIGS. 14A, 15A and 16A), or after transfer to "HYBRIDON-N$^+$" membrane and hybridization with $\gamma^{32}$P-ATP (Amersham) end-labeled oligonucleotide probes. Probes used were IEP1M (SEQ ID NO:12; FIG. 14B), IEP4AP (SEQ ID NO:24; FIG. 15B), or $^{32}$P dCTP (Amersham) random-primed-labeled UL112/113 probe (FIG. 16B). Lane M is HaeIII digested φX174 DNA.

Figure 14A:
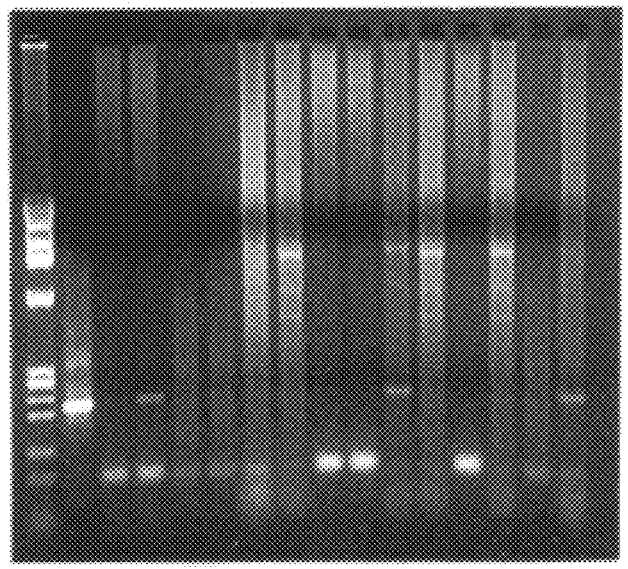
FIGS. 14A and 14B show an ethidium bromide-stained gel (FIG. 14A) and an autoradiograph (FIG. 14B) of sense CMV latent transcript (CLT) gene expression from RT-PCR analysis of latent transcripts and delayed early ($\beta$) gene expression in healthy adult donor bone marrow.
Figure 14B:
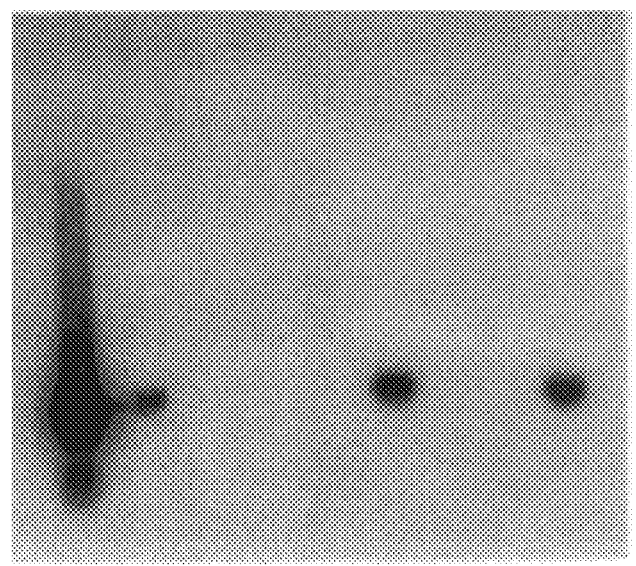
Figure 15A:
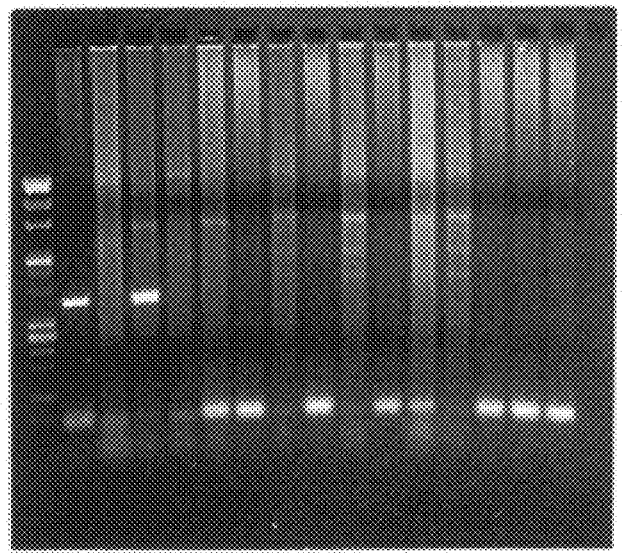
FIGS. 15A and 15B show an ethidium bromide-stained gel (FIG. 15A) and an autoradiograph (FIG. 15B) of antisense CLT gene expression from RT-PCR analysis of latent transcripts and delayed early ($\beta$) gene expression in healthy adult donor bone marrow.
Figure 15B:
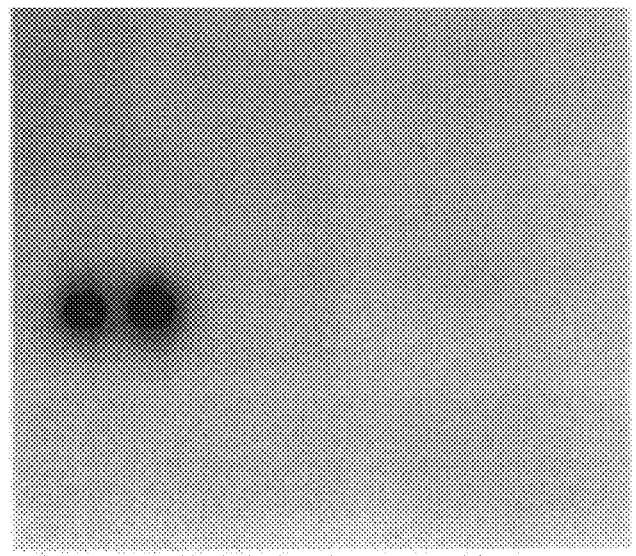
Figure 16A:
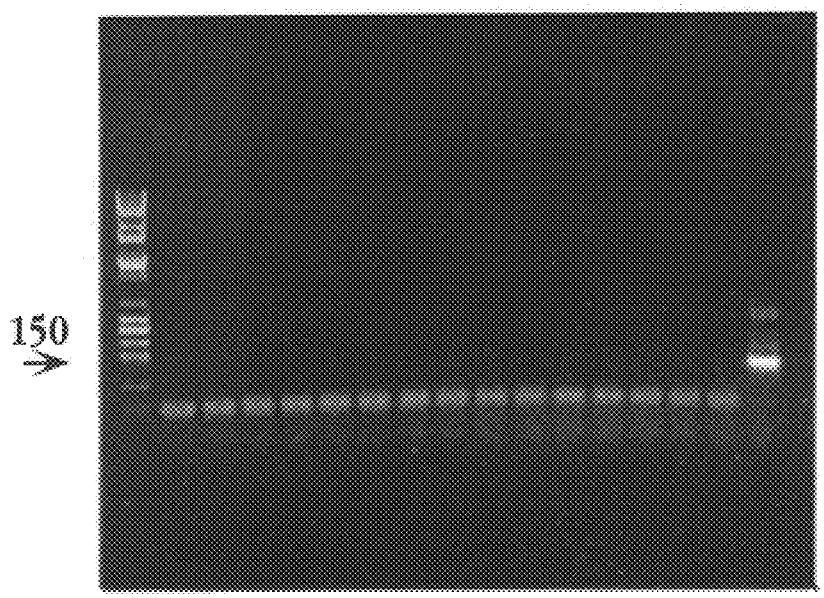
FIGS. 16A and 16B show an ethidium bromide-stained gel (FIG. 16A) and an autoradiograph (FIG. 16B) of UL112/113 gene expression from RT-PCR analysis of latent transcripts and delayed early ($\beta$) gene expression in healthy adult donor bone marrow.
Figure 16B:
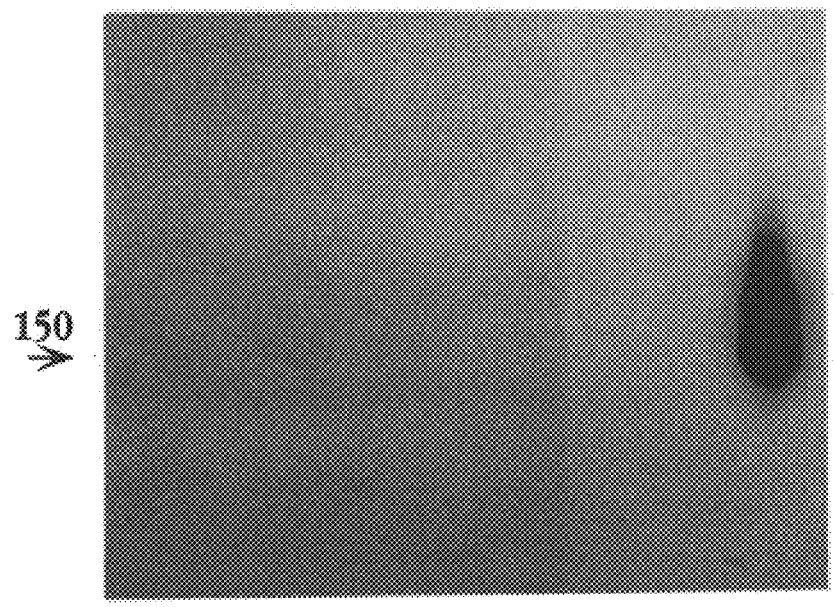
Figure 17A:
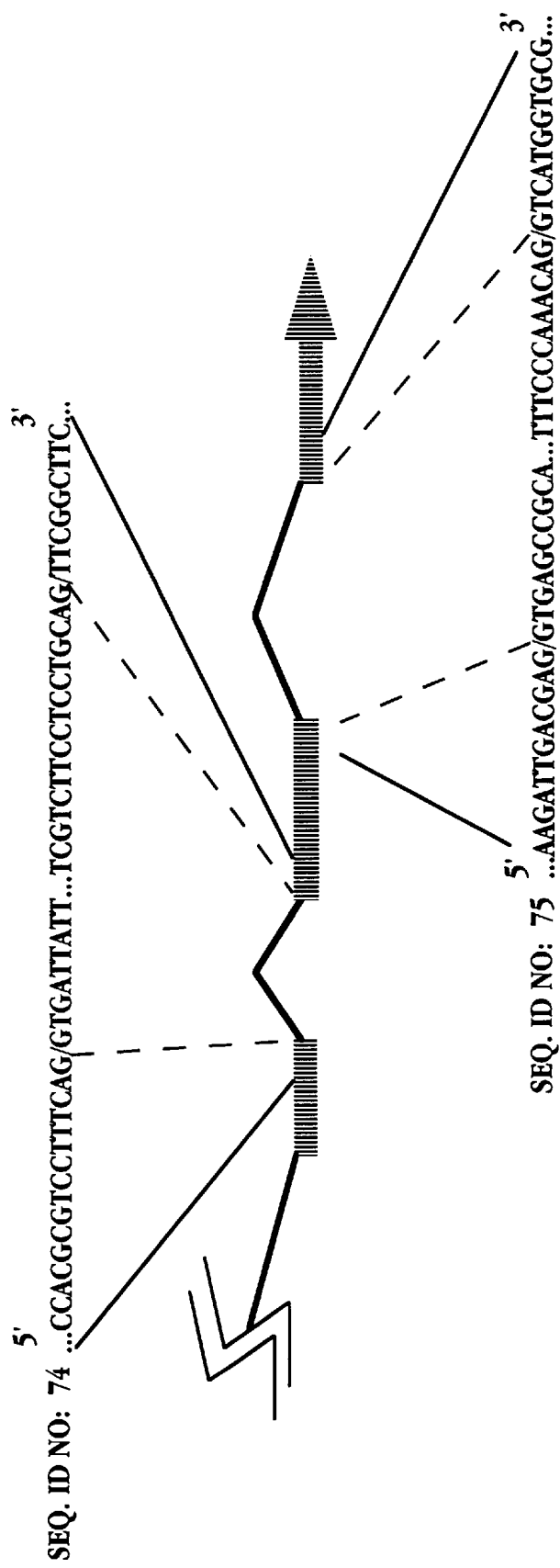
FIG. 17A shows the sequences present at the novel (latent transcript) splice junctions of the sense 1.5/1.6 kb transcripts.
Figure 17B:
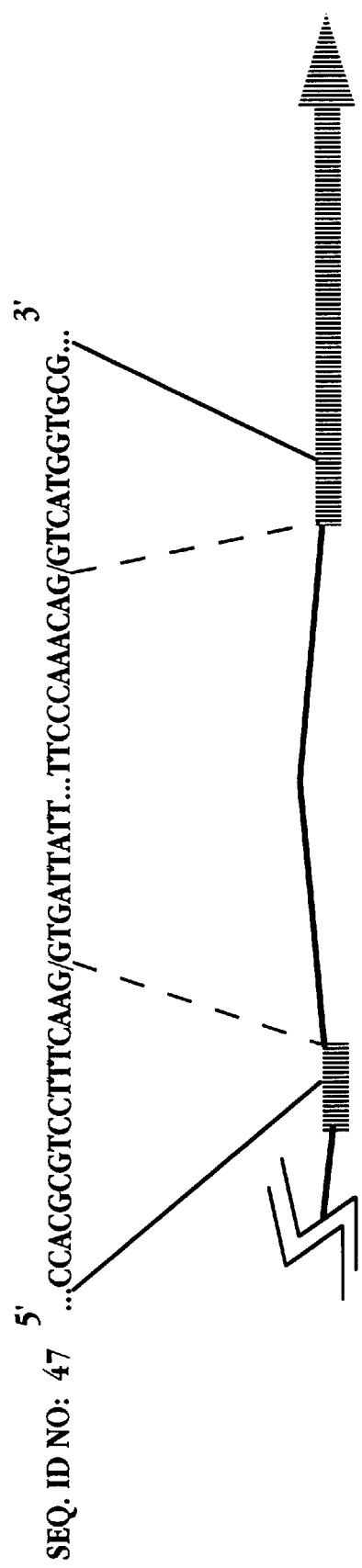
FIG. 17B shows the sequences present at the novel (latent transcript) splice junctions of the sense 1.2/1.3 kb transcripts.

Lanes 1–15 in FIGS. 14A, 14B, 15A, 15B, 16A, and 16B represent samples from donors (Stanford patient numbers (SPNs) 841, 854, 858, 865, 872, 878, 900, 904, 907, 935, 936, 972, 991, 957, and 987, respectively. Lane P in FIGS. 16A and 16B shows the RT-PCR product using RNA isolated from one infected HF cell (8 h postinfection) mixed with RNA from $10^7$ BM cells from a CMV seronegative donor.

Sense transcripts were amplified from random-primed cDNA using latency specific primers (IEP1K (SEQ ID NO:11) and IEP3D (SEQ ID NO:21) followed by IEP1G (SEQ ID NO:9) and IEP2D (SEQ ID NO:16)) and were detected in 5 out of 15 donors (FIGS. 14A and 14B). Antisense CLT was first amplified from cDNA which was synthesized using IEP2E (SEQ ID NO:17), and then subsequently amplified by PCR using a nested primer set (IEP2AII—SEQ ID NO:15 and IEP4J—SEQ ID NO:28, followed by IEP3C—SEQ ID NO:20 and IEP4BII—SEQ ID NO:25). PCR reaction product was detectable in 2 out of 15 donors (FIGS. 15A and 15B). A summary of the results is presented in Table 4, below.

TABLE 4

CYTOMEGALOVIRUS LATENT TRANSCRIPTS AND CMV SEROLOGICAL STATUS IN HEALTHY ADULT BONE MARROW DONORS

| Donor (SPN) | Sense CLT | Antisense CLT | CMV Serological Status | Gender | Age |
| --- | --- | --- | --- | --- | --- |
| 841 | + | + | + | M | 34 |
| 854 | + | − | + | M | 39 |
| 858 | + | + | + | M | 39 |
| 865 | − | − | − | F | 29 |
| 872 | − | − | + | M | 45 |
| 878 | − | − | − | M | 28 |
| 900 | − | − | − | M | 40 |
| 904 | − | − | + | F | 28 |
| 907 | − | − | − | F | 26 |
| 935 | + | − | + | F | 47 |
| 936 | − | − | − | M | 36 |
| 969 | − | − | − | F | 49 |
| 991 | − | − | N.D.* | F | 37 |
| 957 | − | − | − | M | 39 |
| 987 | + | − | + | F | 38 |

*N.D., not determined.

When the serological status of the donors was revealed, seven were found to be CMV seropositive, with sense and antisense latent transcripts detected in two, and sense alone detected in three of these seven (Table 4). These transcripts were detected only in seropositive donors and not in any of the six seronegative donors. Although anti-sense CLT predominated in the experimental GM-P latent infection, sense CLT seemed to predominate in natural latent infection of bone marrow. Early gene expression (UL112/113) and cocultivation with HF cells were performed to confirm that these donors were latently rather than productively infected. UL112/113 expression was not detected in any donor (FIGS. 16A and 16B), and virus was not recovered after cocultivation for more than a month with HF cells.

The five sense CLT-positive samples were also subjected to RT-PCR analysis with nested primer sets for two other CMV α gene transcripts (UL36 and TRS1) and were found to be negative. Although two of the recipients (936 and 987) in this group of patients needed pre-emptive ganciclovir therapy because virus was isolated following bronchial lavage, none of the recipients of either seropositive or seronegative donor samples succumbed to CMV disease.

EXAMPLE 14

Preparation of Anti-CMV Latency Associated Protein Antibody

A. Expression of Latency-Associated Polypeptide.

A DNA fragment encoding a selected latency-associated polypeptide (e.g., SEQ ID NO:62 or SEQ ID NO:66) is introduced into a pGEX expression vector (Smith, 1985, 1988), for example, pGEX-KG (Guan and Dixon).

The plasmid pGEX-KG was derived from the pGEX-2T plasmid (Pharmacia Biotech, Piscataway, N.J.) by incorporation of an EcoRI fragment encoding a nine amino-acid glycine-rich linker (Guan and Dixon). The pGEX-2T plasmid was designed for inducible, high level intracellular expression of genes or gene fragments as fusions with Schistosoma japonicum glutathione S-transferase (Sj26 or GST; Smith, et al., 1985). It contains a tac promoter for chemically-inducible expression, the GST gene, a thrombin protease recognition site, a multiple cloning site, an ampicillin resistance gene, a pBR322 ori, and an internal lac Iq gene.

The resultant vector containing latency-associated polypeptide coding sequences is used to transform XL-1 Blue *E. coli* cells (Stratagene, La Jolla, Calif.). Bacterial clones containing the protein sequences are selected and grown at 37° C., with vigorous agitation, for approximately 4 hours in 1-liter of liquid culture. One ml of 100 mM isopropyl-1-thio-β-D-galactoside (IPTG) is added to induce protein expression, and the culture is incubated for approximately another two hours.

The cells are pelleted and resuspended in 10 ml ice-cold phosphate-buffered saline, lysed until translucent, centrifuged briefly to pellet cellular debris, and the supernatant transferred to a fresh tube.

Five ml of a 50% (v/v) slurry of pre-swelled glutathione-agarose beads are added to the supernatant and mixed gently for approximately 1 hour at room temperature to allow fusion protein in the supernatant to bind to the beads. The beads are then washed three times to remove any unbound protein. Each wash consists of adding 10 ml PBS, mixing, and centrifuging in a table-top centrifuge for ~5 minutes at maximum speed (2000×g) to collect the beads.

The fusion protein itself can be eluted from the beads. Alternatively, the latency-associated polypeptide portion of the fusion protein can be eluted using the thrombin cleavage protocol (Ausubel, et al.). In the cleavage protocol, 10–20 ml of the bead slurry are combined with 10 ml Cleavage Buffer and incubated at 25° C. for about 1 hour.

Phenylmethylsulfonyl fluoride (0.6 mM final concentration) is then added to the protein elution, and the sample is concentrated to 0.5 ml using a "CENTRIPREP" concentrator (Amicon Inc., Beverly, Mass.). The protein is further purified by gel filtration.

Protein concentrations are estimated by Coomassie blue staining of protein bands after sodium dodecyl sulphate polyacrylamide gel electrophoresis (SDS-PAGE) using bovine serum albumin as a standard.

B. Antibodies Against the Latency-associated Polypeptide.

The purified fused protein is injected subcutaneously in Freund's adjuvant in a rabbit. Approximately 1 mg of fused protein is injected at days 0 and 21, and rabbit serum collected on days 42 and 56.

Minilysates from the following bacterial cultures are prepared: (1) bacterial cells infected with pGEX, (2) bacterial cells infected with pGEX containing the latency-associated polypeptide insert, and (3) bacterial cells infected with lambda gt11 containing the latency-associated polypeptide insert. The minilysates and a β-galactosidase protein control are fractionated by SDS-PAGE, and the bands transferred to nitrocellulose filters for Western blotting (Ausubel, et al.).

The expected results are summarized as follows. Serum from control (Sj26) rabbits is immunoreactive with each of the Sj26 and Sj26 fused protein antigens. Serum from the animal immunized with Sj26 fused protein is reactive with all Sj-26 antigens and with the β-galactosidase fusion protein from lambda gt11, indicating the presence of specific immunoreaction with a latency-associated polypeptide antigen. None of the sera are immunoreactive with beta-galactosidase (obtained from a commercial source).

Anti-latency-associated-polypeptide antibodies present in the sera from the animal immunized with the latency-associated polypeptide fusion protein can be purified by affinity chromatography.

While the invention has been described with reference to specific methods and embodiments, it is appreciated that various modifications and changes may be made without departing from the invention.

It is claimed:

1. A purified polypeptide encoded by a cytomegalovirus (CMV) DNA sequence produced specifically during latent infection, where the polypeptide is selected from the group consisting of SEQ ID NO:65, SEQ ID NO:67, SEQ ID NO:69 and SEQ ID NO:73.

2. A purified polypeptide encoded by a cytomegalovirus (CMV) DNA sequence produced specifically during latent infection, where the CMV transcription start site is SEQ ID NO:36 or SEQ ID NO:37.

3. A purified polypeptide encoded by a cytomegalovirus (CMV) DNA sequence produced specifically during latent infection, where said polypeptide is selected from the group consisting of SEQ ID NO:59, SEQ ID NO:61 and SEQ ID NO:63.

* * * * *

```
                              SEQUENCE LISTING (1) GENERAL INFORMATION:

(iii) NUMBER OF SEQUENCES: 75

(2) INFORMATION FOR SEQ ID NO:1:

(i) SEQUENCE CHARACTERISTICS:
          (A) LENGTH: 25 base pairs
          (B) TYPE: nucleic acid
          (C) STRANDEDNESS: single
          (D) TOPOLOGY: linear (ii) MOLECULE TYPE: DNA (iii) HYPOTHETICAL: NO (iv) ANTI-SENSE: NO (vi) ORIGINAL SOURCE:
          (C) INDIVIDUAL ISOLATE: PRIMER 112A (xi) SEQUENCE DESCRIPTION: SEQ ID NO:1:

CCGGTTGATG AACCGGCAGA AGGAG                                             25

(2) INFORMATION FOR SEQ ID NO:2:

(i) SEQUENCE CHARACTERISTICS:
          (A) LENGTH: 25 base pairs
```

(B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (vi) ORIGINAL SOURCE:
         (C) INDIVIDUAL ISOLATE: PRIMER 113B (xi) SEQUENCE DESCRIPTION: SEQ ID NO:2:

GAAAGGCCAC CGCTTCAGAC GTGTC                                              25

(2) INFORMATION FOR SEQ ID NO:3:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
         (C) INDIVIDUAL ISOLATE: PRIMER 113D (xi) SEQUENCE DESCRIPTION: SEQ ID NO:3:

GGACTGCTGC TCCGTCTCGT TCTTG                                              25

(2) INFORMATION FOR SEQ ID NO:4:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
         (C) INDIVIDUAL ISOLATE: PRIMER 2.7A (xi) SEQUENCE DESCRIPTION: SEQ ID NO:4:

CGGATTATCA TTTCCCTCTC CTACC                                              25

(2) INFORMATION FOR SEQ ID NO:5:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
         (C) INDIVIDUAL ISOLATE: PRIMER 2.7B (xi) SEQUENCE DESCRIPTION: SEQ ID NO:5:

CCTTGCGGAT TGACATTCTT GGTGGT                                              26

(2) INFORMATION FOR SEQ ID NO:6:

(i) SEQUENCE CHARACTERISTICS:
      (A) LENGTH: 33 base pairs
      (B) TYPE: nucleic acid
      (C) STRANDEDNESS: single
      (D) TOPOLOGY: linear (ii) MOLECULE TYPE: DNA (iii) HYPOTHETICAL: NO (iv) ANTI-SENSE: NO (vi) ORIGINAL SOURCE:
      (C) INDIVIDUAL ISOLATE: PRIMER IEP1B (xi) SEQUENCE DESCRIPTION: SEQ ID NO:6:

CGGTTCACTA AACGAGCTCT GCTTATATAG ACC                                      33

(2) INFORMATION FOR SEQ ID NO:7:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: DNA (iii) HYPOTHETICAL: NO (iv) ANTI-SENSE: NO (vi) ORIGINAL SOURCE:
      (C) INDIVIDUAL ISOLATE: PRIMER IEP1D (xi) SEQUENCE DESCRIPTION: SEQ ID NO:7:

ATACGTAGAT GTACTGCCAA GTAGG                                               25

(2) INFORMATION FOR SEQ ID NO:8:

(i) SEQUENCE CHARACTERISTICS:
      (A) LENGTH: 26 base pairs
      (B) TYPE: nucleic acid
      (C) STRANDEDNESS: single
      (D) TOPOLOGY: linear (ii) MOLECULE TYPE: DNA (iii) HYPOTHETICAL: NO (iv) ANTI-SENSE: NO (vi) ORIGINAL SOURCE:
      (C) INDIVIDUAL ISOLATE: PRIMER IEP1E (xi) SEQUENCE DESCRIPTION: SEQ ID NO:8:

GTATCATATG CCAAGTCCGC CCCCTA                                              26

(2) INFORMATION FOR SEQ ID NO:9:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: DNA (iii) HYPOTHETICAL: NO (iv) ANTI-SENSE: NO (vi) ORIGINAL SOURCE:
            (C) INDIVIDUAL ISOLATE: PRIMER IEP1G (xi) SEQUENCE DESCRIPTION: SEQ ID NO:9:

ATAGCAGAGC TCGTTTAGTG AACCG                                            25

(2) INFORMATION FOR SEQ ID NO:10:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (vi) ORIGINAL SOURCE:
            (C) INDIVIDUAL ISOLATE: PRIMER IEP1H (xi) SEQUENCE DESCRIPTION: SEQ ID NO:10:

GTCACTCTTG GCACGGGGAA TCCGCGTTCC                                        30

(2) INFORMATION FOR SEQ ID NO:11:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (vi) ORIGINAL SOURCE:
            (C) INDIVIDUAL ISOLATE: PRIMER IEP1K (xi) SEQUENCE DESCRIPTION: SEQ ID NO:11:

ATGCCCAGTA CATGACCTTA CGGG                                             24

(2) INFORMATION FOR SEQ ID NO:12:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (vi) ORIGINAL SOURCE:
            (C) INDIVIDUAL ISOLATE: PRIMER IEP1M (xi) SEQUENCE DESCRIPTION: SEQ ID NO:12:

TCAGATCGCC TGGAGACGCC ATCC                                             24

(2) INFORMATION FOR SEQ ID NO:13:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: PRIMER IEP1Q (xi) SEQUENCE DESCRIPTION: SEQ ID NO:13:

ACAGGATGGG GTCTCATTTA TTATTTACAA ATTC                                    34

(2) INFORMATION FOR SEQ ID NO:14:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: PRIMER IEP1S (xi) SEQUENCE DESCRIPTION: SEQ ID NO:14:

TGACGTATGT TCCCATAGTA ACGC                                                   24

(2) INFORMATION FOR SEQ ID NO:15:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: PRIMER IEP2AII (xi) SEQUENCE DESCRIPTION: SEQ ID NO:15:

ATGGAGTCCT CTGCCAAGAG AAAGATGGAC                                        30

(2) INFORMATION FOR SEQ ID NO:16:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (iii) HYPOTHETICAL: NO

```
        (iv) ANTI-SENSE: NO (vi) ORIGINAL SOURCE:
             (C) INDIVIDUAL ISOLATE: PRIMER IEP2D (xi) SEQUENCE DESCRIPTION: SEQ ID NO:16:

CAGGATTATC AGGGTCCATC TTTCTCTTGG                                    30

(2) INFORMATION FOR SEQ ID NO:17:

(i) SEQUENCE CHARACTERISTICS:
             (A) LENGTH: 15 base pairs
             (B) TYPE: nucleic acid
             (C) STRANDEDNESS: single
             (D) TOPOLOGY: linear (ii) MOLECULE TYPE: DNA (iii) HYPOTHETICAL: NO (iv) ANTI-SENSE: NO (vi) ORIGINAL SOURCE:
             (C) INDIVIDUAL ISOLATE: PRIMER IEP2E (xi) SEQUENCE DESCRIPTION: SEQ ID NO:17:

TCACCGTCCT TGACA                                                    15

(2) INFORMATION FOR SEQ ID NO:18:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: DNA (iii) HYPOTHETICAL: NO (iv) ANTI-SENSE: NO (vi) ORIGINAL SOURCE:
             (C) INDIVIDUAL ISOLATE: PRIMER IEP3A (xi) SEQUENCE DESCRIPTION: SEQ ID NO:18:

GTGACCAAGG CCACGACGTT                                               20

(2) INFORMATION FOR SEQ ID NO:19:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: DNA (iii) HYPOTHETICAL: NO (iv) ANTI-SENSE: NO (vi) ORIGINAL SOURCE:
             (C) INDIVIDUAL ISOLATE: PRIMER IEP3B (xi) SEQUENCE DESCRIPTION: SEQ ID NO:19:

TCTGCCAGGA CATCTTTCTC                                               20

(2) INFORMATION FOR SEQ ID NO:20:

(i) SEQUENCE CHARACTERISTICS:
```

(A) LENGTH: 25 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: PRIMER IEP3C (xi) SEQUENCE DESCRIPTION: SEQ ID NO:20:

CAACGAGAAC CCCGAGAAAG ATGTC                                              25

(2) INFORMATION FOR SEQ ID NO:21:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: PRIMER IEP3D (xi) SEQUENCE DESCRIPTION: SEQ ID NO:21:

CCAGACTCAG CTGACTGTTA ACCTCCTTCC                                         30

(2) INFORMATION FOR SEQ ID NO:22:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: PRIMER IEP3E (xi) SEQUENCE DESCRIPTION: SEQ ID NO:22:

TAGCGATAAA TGAGTCAGGA GGACG                                              25

(2) INFORMATION FOR SEQ ID NO:23:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: PRIMER IEP3G (xi) SEQUENCE DESCRIPTION: SEQ ID NO:23:

TATGTGTTGT TATCCTCCTC TACAG                                        25

(2) INFORMATION FOR SEQ ID NO:24:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: PRIMER IEP4AP (xi) SEQUENCE DESCRIPTION: SEQ ID NO:24:

ACAGATTAAG GTTCGAGTGG ACATGGTGCG                                   30

(2) INFORMATION FOR SEQ ID NO:25:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: PRIMER IEP4BII (xi) SEQUENCE DESCRIPTION: SEQ ID NO:25:

CAATACACTT CATCTCCTCG AAAGG                                        25

(2) INFORMATION FOR SEQ ID NO:26:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: PRIMER IEP4C (xi) SEQUENCE DESCRIPTION: SEQ ID NO:26:

CCTGAGGTTA TCAGTGTAAT GAAGC                                        25

(2) INFORMATION FOR SEQ ID NO:27:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
              (C) INDIVIDUAL ISOLATE: PRIMER IEP4H (xi) SEQUENCE DESCRIPTION: SEQ ID NO:27:

ACGGTTTCAC AGGCGTGACA CGTTTATTGA G                                              31

(2) INFORMATION FOR SEQ ID NO:28:

(i) SEQUENCE CHARACTERISTICS:
              (A) LENGTH: 28 base pairs
              (B) TYPE: nucleic acid
              (C) STRANDEDNESS: single
              (D) TOPOLOGY: linear (ii) MOLECULE TYPE: DNA (iii) HYPOTHETICAL: NO (iv) ANTI-SENSE: NO (vi) ORIGINAL SOURCE:
              (C) INDIVIDUAL ISOLATE: PRIMER IEP4J (xi) SEQUENCE DESCRIPTION: SEQ ID NO:28:

GTGACACCAG AGAATCAGAG GAGCTGAC                                                  28

(2) INFORMATION FOR SEQ ID NO:29:

(i) SEQUENCE CHARACTERISTICS:
              (A) LENGTH: 30 base pairs
              (B) TYPE: nucleic acid
              (C) STRANDEDNESS: single
              (D) TOPOLOGY: linear (ii) MOLECULE TYPE: DNA (iii) HYPOTHETICAL: NO (iv) ANTI-SENSE: NO (vi) ORIGINAL SOURCE:
              (C) INDIVIDUAL ISOLATE: PRIMER IEP5AP (xi) SEQUENCE DESCRIPTION: SEQ ID NO:29:

CAATCATGCC GGTATCGATT CCAGTAGCAC                                                30

(2) INFORMATION FOR SEQ ID NO:30:

(i) SEQUENCE CHARACTERISTICS:
              (A) LENGTH: 25 base pairs
              (B) TYPE: nucleic acid
              (C) STRANDEDNESS: single
              (D) TOPOLOGY: linear (ii) MOLECULE TYPE: DNA (iii) HYPOTHETICAL: NO (iv) ANTI-SENSE: NO (vi) ORIGINAL SOURCE:
              (C) INDIVIDUAL ISOLATE: PRIMER IEP5B (xi) SEQUENCE DESCRIPTION: SEQ ID NO:30:

GCGTGGTTTT GCGCGGTTTC TTACG                                                     25

(2) INFORMATION FOR SEQ ID NO:31:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: PRIMER IEP5D (xi) SEQUENCE DESCRIPTION: SEQ ID NO:31:

CCACCCTGGT TGGTGGAGAA GATGC    25

(2) INFORMATION FOR SEQ ID NO:32:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: PRIMER IEP5H (xi) SEQUENCE DESCRIPTION: SEQ ID NO:32:

CTTATCTTTC ATGATATTGC GCACCTTCTC G    31

(2) INFORMATION FOR SEQ ID NO:33:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: PRIMER N1

(xi) SEQUENCE DESCRIPTION: SEQ ID NO:33:

GCTGGGTAGT CCCCACCTTT CTAGA    25

(2) INFORMATION FOR SEQ ID NO:34:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (iii) HYPOTHETICAL: NO

```
        (iv) ANTI-SENSE: NO (vi) ORIGINAL SOURCE:
             (C) INDIVIDUAL ISOLATE: PRIMER N2

(xi) SEQUENCE DESCRIPTION: SEQ ID NO:34:

CTTATGAGTA TTTCTTCCAG GGTACTCGAG                                              30

(2) INFORMATION FOR SEQ ID NO:35:

(i) SEQUENCE CHARACTERISTICS:
            (A) LENGTH: 73 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (vi) ORIGINAL SOURCE:
             (C) INDIVIDUAL ISOLATE: PRIMER RL-1

(xi) SEQUENCE DESCRIPTION: SEQ ID NO:35:

CTTATGAGTA TTTCTTCCAG GGTACTCGAG GCTGGGTAGT CCCCACCTTT CTAGATTTTT            60

TTTTTTTTTT TTT                                                              73

(2) INFORMATION FOR SEQ ID NO:36:

(i) SEQUENCE CHARACTERISTICS:
            (A) LENGTH: 19 base pairs
            (B) TYPE: nucleic acid
            (C) STRANDEDNESS: both
            (D) TOPOLOGY: unknown (ii) MOLECULE TYPE: DNA (genomic)

(iii) HYPOTHETICAL: NO (iv) ANTI-SENSE: NO (vi) ORIGINAL SOURCE:
             (C) INDIVIDUAL ISOLATE: LSS1 transcription start site (ix) FEATURE:
             (A) NAME/KEY: misc_feature
             (B) LOCATION: 0..1
             (D) OTHER INFORMATION: /note= "between 0 and 1, where "+1"
                 corresponds to nt 173,259 on the AD169 genome sequence"

(ix) FEATURE:
             (A) NAME/KEY: misc_feature
             (B) LOCATION: 19...
             (D) OTHER INFORMATION: /note= "after 19, "..."″

(xi) SEQUENCE DESCRIPTION: SEQ ID NO:36:

GTATCATATG CCAAGTACG                                                         19

(2) INFORMATION FOR SEQ ID NO:37:

(i) SEQUENCE CHARACTERISTICS:
            (A) LENGTH: 19 base pairs
            (B) TYPE: nucleic acid
            (C) STRANDEDNESS: both
            (D) TOPOLOGY: unknown (ii) MOLECULE TYPE: DNA (genomic)

(iii) HYPOTHETICAL: NO
```

```
    (iv) ANTI-SENSE: NO (vi) ORIGINAL SOURCE:
         (C) INDIVIDUAL ISOLATE: LSS2 transcription start site (ix) FEATURE:
         (A) NAME/KEY: misc_feature
         (B) LOCATION: 0..1
         (D) OTHER INFORMATION: /note= "between 0 and 1, where "+1"
             corresponds to nt 173,195 on AD169"

(ix) FEATURE:
         (A) NAME/KEY: misc_feature
         (B) LOCATION: 19...
         (D) OTHER INFORMATION: /note= "after 19, "...""

(xi) SEQUENCE DESCRIPTION: SEQ ID NO:37:

ATGCCCAGTA CATGACCTT                                                    19

(2) INFORMATION FOR SEQ ID NO:38:

(i) SEQUENCE CHARACTERISTICS:
         (A) LENGTH: 15 base pairs
         (B) TYPE: nucleic acid
         (C) STRANDEDNESS: both
         (D) TOPOLOGY: unknown (ii) MOLECULE TYPE: DNA (genomic)

(iii) HYPOTHETICAL: NO (iv) ANTI-SENSE: NO (vi) ORIGINAL SOURCE:
         (C) INDIVIDUAL ISOLATE: Sequence where +1 corresponds to nt
             171,256 on CMV AD169

(ix) FEATURE:
         (A) NAME/KEY: misc_feature
         (B) LOCATION: 0..1
         (D) OTHER INFORMATION: /note= "between 0 and 1, where "+1"
             corresponds to nt 171,256 on AD169"

(ix) FEATURE:
         (A) NAME/KEY: misc_feature
         (B) LOCATION: 14...
         (D) OTHER INFORMATION: /note= "after 14, "...""

(xi) SEQUENCE DESCRIPTION: SEQ ID NO:38:

GTGACACCAG AGAAT                                                        15

(2) INFORMATION FOR SEQ ID NO:39:

(i) SEQUENCE CHARACTERISTICS:
         (A) LENGTH: 13 base pairs
         (B) TYPE: nucleic acid
         (C) STRANDEDNESS: both
         (D) TOPOLOGY: unknown (ii) MOLECULE TYPE: DNA (genomic)

(iii) HYPOTHETICAL: NO (iv) ANTI-SENSE: NO (ix) FEATURE:
         (A) NAME/KEY: misc_feature
         (B) LOCATION: 0..1
         (D) OTHER INFORMATION: /note= "between 0 and 1, "+1""

(ix) FEATURE:
         (A) NAME/KEY: misc_feature
         (B) LOCATION: 13...
         (D) OTHER INFORMATION: /note= "after 13, "...""
```

```
        (xi) SEQUENCE DESCRIPTION: SEQ ID NO:39:

GACACCAGAG AAT                                                          13

(2) INFORMATION FOR SEQ ID NO:40:

(i) SEQUENCE CHARACTERISTICS:
         (A) LENGTH: 9 base pairs
         (B) TYPE: nucleic acid
         (C) STRANDEDNESS: both
         (D) TOPOLOGY: unknown (ii) MOLECULE TYPE: DNA (genomic)

(iii) HYPOTHETICAL: NO (iv) ANTI-SENSE: NO (ix) FEATURE:
         (A) NAME/KEY: misc_feature
         (B) LOCATION: 0..1
         (D) OTHER INFORMATION: /note= "between 0 and 1, "+1""

(ix) FEATURE:
         (A) NAME/KEY: misc_feature
         (B) LOCATION: 9...
         (D) OTHER INFORMATION: /note= "after 9, "...""

(xi) SEQUENCE DESCRIPTION: SEQ ID NO:40:

CCAGAGAAT                                                                9

(2) INFORMATION FOR SEQ ID NO:41:

(i) SEQUENCE CHARACTERISTICS:
         (A) LENGTH: 22 base pairs
         (B) TYPE: nucleic acid
         (C) STRANDEDNESS: both
         (D) TOPOLOGY: unknown (ii) MOLECULE TYPE: DNA (genomic)

(iii) HYPOTHETICAL: NO (iv) ANTI-SENSE: NO (vi) ORIGINAL SOURCE:
         (C) INDIVIDUAL ISOLATE: Sequence where the 3' proximal T
             corresponds to nt 173,331 on AD169

(ix) FEATURE:
         (A) NAME/KEY: misc_feature
         (B) LOCATION: 0..1
         (D) OTHER INFORMATION: /note= "between 0 and 1, "...""

(ix) FEATURE:
         (A) NAME/KEY: misc_feature
         (B) LOCATION: 22...22
         (D) OTHER INFORMATION: /note= "where "A" at 22 has subscript
             "n""

(xi) SEQUENCE DESCRIPTION: SEQ ID NO:41:

ATAAATGAGA CCCCATCCTG TA                                                22

(2) INFORMATION FOR SEQ ID NO:42:

(i) SEQUENCE CHARACTERISTICS:
         (A) LENGTH: 38 base pairs
         (B) TYPE: nucleic acid
         (C) STRANDEDNESS: both
         (D) TOPOLOGY: unknown (ii) MOLECULE TYPE: DNA (genomic)
```

(iii) HYPOTHETICAL: NO (iv) ANTI-SENSE: NO (vi) ORIGINAL SOURCE:
            (C) INDIVIDUAL ISOLATE: LSS1 transcription initiation region (ix) FEATURE:
            (A) NAME/KEY: misc_feature
            (B) LOCATION: 37..38
            (D) OTHER INFORMATION: /note= "between 37 and 38, "+1""

(xi) SEQUENCE DESCRIPTION: SEQ ID NO:42:

TATTTACGGT AAACTGCCCA CTTGGAGTAC ATCAAGTG                                38

(2) INFORMATION FOR SEQ ID NO:43:

(i) SEQUENCE CHARACTERISTICS:
            (A) LENGTH: 39 base pairs
            (B) TYPE: nucleic acid
            (C) STRANDEDNESS: both
            (D) TOPOLOGY: unknown (ii) MOLECULE TYPE: DNA (genomic)

(iii) HYPOTHETICAL: NO (iv) ANTI-SENSE: NO (vi) ORIGINAL SOURCE:
            (C) INDIVIDUAL ISOLATE: LSS2 transcription initiation region (ix) FEATURE:
            (A) NAME/KEY: misc_feature
            (B) LOCATION: 38..39
            (D) OTHER INFORMATION: /note= "between 38 and 39, "+1""

(xi) SEQUENCE DESCRIPTION: SEQ ID NO:43:

TATTGACGTC AATGACGGTA AATGGCCCGC CTAGCATTA                               39

(2) INFORMATION FOR SEQ ID NO:44:

(i) SEQUENCE CHARACTERISTICS:
            (A) LENGTH: 29 base pairs
            (B) TYPE: nucleic acid
            (C) STRANDEDNESS: both
            (D) TOPOLOGY: unknown (ii) MOLECULE TYPE: DNA (genomic)

(iii) HYPOTHETICAL: NO (iv) ANTI-SENSE: YES (vi) ORIGINAL SOURCE:
            (C) INDIVIDUAL ISOLATE: Antisense transcription
                initiation region and start site (ix) FEATURE:
            (A) NAME/KEY: misc_feature
            (B) LOCATION: 14..15
            (D) OTHER INFORMATION: /note= "between 14 and 15, "+1""

(xi) SEQUENCE DESCRIPTION: SEQ ID NO:44:

CGGGGACTCT GGGGGTGACA CCAGAGAAT                                         29

(2) INFORMATION FOR SEQ ID NO:45:

(i) SEQUENCE CHARACTERISTICS:
            (A) LENGTH: 14 base pairs
            (B) TYPE: nucleic acid
            (C) STRANDEDNESS: both
            (D) TOPOLOGY: unknown

```
    (ii) MOLECULE TYPE: DNA (genomic)

(iii) HYPOTHETICAL: NO (iv) ANTI-SENSE: NO (vi) ORIGINAL SOURCE:
         (C) INDIVIDUAL ISOLATE: productive infection
             transcription start site (PSS)

(ix) FEATURE:
         (A) NAME/KEY: misc_feature
         (B) LOCATION: 0..1
         (D) OTHER INFORMATION: /note= "between 0 and 1, "+1""

(ix) FEATURE:
         (A) NAME/KEY: misc_feature
         (B) LOCATION: 14...
         (D) OTHER INFORMATION: /note= "after 14, "...""

(xi) SEQUENCE DESCRIPTION: SEQ ID NO:45:

TCAGATCGCC TGGA                                                             14

(2) INFORMATION FOR SEQ ID NO:46:

(i) SEQUENCE CHARACTERISTICS:
         (A) LENGTH: 96 base pairs
         (B) TYPE: nucleic acid
         (C) STRANDEDNESS: both
         (D) TOPOLOGY: unknown (ii) MOLECULE TYPE: DNA (genomic)

(iii) HYPOTHETICAL: NO (iv) ANTI-SENSE: NO (vi) ORIGINAL SOURCE:
         (C) INDIVIDUAL ISOLATE: Seq.:  Alternative exon 5 splice
             region sites novel to the sense 1.5/1.6 kb transcripts (ix) FEATURE:
         (A) NAME/KEY: misc_feature
         (B) LOCATION: 16..17
         (D) OTHER INFORMATION: /note= "between 16 and 17, "/""

(ix) FEATURE:
         (A) NAME/KEY: misc_feature
         (B) LOCATION: 25..26
         (D) OTHER INFORMATION: /note= "between 25 and 26, "...""

(ix) FEATURE:
         (A) NAME/KEY: misc_feature
         (B) LOCATION: 42..43
         (D) OTHER INFORMATION: /note= "between 42 and 43, "/""

(ix) FEATURE:
         (A) NAME/KEY: misc_feature
         (B) LOCATION: 51..52
         (D) OTHER INFORMATION: /note= "between 51 and 52, "...""

(ix) FEATURE:
         (A) NAME/KEY: misc_feature
         (B) LOCATION: 63..64
         (D) OTHER INFORMATION: /note= "between 63 and 64, "/""

(ix) FEATURE:
         (A) NAME/KEY: misc_feature
         (B) LOCATION: 73..74
         (D) OTHER INFORMATION: /note= "between 73 and 74, "...""

(ix) FEATURE:
         (A) NAME/KEY: misc_feature
         (B) LOCATION: 85..86
         (D) OTHER INFORMATION: /note= "between 85 and 86, "/""
```

(xi) SEQUENCE DESCRIPTION: SEQ ID NO:46:

CCACGCGTCC TTTCAGGTGA TTATTTCGTC TTCCTCCTGC AGTTCGGCTT CAAGATTGAC        60

GAGGTGAGCC GCATTTCCCA AACAGGTCAT GGTGCG        96

(2) INFORMATION FOR SEQ ID NO:47:

(i) SEQUENCE CHARACTERISTICS:
        (A) LENGTH: 48 base pairs
        (B) TYPE: nucleic acid
        (C) STRANDEDNESS: both
        (D) TOPOLOGY: unknown (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: Seq: Alternative exon 5 splice
            region site novel to the sense 1.3/1.2 kb transcripts (ix) FEATURE:
        (A) NAME/KEY: misc_feature
        (B) LOCATION: 17..18
        (D) OTHER INFORMATION: /note= "between 17 and 18, "/""

(ix) FEATURE:
        (A) NAME/KEY: misc_feature
        (B) LOCATION: 26..27
        (D) OTHER INFORMATION: /note= "between 26 and 27, "..."

(ix) FEATURE:
        (A) NAME/KEY: misc_feature
        (B) LOCATION: 37..38
        (D) OTHER INFORMATION: /note= "between 37 and 38, "/""

(xi) SEQUENCE DESCRIPTION: SEQ ID NO:47:

CCACGCGTCC TTTCAAGGTG ATTATTTTCC CAAACAGGTC ATGGTGCG        48

(2) INFORMATION FOR SEQ ID NO:48:

(i) SEQUENCE CHARACTERISTICS:
        (A) LENGTH: 26 base pairs
        (B) TYPE: nucleic acid
        (C) STRANDEDNESS: both
        (D) TOPOLOGY: unknown (ii) MOLECULE TYPE: mRNA to cDNA (iii) HYPOTHETICAL: NO (iv) ANTI-SENSE: NO (vi) ORIGINAL SOURCE:
        (C) INDIVIDUAL ISOLATE: 5' end sequence of pON2218 and pON2219

(ix) FEATURE:
        (A) NAME/KEY: misc_feature
        (B) LOCATION: 0..1
        (D) OTHER INFORMATION: /note= "between 0 and 1, "..."

(ix) FEATURE:
        (A) NAME/KEY: misc_feature
        (B) LOCATION: 26...
        (D) OTHER INFORMATION: /note= "after 26, "..."

(xi) SEQUENCE DESCRIPTION: SEQ ID NO:48:

TTTTTTTGTA TCATATGCCA AGTCCG        26

(2) INFORMATION FOR SEQ ID NO:49:

```
        (i) SEQUENCE CHARACTERISTICS:
            (A) LENGTH: 27 base pairs
            (B) TYPE: nucleic acid
            (C) STRANDEDNESS: both
            (D) TOPOLOGY: unknown (ii) MOLECULE TYPE: mRNA to cDNA (iii) HYPOTHETICAL: NO (iv) ANTI-SENSE: NO (vi) ORIGINAL SOURCE:
            (C) INDIVIDUAL ISOLATE: 5' end sequence of pON2220

(ix) FEATURE:
            (A) NAME/KEY: misc_feature
            (B) LOCATION: 0..1
            (D) OTHER INFORMATION: /note= "between 0 and 1, "...""

(ix) FEATURE:
            (A) NAME/KEY: misc_feature
            (B) LOCATION: 27...
            (D) OTHER INFORMATION: /note= "after 27, "...""

(xi) SEQUENCE DESCRIPTION: SEQ ID NO:49:

TTTTTTTGGT ATCATATGCC AAGTCCG                                               27

(2) INFORMATION FOR SEQ ID NO:50:

(i) SEQUENCE CHARACTERISTICS:
            (A) LENGTH: 26 base pairs
            (B) TYPE: nucleic acid
            (C) STRANDEDNESS: both
            (D) TOPOLOGY: unknown (ii) MOLECULE TYPE: mRNA to cDNA (iii) HYPOTHETICAL: NO (iv) ANTI-SENSE: NO (vi) ORIGINAL SOURCE:
            (C) INDIVIDUAL ISOLATE: 5' end sequence of pON2222, pON2223 and
                pON2224 at -292 relative to PSS (ix) FEATURE:
            (A) NAME/KEY: misc_feature
            (B) LOCATION: 0..1
            (D) OTHER INFORMATION: /note= "between 0 and 1, "...""

(ix) FEATURE:
            (A) NAME/KEY: misc_feature
            (B) LOCATION: 26...
            (D) OTHER INFORMATION: /note= "after 26, "...""

(xi) SEQUENCE DESCRIPTION: SEQ ID NO:50:

TTTTTTTATG CCCAGTACAT GACCTT                                                26

(2) INFORMATION FOR SEQ ID NO:51:

(i) SEQUENCE CHARACTERISTICS:
            (A) LENGTH: 28 base pairs
            (B) TYPE: nucleic acid
            (C) STRANDEDNESS: both
            (D) TOPOLOGY: unknown (ii) MOLECULE TYPE: mRNA to cDNA (iii) HYPOTHETICAL: NO (iv) ANTI-SENSE: NO (vi) ORIGINAL SOURCE:
            (C) INDIVIDUAL ISOLATE: 3' end sequence of pON2227 and pON2228
```

```
    (ix) FEATURE:
        (A) NAME/KEY: misc_feature
        (B) LOCATION: 0..1
        (D) OTHER INFORMATION: /note= "between 0 and 1, "...""

(ix) FEATURE:
        (A) NAME/KEY: misc_feature
        (B) LOCATION: 28...
        (D) OTHER INFORMATION: /note= "after 28, "...""

(xi) SEQUENCE DESCRIPTION: SEQ ID NO:51:

TTTTTTTGTG ACACCAGAGA ATCAGAGG                                              28

(2) INFORMATION FOR SEQ ID NO:52:

(i) SEQUENCE CHARACTERISTICS:
        (A) LENGTH: 23 base pairs
        (B) TYPE: nucleic acid
        (C) STRANDEDNESS: both
        (D) TOPOLOGY: unknown (ii) MOLECULE TYPE: mRNA to cDNA (iii) HYPOTHETICAL: NO (iv) ANTI-SENSE: NO (vi) ORIGINAL SOURCE:
        (C) INDIVIDUAL ISOLATE: 3' end sequence of pON2225

(ix) FEATURE:
        (A) NAME/KEY: misc_feature
        (B) LOCATION: 0..1
        (D) OTHER INFORMATION: /note= "between 0 and 1, "...""

(ix) FEATURE:
        (A) NAME/KEY: misc_feature
        (B) LOCATION: 23...
        (D) OTHER INFORMATION: /note= "after 23, "...""

(xi) SEQUENCE DESCRIPTION: SEQ ID NO:52:

TTTTTTTACC AGAGAATCAG AGG                                                   23

(2) INFORMATION FOR SEQ ID NO:53:

(i) SEQUENCE CHARACTERISTICS:
        (A) LENGTH: 26 base pairs
        (B) TYPE: nucleic acid
        (C) STRANDEDNESS: both
        (D) TOPOLOGY: unknown (ii) MOLECULE TYPE: mRNA to cDNA (iii) HYPOTHETICAL: NO (iv) ANTI-SENSE: NO (vi) ORIGINAL SOURCE:
        (C) INDIVIDUAL ISOLATE: 3' end sequence of pON2226

(ix) FEATURE:
        (A) NAME/KEY: misc_feature
        (B) LOCATION: 0..1
        (D) OTHER INFORMATION: /note= "between 0 and 1, "...""

(ix) FEATURE:
        (A) NAME/KEY: misc_feature
        (B) LOCATION: 26...
        (D) OTHER INFORMATION: /note= "after 26, "...""

(xi) SEQUENCE DESCRIPTION: SEQ ID NO:53:

TTTTTTTGAC ACCATAGAAT CAGAGG                                                26
```

(2) INFORMATION FOR SEQ ID NO:54:

(i) SEQUENCE CHARACTERISTICS:
        (A) LENGTH: 33 base pairs
        (B) TYPE: nucleic acid
        (C) STRANDEDNESS: both
        (D) TOPOLOGY: unknown (ii) MOLECULE TYPE: mRNA to cDNA (iii) HYPOTHETICAL: NO (iv) ANTI-SENSE: NO (vi) ORIGINAL SOURCE:
        (C) INDIVIDUAL ISOLATE: 3' end sequence of antisense
            transcripts of pON229, pON230, pON231, and pON232

(ix) FEATURE:
        (A) NAME/KEY: misc_feature
        (B) LOCATION: 0..1
        (D) OTHER INFORMATION: /note= "between 0 and 1, "..."""

(ix) FEATURE:
        (A) NAME/KEY: misc_feature
        (B) LOCATION: 33...
        (D) OTHER INFORMATION: /note= "after 33, "..."""

(xi) SEQUENCE DESCRIPTION: SEQ ID NO:54:

```
AAATAATAAA TGAGACCCCA TCCTGTAAAA AAA                                33
```

(2) INFORMATION FOR SEQ ID NO:55:

(i) SEQUENCE CHARACTERISTICS:
        (A) LENGTH: 28 base pairs
        (B) TYPE: nucleic acid
        (C) STRANDEDNESS: both
        (D) TOPOLOGY: unknown (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: Seq. PSS (ix) FEATURE:
        (A) NAME/KEY: misc_feature
        (B) LOCATION: 27..28
        (D) OTHER INFORMATION: /note= "between 27 and 28, "+1"""

(xi) SEQUENCE DESCRIPTION: SEQ ID NO:55:

```
TATAAGCAGA GCTCGTTTAG TGAACCGT                                     28
```

(2) INFORMATION FOR SEQ ID NO:56:

(i) SEQUENCE CHARACTERISTICS:
        (A) LENGTH: 2225 base pairs
        (B) TYPE: nucleic acid
        (C) STRANDEDNESS: double
        (D) TOPOLOGY: unknown (ii) MOLECULE TYPE: mRNA to cDNA (iii) HYPOTHETICAL: NO (iv) ANTI-SENSE: NO (vi) ORIGINAL SOURCE:
        (C) INDIVIDUAL ISOLATE: spliced region of Towne strain HCMV
            containing sense transcript ORFs -continued (xi) SEQUENCE DESCRIPTION: SEQ ID NO:56:

```
GGCGACCGCC CAGCGACCCC CGCCCGTTGA CGTCAATAGT GACGTATGTT CCCATAGTAA      60
CGCCAATAGG GACTTTCCAT TGACGTCAAT GGGTGGAGTA TTTACGGTAA ACTGCCCACT     120
TGGCAGTACA TCAAGTGTAT CATATGCCAA GTCCGCCCCC TATTGACGTC AATGACGGTA     180
AATGGCCCGC CTAGCATTAT GCCCAGTACA TGACCTTACG GGAGTTTCCT ACTTGGCAGT     240
ACATCTACGT ATTAGTCATC GCTATTACCA TGGTGATGCG GTTTTGGCAG TACACCAATG     300
GGCGTGGATA GCGGTTTGAC TCACGGGGAT TTCCAAGTCT CCACCCCATT GACGTCAATG     360
GGAGTTTGTT TTGGCACCAA AATCAACGGG ACTTTCCAAA ATGTCGTAAT AACCCCGCCC     420
CGTTGACGCA AATGGGCGGT AGGCGTGTAC GGTGGGAGGT CTATATAAGC AGAGCTCGTT     480
TAGTGAACCG TCAGATCGCC TGGAGACGCC ATCCACGCTG TTTTGACCTC CATAGAAGAC     540
ACCGGGACCG ATCCAGCCTC CGCGGCCGGG AACGGTGCAT TGGAACGCGG ATTCCCCGTG     600
CCAAGAGTGA CTCACCGTCC TTGACACGAT GGAGTCCTCT GCCAAGAGAA AGATGGACCC     660
TGATAATCCT GACGAGGGCC CTTCCTCCAA GGTGCCACGG CCCAGACACC CCGTGACCAA     720
GGCCACGACG TTCCTGCAGA CTATGTTGAG GAAGGAGGTT AACAGTCAGC TGAGTCTGGG     780
AGACCCGCTG TTTCCAGAGT TGGCCGAAGA ATCCCTCAAA ACTTTTGAAC GAGTGACCGA     840
GGATTGCAAC GAGAACCCCG AGAAAGATGT CCTGGCAGAA CTCGTCAAAC AGATTAAGGT     900
TCGAGTGGAC ATGCTGCGGC ATAGAATCAA GGAGCACATG CTGAAAAAAT ATACCCAGAC     960
GGAAGAGAAA TTCACTGGCG CCTTTAATAT GATGGGAGGA TGTTTGCAGA ATGCCTTAGA    1020
TATCTTAGAT AAGGTTCATG AGCCTTTCGA GGAGATGAAG TGTATTGGGC TAACTATGCA    1080
GAGCATGTAT GAGAACTACA TTGTACCTGA GGATAAGCGG GAGATGTGGA TGGCTTGTAT    1140
TAAGGAGCTG CATGATGTGA GCAAGGGCGC CGCTAACAAG TTGGGGGGTG CACTGCAGGC    1200
TAAGGCCCGT GCTAAAAAGG ATGAACTTAG GAGAAAGATG ATGTATATGT GCTACAGGAA    1260
TATAGAGTTC TTTACCAAGA ACTCAGCCTT CCCTAAGACC ACCAATGGCT GCAGTCAGGC    1320
CATGGCGGCA TTGCAGAACT TGCCTCAGTG CTCCCCTGAT GAGATTATGG CTTATGCCCA    1380
GAAAATATTT AAGATTTTGG ATGAGGAGAG AGACAAGGTG CTCACGCACA TTGATCACAT    1440
ATTTATGGAT ATCCTCACTA CATGTGTGGA AACAATGTGT AATGAGTACA AGGTCACTAG    1500
TGACGCTTGT ATGATGACCA TGTACGGGGG CATCTCTCTC TTAAGTGAGT TCTGTCGGGT    1560
GCTGTCCTGC TATGTCTTAG AGGAGACTAG TGTGATGCTG GCCAAGCGGC CTCTGATAAC    1620
CAAGCCTGAG GTTATCAGTG TAATGAAGCG CCGCATTGAG GAGATCTGCA TGAAGGTCTT    1680
TGCCCAGTAC ATTCTGGGGG CCGATCCTCT GAGAGTCTGC TCTCCTAGTG TGGATGACCT    1740
ACGGGCCATC GCCGAGGAGT CAGATGAGGA AGAGGCTATT GTAGCCTACA CTTTGGCCAC    1800
CCGTGGTGCC AGCTCCTCTG ATTCTCTGGT GTCACCCCCA GAGTCCCCTG TACCCGCGAC    1860
TATCCCTCTG TCCTCAGTAA TTGTGGCTGA GAACAGTGAT CAGGAAGAAA GTGAGCAGAG    1920
TGATGAGGAA GAGGAGGAGG GTGCTCAGGA GGAGCGGGAG GACACTGTGT CTGTCAAGTC    1980
TGAGCCAGTG TCTGAGATAG AGGAAGTTGC CCCAGAGGAA GAGGAGGATG GTGCTGAGGA    2040
ACCCACCGCC TCTGGAGGCA AGAGCACCCA CCCTATGGTG ACTAGAAGCA AGGCTGACCA    2100
GTAAACTATT GTATATATAT ATCAGTTACT GTTATGGATC CCACGTCACT ATTGTATACT    2160
CTATATTATA CTCTATGTTA TACTCTGTAA TCCTACTCAA TAAACGTGTC ACGCCTGTGA    2220
AACCG                                                               2225
```

(2) INFORMATION FOR SEQ ID NO:57:

(i) SEQUENCE CHARACTERISTICS:
        (A) LENGTH: 2057 base pairs
        (B) TYPE: nucleic acid
        (C) STRANDEDNESS: double
        (D) TOPOLOGY: unknown (ii) MOLECULE TYPE: cDNA to mRNA (iii) HYPOTHETICAL: NO (iv) ANTI-SENSE: YES (vi) ORIGINAL SOURCE:
        (C) INDIVIDUAL ISOLATE: region of AD169 strain HCMV
            (antisense) containing antisense transcript ORFs (xi) SEQUENCE DESCRIPTION: SEQ ID NO:57:

```
GTGACACCAG AGAATCAGAG GAGCTGACAC CAGCGGTGGC CAAAGTGTAG GCTACAATAG       60

CCTCTTCCTC ATCTGACTCC TCGGCGATGG CCCGTAGGTC ATCCACACTA GGAGAGCAGA      120

CTCTCAGAGG ATCGGCCCCC AGAATGTACT GGGCAAAGAC CTTCATGCAG ATCTCCTCAA      180

TGCGGCGCTT CATTACACTG ATAACCTCAG GCTTGGTTAT CAGAGGCCGC TTGGCCAGCA      240

TCACACTAGT CTCCTCTAAG ACATAGCAGC ACAGCACCCG ACAGAACTCA CTTAAGAGAG      300

AGATGCCCCC GTACATGGTC ATCATACAAG CGTCACTAGT GACCTTGTAC TCATTACACA      360

TTGTTTCCAC ACATGTAGTG AGGATATCCA TAAATATGTG ATCAATGTGC GTGAGCACCT      420

TGTCTCTCTC CTCATCCAAA ATCTTAAATA TTTTCTGGGC ATAAGCCATA ATCTCATCAG      480

GGGAGCACTG AGGCAAGTTC TGCAGTGCCG CCATGGCCTG ACTGCAGCCA TTGGTGGTCT      540

TAGGGAAGGC TGAGTTCTTG GTAAAGAACT CTATATTCCT GTAGCACATA TACATCATCT      600

TTCTCCTAAG TTCATCCTTT TTAGCACGGG CCTTAGCCTG CAGTGCACCC CCCAACTTGT      660

TAGCGGCGCC CTTGCTCACA TCATGCAGCT CCTTAATACA AGCCATCCAC ATCTCCCGCT      720

TATCCTCAGG TACAATGTAG TTCTCATACA TGCTCTGCAT AGTTAGCCCA ATACACTTCA      780

TCTCCTCGAA AGGCTCATGA ACCTTATCTA AGATATCTAA GGCATTCTGC AAACATCCTC      840

CCATCATATT AAAGGCGCCA GTGAATTTCT CTTCCGTCTG GGTATATTTT TTCAGCATGT      900

GCTCCTTGAT TCTATGCCGC ACCATGTCCA CTCGAACCTT AATCTGTTTG ACTGTAGAGG      960

AGGATAACAA CACATATAAG TATCCGTCCT CCTGACTCAT TTATCGCTAT CTCGATGCCC     1020

CGCTCACATG CAAGAGTTAA TCTTTACTCT ATCTGACATA CACAAGTAAA TCCACGTCCC     1080

ATGCAGGTTA GTATACATCA CATACATGTC AACAGACTTA CCGAGTTCTG CCAGGACATC     1140

TTTCTCGGGG TTCTCGTTGC AATCCTCGGT CACTTGTTCA AAAGTTTTGA GGGATTCTTC     1200

GGCCAACTCT GGAAACAGCG GTCTCCCAG ACTCAGCTGA CTGTTAACCT CCTTCCTCAA      1260

CATAGTCTGC AGGAACGTCG TGGCCTTGGT CACGGGTGTC TCGGGCCTAA ACACATGAGA     1320

AATAGAGTCA TAAGCACATG GGTCACATAC AGGAGATATG TATATAACAT TAATACAATT     1380

TTATTAAAAA AAAAGGGGGG GCACAAACCC CGACACGTAC CGTGGCACCT TGGAGGAAGG     1440

GCCCTCGTCA GGATTATCAG GGTCCATCTT TCTCTTGGCA GAGGACTCCA TCGTGTCAAG     1500

GACGGTGACT GCAGAAAAGA CCCATGGAAA GGAACAGTCT GTTAGTCTGT CAGCTATTAT     1560

GTCTGGTGGC GCGCGCGGCA GCAACGAGTA CTGCTCAGAC TACACTGCCC TCCACCGTTA     1620

ACAGCACCGC AACGGGAGTT ACCTCTGACT CTTATCAGAA CACAACAACT CAGCTGCCTG     1680

CATCTTCTTC TGCCGCTGCC TTAAGTCTTC CAAATGCGTC AGCGGTGCAA GCCCGCTCCC     1740

CGAGCTCATT TTCAGACACA TACCCTACCG CCACGGCCTT GTGCGGCACA CTGGTGGTGG     1800
```

```
TGGGCATCGT GCTGTGCCTA AGTCTGGCCT CCACTGTTAG GAGCAAGGAG CTGCCGAGCG      1860

ACCATGAGTC GCTGGAGGCA TGGGAGCAGG GCTCGGATGT AGAAGCTCCG CCGCTACCGG      1920

AGAAGAGCCC ATGTCCGGAA CACGTACCCG AGATTCGCGT GGAGATCCCA CGTTATGTTT      1980

AATAAAAACT GCGGGCACTG GGACGGTGG TGTTGTATAT GTGAATTTGT AAATAATAAA       2040

TGAGACCCCA TCCTGTA                                                    2057
```

(2) INFORMATION FOR SEQ ID NO:58:

(i) SEQUENCE CHARACTERISTICS:
        (A) LENGTH: 135 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: sense ORF 1

(ix) FEATURE:
        (A) NAME/KEY: CDS
        (B) LOCATION: 1..135

(xi) SEQUENCE DESCRIPTION: SEQ ID NO:58:

```
ATG GCC CGC CTA GCA TTA TGC CCA GTA CAT GAC CTT ACG GGA GTT TCC       48
Met Ala Arg Leu Ala Leu Cys Pro Val His Asp Leu Thr Gly Val Ser
  1               5                  10                  15

TAC TTG GCA GTA CAT CTA CGT ATT AGT CAT CGC TAT TAC CAT GGT GAT       96
Tyr Leu Ala Val His Leu Arg Ile Ser His Arg Tyr Tyr His Gly Asp
             20                  25                  30

GCG GTT TTG GCA GTA CAC CAA TGG GCG TGG ATA GCG GTT                  135
Ala Val Leu Ala Val His Gln Trp Ala Trp Ile Ala Val
         35                  40                  45
```

(2) INFORMATION FOR SEQ ID NO:59:

(i) SEQUENCE CHARACTERISTICS:
        (A) LENGTH: 45 amino acids
        (B) TYPE: amino acid
        (D) TOPOLOGY: linear (ii) MOLECULE TYPE: protein (xi) SEQUENCE DESCRIPTION: SEQ ID NO:59:

```
Met Ala Arg Leu Ala Leu Cys Pro Val His Asp Leu Thr Gly Val Ser
  1               5                  10                  15

Tyr Leu Ala Val His Leu Arg Ile Ser His Arg Tyr Tyr His Gly Asp
             20                  25                  30

Ala Val Leu Ala Val His Gln Trp Ala Trp Ile Ala Val
         35                  40                  45
```

(2) INFORMATION FOR SEQ ID NO:60:

(i) SEQUENCE CHARACTERISTICS:
        (A) LENGTH: 126 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
             (C) INDIVIDUAL ISOLATE: sense ORF 2

(ix) FEATURE:
             (A) NAME/KEY: CDS
             (B) LOCATION: 1..126

(xi) SEQUENCE DESCRIPTION: SEQ ID NO:60:

```
ATG GGC GTG GAT AGC GGT TTG ACT CAC GGG GAT TTC CAA GTC TCC ACC    48
Met Gly Val Asp Ser Gly Leu Thr His Gly Asp Phe Gln Val Ser Thr
 1               5                  10                  15

CCA TTG ACG TCA ATG GGA GTT TGT TTT GGC ACC AAA ATC AAC GGG ACT    96
Pro Leu Thr Ser Met Gly Val Cys Phe Gly Thr Lys Ile Asn Gly Thr
             20                  25                  30

TTC CAA AAT GTC GTA ATA ACC CCG CCC CGT                           126
Phe Gln Asn Val Val Ile Thr Pro Pro Arg
             35                  40
```

(2) INFORMATION FOR SEQ ID NO:61:

(i) SEQUENCE CHARACTERISTICS:
             (A) LENGTH: 42 amino acids
             (B) TYPE: amino acid
             (D) TOPOLOGY: linear (ii) MOLECULE TYPE: protein (xi) SEQUENCE DESCRIPTION: SEQ ID NO:61:

```
Met Gly Val Asp Ser Gly Leu Thr His Gly Asp Phe Gln Val Ser Thr
 1               5                  10                  15

Pro Leu Thr Ser Met Gly Val Cys Phe Gly Thr Lys Ile Asn Gly Thr
             20                  25                  30

Phe Gln Asn Val Val Ile Thr Pro Pro Arg
             35                  40
```

(2) INFORMATION FOR SEQ ID NO:62:

(i) SEQUENCE CHARACTERISTICS:
             (A) LENGTH: 282 base pairs
             (B) TYPE: nucleic acid
             (C) STRANDEDNESS: double
             (D) TOPOLOGY: linear (ii) MOLECULE TYPE: cDNA to mRNA (iii) HYPOTHETICAL: NO (iv) ANTI-SENSE: NO (vi) ORIGINAL SOURCE:
             (C) INDIVIDUAL ISOLATE: sense ORF 3

(ix) FEATURE:
             (A) NAME/KEY: CDS
             (B) LOCATION: 1..282

(xi) SEQUENCE DESCRIPTION: SEQ ID NO:62:

```
ATG GGC GGT AGG CGT GTA CGG TGG GAG GTC TAT ATA AGC AGA GCT CGT    48
Met Gly Gly Arg Arg Val Arg Trp Glu Val Tyr Ile Ser Arg Ala Arg
 1               5                  10                  15

TTA GTG AAC CGT CAG ATC GCC TGG AGA CGC CAT CCA CGC TGT TTT GAC    96
Leu Val Asn Arg Gln Ile Ala Trp Arg Arg His Pro Arg Cys Phe Asp
             20                  25                  30

CTC CAT AGA AGA CAC CGG GAC CGA TCC AGC CTC CGC GGC CGG GAA CGG   144
```

```
              Leu His Arg Arg His Arg Asp Arg Ser Ser Leu Arg Gly Arg Glu Arg
                       35                  40                  45

TGC ATT GGA ACG CGG ATT CCC CGT GCC AAG AGT GAC TCA CCG TCC TTG          192
Cys Ile Gly Thr Arg Ile Pro Arg Ala Lys Ser Asp Ser Pro Ser Leu
         50                  55                  60

ACA CGA TGG AGT CCT CTG CCA AGA GAA AGA TGG ACC CTG ATA ATC CTG          240
Thr Arg Trp Ser Pro Leu Pro Arg Glu Arg Trp Thr Leu Ile Ile Leu
 65              70                  75                      80

ACG AGG GCC CTT CCT CCA AGG TGC CAC GGC CCG AGA CAC CCG                  282
Thr Arg Ala Leu Pro Pro Arg Cys His Gly Pro Arg His Pro
             85                  90
```

(2) INFORMATION FOR SEQ ID NO:63:

(i) SEQUENCE CHARACTERISTICS:
        (A) LENGTH: 94 amino acids
        (B) TYPE: amino acid
        (D) TOPOLOGY: linear (ii) MOLECULE TYPE: protein (xi) SEQUENCE DESCRIPTION: SEQ ID NO:63:

```
Met Gly Gly Arg Arg Val Arg Trp Glu Val Tyr Ile Ser Arg Ala Arg
 1               5                  10                  15

Leu Val Asn Arg Gln Ile Ala Trp Arg Arg His Pro Arg Cys Phe Asp
             20                  25                  30

Leu His Arg Arg His Arg Asp Arg Ser Ser Leu Arg Gly Arg Glu Arg
         35                  40                  45

Cys Ile Gly Thr Arg Ile Pro Arg Ala Lys Ser Asp Ser Pro Ser Leu
     50                  55                  60

Thr Arg Trp Ser Pro Leu Pro Arg Glu Arg Trp Thr Leu Ile Ile Leu
 65              70                  75                      80

Thr Arg Ala Leu Pro Pro Arg Cys His Gly Pro Arg His Pro
             85                  90
```

(2) INFORMATION FOR SEQ ID NO:64:

(i) SEQUENCE CHARACTERISTICS:
        (A) LENGTH: 177 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: antisense ORF 1

(ix) FEATURE:
        (A) NAME/KEY: CDS
        (B) LOCATION: 1..177

(xi) SEQUENCE DESCRIPTION: SEQ ID NO:64:

```
ATG GCC CGT AGG TCA TCC ACA CTA GGA GAG CAG ACT CTC AGA GGA TCG          48
Met Ala Arg Arg Ser Ser Thr Leu Gly Glu Gln Thr Leu Arg Gly Ser
 1               5                  10                  15

GCC CCC AGA ATG TAC TGG GCA AAG ACC TTC ATG CAG ATC TCC TCA ATG          96
Ala Pro Arg Met Tyr Trp Ala Lys Thr Phe Met Gln Ile Ser Ser Met
             20                  25                  30

CGG CGC TTC ATT ACA CTG ATA ACC TCA GGC TTG GTT ATC AGA GGC CGC         144
Arg Arg Phe Ile Thr Leu Ile Thr Ser Gly Leu Val Ile Arg Gly Arg
```

```
                  35                   40                  45
TTG GCC AGC ATC ACA CTA GTC TCC TCT AAG ACA                         177
Leu Ala Ser Ile Thr Leu Val Ser Ser Lys Thr
    50                  55
```

(2) INFORMATION FOR SEQ ID NO:65:

(i) SEQUENCE CHARACTERISTICS:
        (A) LENGTH: 59 amino acids
        (B) TYPE: amino acid
        (D) TOPOLOGY: linear (ii) MOLECULE TYPE: protein (xi) SEQUENCE DESCRIPTION: SEQ ID NO:65:

```
Met Ala Arg Arg Ser Ser Thr Leu Gly Glu Gln Thr Leu Arg Gly Ser
 1               5                  10                  15

Ala Pro Arg Met Tyr Trp Ala Lys Thr Phe Met Gln Ile Ser Ser Met
                20                  25                  30

Arg Arg Phe Ile Thr Leu Ile Thr Ser Gly Leu Val Ile Arg Gly Arg
            35                  40                  45

Leu Ala Ser Ile Thr Leu Val Ser Ser Lys Thr
    50                  55
```

(2) INFORMATION FOR SEQ ID NO:66:

(i) SEQUENCE CHARACTERISTICS:
        (A) LENGTH: 462 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: antisense ORF 2

(ix) FEATURE:
        (A) NAME/KEY: CDS
        (B) LOCATION: 1..462

(xi) SEQUENCE DESCRIPTION: SEQ ID NO:66:

```
ATG CAG GTT AGT ATA CAT CAC ATA CAT GTC AAC AGA CTT ACC GAG TTC    48
Met Gln Val Ser Ile His His Ile His Val Asn Arg Leu Thr Glu Phe
 1               5                  10                  15

TGC CAG GAC ATC TTT CTC GGG GTT CTC GTT GCA ATC CTC GGT CAC TTG    96
Cys Gln Asp Ile Phe Leu Gly Val Leu Val Ala Ile Leu Gly His Leu
                20                  25                  30

TTC AAA AGT TTT GAG GGA TTC TTC GGC CAA CTC TGG AAA CAG CGG GTC   144
Phe Lys Ser Phe Glu Gly Phe Phe Gly Gln Leu Trp Lys Gln Arg Val
            35                  40                  45

TCC CAG ACT CAG CTG ACT GTT AAC CTC CTT CCT CAA CAT AGT CTG CAG   192
Ser Gln Thr Gln Leu Thr Val Asn Leu Leu Pro Gln His Ser Leu Gln
    50                  55                  60

GAA CGT CGT GGC CTT GGT CAC GGG TGT CTC GGG CCT AAA CAC ATG AGA   240
Glu Arg Arg Gly Leu Gly His Gly Cys Leu Gly Pro Lys His Met Arg
65                  70                  75                  80

AAT AGA GTC ATA AGC ACA TGG GTC ACA TAC AGG AGA TAT GTA TAT AAC   288
Asn Arg Val Ile Ser Thr Trp Val Thr Tyr Arg Arg Tyr Val Tyr Asn
                85                  90                  95

ATT AAT ACA ATT TTA TTA AAA AAA AAG GGG GGG CAC AAA CCC CGA CAC   336
```

```
Ile Asn Thr Ile Leu Leu Lys Lys Lys Gly Gly His Lys Pro Arg His
            100                 105                 110

GTA CCG TGG CAC CTT GGA GGA AGG GCC CTC GTC AGG ATT ATC AGG GTC       384
Val Pro Trp His Leu Gly Gly Arg Ala Leu Val Arg Ile Ile Arg Val
            115                 120                 125

CAT CTT TCT CTT GGC AGA GGA CTC CAT CGT GTC AAG GAC GGT GAC TGC       432
His Leu Ser Leu Gly Arg Gly Leu His Arg Val Lys Asp Gly Asp Cys
            130                 135                 140

AGA AAA GAC CCA TGG AAA GGA ACA GTC TGT                               462
Arg Lys Asp Pro Trp Lys Gly Thr Val Cys
145                 150
```

(2) INFORMATION FOR SEQ ID NO:67:

(i) SEQUENCE CHARACTERISTICS:
        (A) LENGTH: 154 amino acids
        (B) TYPE: amino acid
        (D) TOPOLOGY: linear (ii) MOLECULE TYPE: protein (xi) SEQUENCE DESCRIPTION: SEQ ID NO:67:

```
Met Gln Val Ser Ile His His Ile His Val Asn Arg Leu Thr Glu Phe
 1               5                  10                  15

Cys Gln Asp Ile Phe Leu Gly Val Leu Val Ala Ile Leu Gly His Leu
            20                  25                  30

Phe Lys Ser Phe Glu Gly Phe Phe Gly Gln Leu Trp Lys Gln Arg Val
            35                  40                  45

Ser Gln Thr Gln Leu Thr Val Asn Leu Leu Pro Gln His Ser Leu Gln
            50                  55                  60

Glu Arg Arg Gly Leu Gly His Gly Cys Leu Gly Pro Lys His Met Arg
65                  70                  75                  80

Asn Arg Val Ile Ser Thr Trp Val Thr Tyr Arg Arg Tyr Val Tyr Asn
                85                  90                  95

Ile Asn Thr Ile Leu Leu Lys Lys Lys Gly Gly His Lys Pro Arg His
            100                 105                 110

Val Pro Trp His Leu Gly Gly Arg Ala Leu Val Arg Ile Ile Arg Val
            115                 120                 125

His Leu Ser Leu Gly Arg Gly Leu His Arg Val Lys Asp Gly Asp Cys
            130                 135                 140

Arg Lys Asp Pro Trp Lys Gly Thr Val Cys
145                 150
```

(2) INFORMATION FOR SEQ ID NO:68:

(i) SEQUENCE CHARACTERISTICS:
        (A) LENGTH: 132 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: antisense ORF 3

(ix) FEATURE:
        (A) NAME/KEY: CDS
        (B) LOCATION: 1..132

(xi) SEQUENCE DESCRIPTION: SEQ ID NO:68:

```
ATG TCA ACA GAC TTA CCG AGT TCT GCC AGG ACA TCT TTC TCG GGG TTC      48
Met Ser Thr Asp Leu Pro Ser Ser Ala Arg Thr Ser Phe Ser Gly Phe
 1               5                  10                  15

TCG TTG CAA TCC TCG GTC ACT TGT TCA AAA GTT TTG AGG GAT TCT TCG      96
Ser Leu Gln Ser Ser Val Thr Cys Ser Lys Val Leu Arg Asp Ser Ser
            20                  25                  30

GCC AAC TCT GGA AAC AGC GGG TCT CCC AGA CTC AGC                     132
Ala Asn Ser Gly Asn Ser Gly Ser Pro Arg Leu Ser
        35                  40
```

(2) INFORMATION FOR SEQ ID NO:69:

(i) SEQUENCE CHARACTERISTICS:
        (A) LENGTH: 44 amino acids
        (B) TYPE: amino acid
        (D) TOPOLOGY: linear (ii) MOLECULE TYPE: protein (xi) SEQUENCE DESCRIPTION: SEQ ID NO:69:

```
Met Ser Thr Asp Leu Pro Ser Ser Ala Arg Thr Ser Phe Ser Gly Phe
 1               5                  10                  15

Ser Leu Gln Ser Ser Val Thr Cys Ser Lys Val Leu Arg Asp Ser Ser
            20                  25                  30

Ala Asn Ser Gly Asn Ser Gly Ser Pro Arg Leu Ser
        35                  40
```

(2) INFORMATION FOR SEQ ID NO:70:

(i) SEQUENCE CHARACTERISTICS:
        (A) LENGTH: 456 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: antisense ORF 4

(ix) FEATURE:
        (A) NAME/KEY: CDS
        (B) LOCATION: 1..456

(xi) SEQUENCE DESCRIPTION: SEQ ID NO:70:

```
ATG GAA AGG AAC AGT CTG TTA GTC TGT CAG CTA TTA TGT CTG GTG GCG      48
Met Glu Arg Asn Ser Leu Leu Val Cys Gln Leu Leu Cys Leu Val Ala
 1               5                  10                  15

CGC GCG GCA GCA ACG AGT ACT GCT CAG ACT ACA CTG CCC TCC ACC GTT      96
Arg Ala Ala Ala Thr Ser Thr Ala Gln Thr Thr Leu Pro Ser Thr Val
            20                  25                  30

AAC AGC ACC GCA ACG GGA GTT ACC TCT GAC TCT TAT CAG AAC ACA ACA     144
Asn Ser Thr Ala Thr Gly Val Thr Ser Asp Ser Tyr Gln Asn Thr Thr
        35                  40                  45

ACT CAG CTG CCT GCA TCT TCT TCT GCC GCT GCC TTA AGT CTT CCA AAT     192
Thr Gln Leu Pro Ala Ser Ser Ser Ala Ala Ala Leu Ser Leu Pro Asn
    50                  55                  60

GCG TCA GCG GTG CAA GCC CGC TCC CCG AGC TCA TTT TCA GAC ACA TAC     240
Ala Ser Ala Val Gln Ala Arg Ser Pro Ser Ser Phe Ser Asp Thr Tyr
65                  70                  75                  80
```

```
CCT ACC GCC ACG GCC TTG TGC GGC ACA CTG GTG GTG GTG GGC ATC GTG      288
Pro Thr Ala Thr Ala Leu Cys Gly Thr Leu Val Val Val Gly Ile Val
                85                  90                  95

CTG TGC CTA AGT CTG GCC TCC ACT GTT AGG AGC AAG GAG CTG CCG AGC      336
Leu Cys Leu Ser Leu Ala Ser Thr Val Arg Ser Lys Glu Leu Pro Ser
            100                 105                 110

GAC CAT GAG TCG CTG GAG GCA TGG GAG CAG GGC TCG GAT GTA GAA GCT      384
Asp His Glu Ser Leu Glu Ala Trp Glu Gln Gly Ser Asp Val Glu Ala
        115                 120                 125

CCG CCG CTA CCG GAG AAG AGC CCA TGT CCG GAA CAC GTA CCC GAG ATT      432
Pro Pro Leu Pro Glu Lys Ser Pro Cys Pro Glu His Val Pro Glu Ile
    130                 135                 140

CGC GTG GAG ATC CCA CGT TAT GTT                                      456
Arg Val Glu Ile Pro Arg Tyr Val
145             150
```

(2) INFORMATION FOR SEQ ID NO:71:

(i) SEQUENCE CHARACTERISTICS:
        (A) LENGTH: 152 amino acids
        (B) TYPE: amino acid
        (D) TOPOLOGY: linear (ii) MOLECULE TYPE: protein (xi) SEQUENCE DESCRIPTION: SEQ ID NO:71:

```
Met Glu Arg Asn Ser Leu Leu Val Cys Gln Leu Leu Cys Leu Val Ala
1               5                   10                  15

Arg Ala Ala Ala Thr Ser Thr Ala Gln Thr Thr Leu Pro Ser Thr Val
                20                  25                  30

Asn Ser Thr Ala Thr Gly Val Thr Ser Asp Ser Tyr Gln Asn Thr Thr
            35                  40                  45

Thr Gln Leu Pro Ala Ser Ser Ala Ala Leu Ser Leu Pro Asn
        50                  55                  60

Ala Ser Ala Val Gln Ala Arg Ser Pro Ser Ser Phe Ser Asp Thr Tyr
65                  70                  75                  80

Pro Thr Ala Thr Ala Leu Cys Gly Thr Leu Val Val Val Gly Ile Val
                85                  90                  95

Leu Cys Leu Ser Leu Ala Ser Thr Val Arg Ser Lys Glu Leu Pro Ser
            100                 105                 110

Asp His Glu Ser Leu Glu Ala Trp Glu Gln Gly Ser Asp Val Glu Ala
        115                 120                 125

Pro Pro Leu Pro Glu Lys Ser Pro Cys Pro Glu His Val Pro Glu Ile
    130                 135                 140

Arg Val Glu Ile Pro Arg Tyr Val
145             150
```

(2) INFORMATION FOR SEQ ID NO:72:

(i) SEQUENCE CHARACTERISTICS:
        (A) LENGTH: 150 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: antisense ORF 5

(ix) FEATURE:
    (A) NAME/KEY: CDS
    (B) LOCATION: 1..150

(xi) SEQUENCE DESCRIPTION: SEQ ID NO:72:

```
ATG GGA GCA GGG CTC GGA TGT AGA AGC TCC GCC GCT ACC GGA GAA GAG      48
Met Gly Ala Gly Leu Gly Cys Arg Ser Ser Ala Ala Thr Gly Glu Glu
 1               5                  10                  15

CCC ATG TCC GGA ACA CGT ACC CGA GAT TCG CGT GGA GAT CCC ACG TTA      96
Pro Met Ser Gly Thr Arg Thr Arg Asp Ser Arg Gly Asp Pro Thr Leu
                20                  25                  30

TGT TTA ATA AAA ACT GCG GGC ACT GGG GAC GGT GGT GTT GTA TAT GTG     144
Cys Leu Ile Lys Thr Ala Gly Thr Gly Asp Gly Gly Val Val Tyr Val
             35                  40                  45

AAT TTG                                                             150
Asn Leu
   50
```

(2) INFORMATION FOR SEQ ID NO:73:

(i) SEQUENCE CHARACTERISTICS:
       (A) LENGTH: 50 amino acids
       (B) TYPE: amino acid
       (D) TOPOLOGY: linear (ii) MOLECULE TYPE: protein (xi) SEQUENCE DESCRIPTION: SEQ ID NO:73:

```
Met Gly Ala Gly Leu Gly Cys Arg Ser Ser Ala Ala Thr Gly Glu Glu
 1               5                  10                  15

Pro Met Ser Gly Thr Arg Thr Arg Asp Ser Arg Gly Asp Pro Thr Leu
                20                  25                  30

Cys Leu Ile Lys Thr Ala Gly Thr Gly Asp Gly Gly Val Val Tyr Val
             35                  40                  45

Asn Leu
   50
```

(2) INFORMATION FOR SEQ ID NO:74:

(i) SEQUENCE CHARACTERISTICS:
       (A) LENGTH: 51 base pairs
       (B) TYPE: nucleic acid
       (C) STRANDEDNESS: double
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
       (C) INDIVIDUAL ISOLATE: exon 5 splice junction 1 of 1.5/1.6
           kb transcripts (xi) SEQUENCE DESCRIPTION: SEQ ID NO:74:

CCACGCGTCC TTTCAGGTGA TTATTTCGTC TTCCTCCTGC AGTTCGGCTT C            51

(2) INFORMATION FOR SEQ ID NO:75:

(i) SEQUENCE CHARACTERISTICS:
       (A) LENGTH: 45 base pairs
       (B) TYPE: nucleic acid
       (C) STRANDEDNESS: double
       (D) TOPOLOGY: linear -continued

```
    (ii) MOLECULE TYPE: DNA (genomic)

(iii) HYPOTHETICAL: NO (iv) ANTI-SENSE: NO (vi) ORIGINAL SOURCE:
          (C) INDIVIDUAL ISOLATE: exon 5 splice junction 2 of 1.5/1.6
              kb transcripts (xi) SEQUENCE DESCRIPTION: SEQ ID NO:75:

AAGATTGACG AGGTGAGCCG CATTTCCCAA ACAGGTCATG GTGCG                    45
```